United States Patent
Gupta et al.

(10) Patent No.: US 10,638,979 B2
(45) Date of Patent: May 5, 2020

(54) ANALYTE SENSOR DATA EVALUATION AND ERROR REDUCTION APPARATUS AND METHODS

(71) Applicant: GlySens Incorporated, San Diego, CA (US)

(72) Inventors: Piyush Gupta, San Diego, CA (US); Joseph Lucisano, San Diego, CA (US)

(73) Assignee: GlySens Incorporated, San Diego, CA (US)

( * ) Notice: Subject to any disclaimer, the term of this patent is extended or adjusted under 35 U.S.C. 154(b) by 134 days.

(21) Appl. No.: 15/645,913

(22) Filed: Jul. 10, 2017

(65) Prior Publication Data

US 2019/0008461 A1 Jan. 10, 2019

(51) Int. Cl.
*A61B 5/145* (2006.01)
*A61B 5/00* (2006.01)
(Continued)

(52) U.S. Cl.
CPC .......... *A61B 5/7267* (2013.01); *A61B 5/0022* (2013.01); *A61B 5/1473* (2013.01);
(Continued)

(58) Field of Classification Search
CPC .............. A61B 2560/0223; A61B 5/145–1495
See application file for complete search history.

(56) References Cited

U.S. PATENT DOCUMENTS

| | | |
|---|---|---|
| 2,508,523 A | 5/1950 | Krebs |
| 2,563,062 A | 8/1951 | Perley |

(Continued)

FOREIGN PATENT DOCUMENTS

| | | |
|---|---|---|
| EP | 0852414 B1 | 11/2004 |
| WO | WO-9207525 A1 | 5/1992 |

(Continued)

OTHER PUBLICATIONS

Machine learning. (1992). In C. G. Morris (Ed.), Academic Press Dictionary of Science and Technology (4th ed.). Oxford, UK: Elsevier Science & Technology. Retrieved from https://search.credoreference.com/content/entry/apdst/machine_learning/0?institutionId=743 (Year: 1992).*

(Continued)

*Primary Examiner* — David J. McCrosky
(74) *Attorney, Agent, or Firm* — Gazdzinski & Associates, PC

(57) ABSTRACT

Apparatus and methods for error modeling and correction in a blood analyte sensor or system. In one exemplary embodiment, the apparatus employs: (i) a training mode of operation, whereby the apparatus conducts "machine learning" to model one or more errors (e.g., unmodeled variable system errors) associated with the blood analyte measurement process, and (ii) generation of an operational model (based at least in part on data collected/received in the training mode), which is applied to correct or compensate for the errors during normal operation and collection of blood analyte data. This enhances device signal stability and accuracy over extended periods, thereby enabling among other things extended periods of blood analyte sensor implantation, and "personalization" of the sensor apparatus to each user receiving an implant. In one variant, the blood analyte is glucose, and the implanted sensor utilizes an oxygen-based molecular measurement principle.

20 Claims, 21 Drawing Sheets

(51) Int. Cl.

| | |
|---|---|
| *A61B 5/1473* | (2006.01) |
| *G06N 99/00* | (2019.01) |
| *G16H 50/50* | (2018.01) |
| *G06N 20/00* | (2019.01) |
| *G16H 40/67* | (2018.01) |
| *G16H 10/40* | (2018.01) |
| *G06N 5/00* | (2006.01) |
| *G06N 20/10* | (2019.01) |
| *G16H 50/70* | (2018.01) |
| *G06N 20/20* | (2019.01) |

(52) U.S. Cl.
CPC .......... *A61B 5/14532* (2013.01); *A61B 5/686* (2013.01); *G06N 5/003* (2013.01); *G06N 20/00* (2019.01); *G06N 20/10* (2019.01); *G06N 20/20* (2019.01); *G06N 99/005* (2013.01); *G16H 10/40* (2018.01); *G16H 40/67* (2018.01); *G16H 50/50* (2018.01); *G16H 50/70* (2018.01); *A61B 2560/0223* (2013.01)

(56) References Cited

U.S. PATENT DOCUMENTS

| | | |
|---|---|---|
| 2,805,191 A | 9/1957 | Hersch |
| 2,864,750 A | 12/1958 | Hughes, Jr. et al. |
| 2,998,371 A | 8/1961 | Sabins |
| 3,099,575 A | 7/1963 | Hill |
| 3,246,235 A | 4/1966 | Allsopp |
| 3,249,250 A | 5/1966 | McKee |
| 3,300,345 A | 1/1967 | Lyons, Jr. |
| 3,308,046 A | 3/1967 | Suleski |
| 3,458,421 A | 7/1969 | Harald |
| 3,505,195 A | 4/1970 | Borge et al. |
| 3,542,662 A | 11/1970 | George et al. |
| 3,616,412 A | 10/1971 | Gnage |
| 3,957,613 A | 5/1976 | Macur |
| 4,036,716 A | 7/1977 | Hulthe |
| 4,088,550 A | 5/1978 | Malkin |
| 4,240,438 A | 12/1980 | Shults et al. |
| 4,306,952 A | 12/1981 | Jansen |
| 4,340,457 A | 7/1982 | Kater |
| 4,361,153 A | 11/1982 | Slocum et al. |
| 4,366,033 A | 12/1982 | Richter et al. |
| 4,431,004 A | 2/1984 | Bessman et al. |
| 4,458,686 A | 7/1984 | Clark, Jr. |
| 4,484,987 A | 11/1984 | Gough |
| 4,494,950 A | 1/1985 | Fischell |
| 4,541,431 A | 9/1985 | Ibrahim et al. |
| 4,550,732 A | 11/1985 | Batty, Jr. et al. |
| 4,553,547 A | 11/1985 | Keimel |
| 4,571,589 A | 2/1986 | Slocum et al. |
| 4,637,861 A | 1/1987 | Krull et al. |
| 4,650,547 A | 3/1987 | Gough |
| 4,671,288 A | 6/1987 | Gough |
| 4,703,756 A | 11/1987 | Gough et al. |
| 4,746,218 A | 5/1988 | Lord, III |
| 4,748,562 A | 5/1988 | Miller et al. |
| 4,759,828 A | 7/1988 | Young et al. |
| 4,781,798 A | 11/1988 | Gough |
| 4,830,713 A | 5/1989 | Gagescu |
| 4,890,620 A | 1/1990 | Gough |
| 5,046,242 A | 9/1991 | Kuzma |
| 5,077,476 A | 12/1991 | Rosenthal |
| 5,105,811 A | 4/1992 | Kuzma |
| 5,112,455 A | 5/1992 | Cozzette et al. |
| 5,165,406 A | 11/1992 | Wong |
| 5,264,103 A | 11/1993 | Yoshioka et al. |
| 5,272,283 A | 12/1993 | Kuzma |
| 5,273,203 A | 12/1993 | Webster |
| 5,283,104 A | 2/1994 | Aoude et al. |
| 5,283,204 A | 2/1994 | Rhodes et al. |
| 5,284,140 A | 2/1994 | Allen et al. |
| 5,322,063 A | 6/1994 | Allen et al. |
| 5,337,475 A | 8/1994 | Aoude et al. |
| 5,395,504 A | 3/1995 | Saurer et al. |
| 5,431,160 A | 7/1995 | Wilkins |
| 5,487,855 A | 1/1996 | Moeggenborg et al. |
| 5,497,772 A | 3/1996 | Schulman et al. |
| 5,560,098 A | 10/1996 | Robins |
| 5,660,163 A | 8/1997 | Schulman et al. |
| 5,695,623 A | 12/1997 | Michel et al. |
| 5,711,861 A | 1/1998 | Ward et al. |
| 5,727,283 A | 3/1998 | Webster |
| 5,741,330 A | 4/1998 | Brauker et al. |
| 5,750,926 A | 5/1998 | Schulman et al. |
| 5,776,324 A | 7/1998 | Usala |
| 5,777,060 A | 7/1998 | Van Antwerp |
| 5,782,755 A | 7/1998 | Chance et al. |
| 5,782,891 A | 7/1998 | Hassler et al. |
| 5,791,344 A | 8/1998 | Schulman et al. |
| 5,804,048 A | 9/1998 | Wong et al. |
| 5,821,011 A | 10/1998 | Taylor et al. |
| 5,842,983 A | 12/1998 | Abel et al. |
| 5,855,995 A | 1/1999 | Haq et al. |
| 5,864,088 A | 1/1999 | Sato et al. |
| 5,882,494 A | 3/1999 | Van Antwerp |
| 5,887,240 A | 3/1999 | Fournier et al. |
| 5,932,175 A | 8/1999 | Knute et al. |
| 5,942,842 A | 8/1999 | Fogle, Jr. |
| 5,964,993 A | 10/1999 | Blubaugh, Jr. |
| 5,985,129 A | 11/1999 | Gough et al. |
| 6,001,067 A | 12/1999 | Shults et al. |
| 6,027,479 A | 2/2000 | Alei et al. |
| 6,041,496 A | 3/2000 | Haq et al. |
| 6,081,736 A | 6/2000 | Colvin et al. |
| 6,090,503 A | 7/2000 | Taylor et al. |
| 6,107,083 A | 8/2000 | Collins et al. |
| 6,119,208 A | 9/2000 | White et al. |
| 6,200,772 B1 | 3/2001 | Vadgama et al. |
| 6,212,416 B1 | 4/2001 | Ward et al. |
| 6,221,513 B1 | 4/2001 | Lasater |
| 6,403,944 B1 | 6/2002 | MacKenzie et al. |
| 6,466,810 B1 | 10/2002 | Ward et al. |
| 6,516,808 B2 | 2/2003 | Schulman |
| 6,551,252 B2 | 4/2003 | Sackner et al. |
| 6,558,321 B1 | 5/2003 | Burd et al. |
| 6,642,015 B2 | 11/2003 | Vachon et al. |
| 6,721,587 B2 | 4/2004 | Gough |
| 6,741,877 B1 | 5/2004 | Shults et al. |
| 6,809,607 B2 | 10/2004 | Nagasaka |
| 6,812,404 B1 | 11/2004 | Martinez |
| 6,832,114 B1 | 12/2004 | Whitehurst et al. |
| 6,931,268 B1 | 8/2005 | Kiani-Azarbayjany et al. |
| 7,079,881 B2 | 7/2006 | Schulman et al. |
| 7,110,803 B2 | 9/2006 | Shults et al. |
| 7,134,999 B2 | 11/2006 | Brauker et al. |
| 7,136,689 B2 | 11/2006 | Shults et al. |
| 7,146,203 B2 | 12/2006 | Botvinick et al. |
| 7,189,341 B2 | 3/2007 | Li et al. |
| 7,226,978 B2 | 6/2007 | Tapsak et al. |
| 7,248,912 B2 | 7/2007 | Gough et al. |
| 7,336,984 B2 | 2/2008 | Gough et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,480,988 B2 | 1/2009 | Ok et al. |
| 7,497,827 B2 | 3/2009 | Brister et al. |
| 7,514,791 B2 | 4/2009 | Shah et al. |
| 7,525,298 B2 | 4/2009 | Morgan et al. |
| 7,761,130 B2 | 7/2010 | Simpson et al. |
| 7,857,760 B2 | 12/2010 | Brister et al. |
| 7,871,456 B2 | 1/2011 | Gough et al. |
| 7,875,293 B2 | 1/2011 | Shults et al. |
| 7,881,763 B2 | 2/2011 | Brauker et al. |
| 7,894,870 B1 | 2/2011 | Lucisano et al. |
| 8,133,178 B2 | 3/2012 | Brauker et al. |
| 8,270,661 B2 | 9/2012 | Sorensen et al. |
| 8,357,107 B2 | 1/2013 | Draudt et al. |
| 8,690,820 B2 | 4/2014 | Cinar et al. |
| 8,763,245 B1 | 7/2014 | Lucisano et al. |
| 9,002,711 B2 | 4/2015 | Morinaka et al. |

(56) References Cited

U.S. PATENT DOCUMENTS

| | | | |
|---|---|---|---|
| 9,119,528 B2 | 9/2015 | Cobelli et al. | |
| 9,247,901 B2 | 2/2016 | Kamath et al. | |
| 9,325,060 B2 | 4/2016 | Kalistaja et al. | |
| 9,362,776 B2 | 6/2016 | Low et al. | |
| 9,444,027 B2 | 9/2016 | Dibra et al. | |
| 9,451,908 B2 | 9/2016 | Kamath et al. | |
| 2002/0026108 A1 | 2/2002 | Colvin et al. | |
| 2002/0123087 A1 | 9/2002 | Vachon et al. | |
| 2002/0156355 A1 | 10/2002 | Gough | |
| 2002/0161286 A1 | 10/2002 | Gerber et al. | |
| 2002/0193671 A1 | 12/2002 | Ciurczak et al. | |
| 2003/0048621 A1 | 3/2003 | Blood et al. | |
| 2003/0049166 A1 | 3/2003 | Pendo et al. | |
| 2003/0053784 A1 | 3/2003 | Labrake et al. | |
| 2003/0126593 A1 | 7/2003 | Mault | |
| 2003/0179167 A1 | 9/2003 | Kolluri et al. | |
| 2003/0181794 A1 | 9/2003 | Rini et al. | |
| 2003/0217966 A1 | 11/2003 | Tapsak et al. | |
| 2004/0011671 A1 | 1/2004 | Shults et al. | |
| 2004/0012935 A1 | 1/2004 | Tagi et al. | |
| 2004/0057043 A1 | 3/2004 | Newman et al. | |
| 2004/0106857 A1 | 6/2004 | Gough et al. | |
| 2004/0158194 A1 | 8/2004 | Wolff et al. | |
| 2004/0167080 A1 | 8/2004 | Dodge et al. | |
| 2004/0176669 A1 | 9/2004 | Colvin et al. | |
| 2004/0190111 A1 | 9/2004 | Callies et al. | |
| 2004/0199059 A1 | 10/2004 | Brauker et al. | |
| 2004/0220459 A1 | 11/2004 | Schlegel et al. | |
| 2005/0027175 A1 | 2/2005 | Yang | |
| 2005/0031689 A1 | 2/2005 | Shults et al. | |
| 2005/0033132 A1 | 2/2005 | Shults et al. | |
| 2005/0059871 A1 | 3/2005 | Gough et al. | |
| 2005/0124873 A1 | 6/2005 | Shults et al. | |
| 2005/0154271 A1 | 7/2005 | Rasdal et al. | |
| 2005/0177036 A1 | 8/2005 | Shults et al. | |
| 2005/0196322 A1 | 9/2005 | Truex et al. | |
| 2005/0245799 A1 | 11/2005 | Brauker et al. | |
| 2005/0245971 A1 | 11/2005 | Brockway et al. | |
| 2005/0251083 A1 | 11/2005 | Carr-Brendel et al. | |
| 2005/0272989 A1 | 12/2005 | Shah et al. | |
| 2006/0085137 A1 | 4/2006 | Bartkowiak et al. | |
| 2006/0086624 A1 | 4/2006 | Tapsak et al. | |
| 2006/0195029 A1 | 8/2006 | Shults et al. | |
| 2006/0257995 A1 | 11/2006 | Simpson et al. | |
| 2006/0257996 A1 | 11/2006 | Simpson et al. | |
| 2006/0263763 A1 | 11/2006 | Simpson et al. | |
| 2007/0151868 A1 | 7/2007 | Staib et al. | |
| 2008/0033269 A1 | 2/2008 | Zhang | |
| 2008/0033272 A1 | 2/2008 | Gough et al. | |
| 2008/0039702 A1 | 2/2008 | Hayter et al. | |
| 2008/0197024 A1 | 8/2008 | Simpson et al. | |
| 2008/0200791 A1 | 8/2008 | Simpson et al. | |
| 2008/0317276 A1 | 12/2008 | Sorensen et al. | |
| 2009/0281399 A1 | 11/2009 | Keel et al. | |
| 2010/0041971 A1 | 2/2010 | Goode, Jr. et al. | |
| 2010/0149042 A1 | 6/2010 | Utsi et al. | |
| 2011/0137142 A1 | 6/2011 | Lucisano et al. | |
| 2012/0262298 A1 | 10/2012 | Bohm et al. | |
| 2012/0283960 A1 | 11/2012 | Budiman | |
| 2012/0323100 A1* | 12/2012 | Kamath | A61B 5/01 600/365 |
| 2013/0016573 A1 | 1/2013 | Goel et al. | |
| 2013/0030273 A1 | 1/2013 | Tapsak et al. | |
| 2013/0197332 A1 | 8/2013 | Lucisano et al. | |
| 2014/0046148 A1 | 2/2014 | Simpson et al. | |
| 2014/0309510 A1 | 10/2014 | Lucisano et al. | |
| 2014/0350652 A1 | 11/2014 | Suwito | |
| 2015/0250429 A1 | 9/2015 | Hampapuram et al. | |
| 2015/0289823 A1 | 10/2015 | Rack-Gomer et al. | |
| 2016/0073964 A1* | 3/2016 | Cobelli | A61B 5/14532 600/365 |
| 2016/0134980 A1 | 5/2016 | Abolfathi | |
| 2016/0163174 A1 | 6/2016 | Zhang | |
| 2016/0317744 A1 | 11/2016 | Rule | |
| 2017/0181628 A1 | 6/2017 | Burnette et al. | |
| 2017/0181630 A1 | 6/2017 | Mahalingam et al. | |
| 2017/0181674 A1 | 6/2017 | Lucisano et al. | |
| 2017/0347932 A1 | 12/2017 | Lucisano et al. | |
| 2017/0357776 A1 | 12/2017 | Baker et al. | |
| 2018/0000395 A1 | 1/2018 | Lucisano et al. | |
| 2018/0140239 A1 | 5/2018 | Lucisano et al. | |
| 2018/0153450 A1 | 6/2018 | Routh et al. | |

FOREIGN PATENT DOCUMENTS

| | | |
|---|---|---|
| WO | WO-9213271 A1 | 8/1992 |
| WO | WO-2008013881 A2 | 1/2008 |
| WO | WO-2010002502 A2 | 1/2010 |
| WO | WO-2011018407 A1 | 2/2011 |
| WO | WO-2016014987 A2 | 1/2016 |

OTHER PUBLICATIONS

Alvarez-Icaza M., et al., "Mass Production of Biosensors," Analytical Chemistry, 1993, vol. 65 (11), pp. 525-533.

Anderson J.M., "Biological Responses to Materials." Annual Review of Materials Research, 2001, vol. 31, pp. 81-110.

Armour J.C., et al., "Application of a Chronic intravascular Blood Glucose Sensor in Dogs," Diabetes, 1990, vol. 39 (12), pp. 1519-1526.

Bard A.J., et al., "Electrochemical Methods: Fundamentals and Applications," 2nd Edition, 2000.

Bilitewski U., et al., "Glucose Biosensors Based on Thick Film Technology," Biosensors and Bioelectronics, 1991, vol. 6, pp. 369-373.

Bremer T.M., et al., "Benchmark Data from the Literature for Evaluation of New Glucose Sensing Technologies," Diabetes Technology and therapeutics, 2001, vol. 3 (3), pp. 409-418.

Cha, C.S., et al., "Electrochemical Behaviour of Microfabricated Thick-film Electrodes," Sensors and Actuators B., 1990, vol. 2, pp. 277-281.

Choleau, et al., "Calibration of a Subcutaneous Amperometric Glucose Sensor Implanted for 7 Days in Diabetic Patients Part 2. Superiority of the One-point Calibration Method," Biosensors and Bioelectronics, 2002, vol. 17, pp. 641-646.

Choleau, et al., "Calibration of a Subcutaneous Amperometric Glucose Sensor Part 1. Effect of Measurement Uncertainties on the Determination of Sensor Sensitivity and Background Current.," Biosensors and Bioelectronics, 2002, vol. 17, pp. 647-654.

Conway M.J., et al., "Radio Telemetry of Blood Po2 in Vivo," Biomedical Engineering, 1973, vol. 8 (10), pp. 428-430.

Data Sheet—Platinum Oxygen Sensor Materials, Component Metallizations, OS1/OS2/OS3, Heraeus.

Data Sheet Cermet Platinum Conductor data sheet, 5542 Print Gd, 5542 Pouring GD, Electro-Science Laboratories,Inc.

Data Sheet—4082 and 3804 Platinum Conductors, MEMS Sensor Materials, Ferro Electronic Materials.

Dhakar L., "Skin Based Flexible Triboelectric Nanogenerators with Motion Sensing Capability," Micro Electro Mechanical Systems (MEMS), 2015 28th IEEE International Conference on, 2015, IEEE, pp. 106-109.

Dutronc, P., et al., "Influence of the Nature of the Screen-printed Electrode Metal on the Transport and Detection Properties of Thick-film Semiconductor Gas Sensors," Sensors and Actuators B, 1992, vol. 6, pp. 279-284.

ELISA Kit Manual Human C3a #550499.

ELISA Kit Manual Human C4a #5550947.

Fischer U., et al., "A Membrane Combination for Implantable Glucose Sensors. Measurements in Undiluted Biological Fluids," Transactions—American Society for Artificial Internal Organs, 1982, vol. 28, pp. 245-248.

Golonka L.J., et al., "The influence of the Electrode Material on the Sensitivity of an $Sn_2$ Thick-film Gas Sensor," Sensors and Actuators B, 1994, vol. 18-19, pp. 453-456.

Gough D.A., et al., "A Novel Rotated Disc Electrode and Time Lag Method for Characterizing Mass Transport in Liquid-membrane Systems," Journal of the American Institute of Chemical Engineers, 1980, vol. 26, pp. 1013.

(56) References Cited

OTHER PUBLICATIONS

Gough D.A., et al., "Membrane-covered, Rotated Disc Electrode," Analytical Chemistry, 1979, vol. 51, pp. 439-444.

Gough D.A., et al., "Two-Dimensional Enzyme Electrode Sensor for Glucose," Analytical Chemistry, 1985, vol. 57 (12), pp. 2351-2357.

Gough, et al., "Function of an Implanted Tissue Glucose Sensor for More than 1 Year in Animals", Science Translational Medicine, Jul. 28, 2010, vol. 2 (42), pp. 42ra53.

Holc J., et al., "Interaction Between Thick-film Platinum Electrodes and Yttria-stabilized Zro.sub.2 Ceramic," Journal of Materials Science Letters, 1989, vol. 8, pp. 635-637.

Holmes, et al., Handbook of Thick Film Technology, Electrochemical Publications Ltd (Glasgow: Bell and Bain Ltd., 1976).

Jablecki M., et al., "Simulations of the Frequency Response of Implantable Glucose Sensors," Analytical Chemistry, 2000, vol. 72 (8), pp. 1853-1859.

Kovatchev B.P., et al., "Graphical and Numerical Evaluation of Continuous Glucose Sensing Time Lag," Diabetes Technology Therapeutics, 2009, vol. 11(3), pp. 139-143.

Kroschwitz J., "Concise encyclopedia of polymer science and engineering," John Wiley, 1990, pp. 599-1341.

Lemey S., et al., "Wearable Flexible Lightweight Modular RFID Tag With Integrated Energy Harvester," IEEE Transactions on Microwave Theory and Techniques, 2016, vol. 64.7, pp. 2304-2314.

Leypoldt J.K., et al., "Diffusion and the Limiting Substrate in Two-substrate Immobilized Enzyme Systems," Biotechnology and Bioengineering, 1982, vol. 24 (12), pp. 2705-2719.

Leypoldt J.K., et al., "Model of a Two-substrate Enzyme Electrode for Glucose," Analytical Chemistry, 1984, vol. 56 (14), pp. 2896-2904.

Lucisano, et al., "In Vitro Stability of an Oxygen Sensor," Analytical Chemistry, 1987, vol. 59 (5), pp. 736-739.

Lucisano, Ph.D. Dissertation, Univ. of Calif. (San Diego), pp. xv-xvi, 8-10, 26-30, 34-36, 96-97 (made available to the public on Dec. 15, 1988)—Call No. "T3.6.L821987".

Ma, et al., "A Biocompatible and Biodegradable Protein Hydrogel with Green and Red Autofluorescence: Preparation, Characterization and In Vivo Biodegradation Tracking and Modeling," Scientific Reports (Nature.com) published Jan. 27, 2016.

Makale M.T., et al., "Tissue Window Chamber System for Validation of Implanted Oxygen Sensors," American Journal of Physiology. Heart and Circulatory Physiology, 2003, vol. 284 (6), pp. 2288-2294.

McKean B.D., et al., "A Telemetry-Instrumentation System for Chronically Implanted Glucose and Oxygen Sensors," IEEE Transactions on Biomedical Engineering, 1988, vol. 35 (7), pp. 526-532.

McNaught A.D., et al., "The Compendium of Chemical Terminology," The Gold Book, Second Edition, Blackwell Science, 1997.

Rich A., "Shielding and Guarding," Analog Dialogue, 1983, vol. 17 (1), pp. 8-13.

Sargent B.J., et al., "Design and Validation of the Transparent Oxygen Sensor Array," Biomedical Engineering, IEEE Transactions on, 1991, vol. 38 (5), pp. 476-482.

Schultz J.S., et al., "Optical Fiber Affinity Sensors," Methods in Enzymology, K. Mosbach, Ed., Academic Press, 1988, vol. 137, pp. 349-366.

Takei K., et al., "Design for a 400-MHz Passive RFID Prototype System for Long Range Applications," to be published in Proc. IEEE Int. Symp. Antennas Propag. 2007.

West, Electrodeposition and Corrosion Processes, 1971.

Wong CM., et al., "Glucose Oxidase: Natural Occurrence, Function, Properties and Industrial Applications," Applied Microbiology and Biotechnology, 2008, vol. 78 (6), pp. 927-938.

\* cited by examiner

ANALYTE SENSOR DATA EVALUATION AND ERROR REDUCTION APPARATUS AND METHODS

RELATED APPLICATIONS

This application is related to co-owned and co-pending U.S. patent application Ser. No. 13/559,475 filed Jul. 26, 2012 entitled "Tissue Implantable Sensor With Hermetically Sealed Housing," Ser. No. 14/982,346 filed Dec. 29, 2015 and entitled "Implantable Sensor Apparatus and Methods", Ser. No. 15/170,571 filed Jun. 1, 2016 and entitled "Biocompatible Implantable Sensor Apparatus and Methods", Ser. No. 15/197,104 filed Jun. 29, 2016 and entitled "Bioadaptable Implantable Sensor Apparatus and Methods", Ser. No. 15/359,406 filed Nov. 22, 2016 and entitled "Heterogeneous Analyte Sensor Apparatus and Methods", Ser. No. 15/368,436 filed Dec. 2, 2016 and entitled "Analyte Sensor Receiver Apparatus and Methods", and Ser. No. 15/472,091 filed Mar. 28, 2017 and entitled "Analyte Sensor User Interface Apparatus and Methods," each of the foregoing incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

1. Technical Field

The disclosure relates generally to the field of data analysis and processing, including for sensors, therapy devices, implants and other devices (such as those which can be used consistent with human beings or other living entities for in vivo detection and measurement or delivery of various solutes), and in one exemplary aspect to methods and apparatus enabling the use of such sensors and/or electronic devices for, e.g. monitoring of one or more physiological parameters, including through use of error identification, analysis, and/or correction routines or computer programs to enhance the accuracy and reliability of such physiological parameter measurements.

2. Description of Related Technology

Implantable electronics is a rapidly expanding discipline within the medical arts. Owing in part to significant advances in electronics and wireless technology integration, miniaturization, performance, and material biocompatibility, sensors or other types of electronics which once were beyond the realm of reasonable use within a living subject (i.e., in vivo) can now be surgically implanted within such subjects with minimal effect on the recipient subject, and in fact convey many inherent benefits.

One particular area of note relates to blood analyte monitoring for subjects, such as for example glucose monitoring for those with so-called "type 1" or "type 2" diabetes. As is well known, regulation of blood glucose is impaired in people with diabetes by: (1) the inability of the pancreas to adequately produce the glucose-regulating hormone insulin; (2) the insensitivity of various tissues that use insulin to take up glucose; or (3) a combination of both of these phenomena. Safe and effective correction of this dysregulation requires blood glucose monitoring.

Currently, glucose monitoring in the diabetic population is based largely on collecting blood by "fingersticking" and determining its glucose concentration by conventional assay. This procedure has several disadvantages, including: (1) the discomfort associated with the procedure, which should be performed repeatedly each day; (2) the near impossibility of sufficiently frequent sampling (some blood glucose excursions require sampling every 20 minutes, or more frequently, to accurately treat); and (3) the requirement that the user initiate blood collection, which precludes warning strategies that rely on automatic early detection. Using the extant fingersticking procedure, the frequent sampling regimen that would be most medically beneficial cannot be realistically expected of even the most committed patients, and automatic sampling, which would be especially useful during periods of sleep, is not available.

Implantable glucose sensors (e.g., continuous glucose monitoring sensors) have long been considered as an alternative to intermittent monitoring of blood glucose levels by the fingerstick method of sample collection. These devices may be fully implanted, where all components of the system reside within the body and there are no through-the-skin (i.e. percutaneous) elements, or they may be partially implanted, where certain components reside within the body but are physically connected to additional components external to the body via one or more percutaneous elements. Further, such devices provide users a great deal of freedom from potentially painful intermittent sampling methods such as "fingersticking." as well as having to remember and obtain self-administered blood analyte readings.

The accuracy of blood analyte detection and measurement is an important consideration for implanted analyte sensors, especially in the context of current blood glucose monitoring systems (such as e.g., fully implanted blood glucose sensor systems), and even the future development of implantable blood glucose monitoring systems (such as e.g., in support of the development of an artificial pancreas). Hence, ensuring accurate measurement for extended periods of time (and minimizing the need for any other confirmatory or similar analyses) is of great significance. In conventional sensors, accuracy can be adversely affected by a myriad of factors such as e.g., random noise, foreign body response (FBR), other tissue responses, anoxia or hypoxia in the region of the analyte sensor, blood analyte tissue dynamics, mechanical jarring, and/or other variables.

Sensor error due to such factors can be expressed by the mean absolute relative difference (MARD) between the sensor output and a set of comparison measurements (i.e., a reference measurement), or by the frequency of outliers in the comparison. In one example, the relationship between a measured blood analyte level and a reference blood analyte level (taken at a corresponding point in time) can be expressed by Equation (1) below:

$$BA_{ref} = BA_{cal} - BA_{error} - e \qquad \text{Eqn. (1)}$$

In Equation (1), "$BA_{ref}$" is a blood analyte level measured using an external source, "$BA_{cal}$" is a blood analyte level measured by a calibrated implanted sensor, "$BA_{eror}$" is systematic error due to unmodeled (and possibly user-specific) system variables, and "e" is error due to random noise.

Many known sensor systems include mechanisms and/or programming for signal processing to reduce signal error due to random noise. For example, random noise error is primarily caused by random fluctuations in electrical signals received and/or produced by the sensor components, which can be modeled and/or approximated prior to implantation. Thus, random noise can be reduced via application of one or more standardized signal filters (such as e.g., finite impulse response (FIR), infinite impulse response (IIF), Kalman, Bayesian, and/or other signal processing filters) to the raw or calculated signal data. Accordingly, conventional sensor systems are often pre-programmed for application of random noise signal filters which are implemented during operation (i.e., analyte detection and reporting) of the implanted sensor system. FIG. 1 shows a typical method 100 (generalized) for operation of a conventional implantable analyte sensor. See e.g., U.S. patent application Ser. No. 13/742,694 entitled "Systems and Methods For Providing Sensitive and Specific Alarms."

However, "unmodeled" system variables (e.g., variables which are user and/or context-dependent, and hence may behave differently in each individual and/or context of measurement) present a particularly difficult challenge in determining and maintaining the accuracy of blood analyte measurements in an implanted sensor system. For instance, some analyte detection variables may be user-specific or context-specific based on factors such as, inter alia, disease presentation, anatomy, physiology, metabolism or metabolic rate, medications, diet, activities, habits, climate or geographic region of residence, altitude, lifestyle of the user and/or errors introduced via an imperfect calibration of the sensor. As the foregoing unmodeled system variables primarily affect analyte detection by implanted sensor systems in vivo (and may be highly variable or dynamic in nature), it is nearly impossible to pre-program or adapt a conventional sensor system with standardized mechanisms to account for such variables prior to implantation. While algorithms exist that are utilized for predicting a future blood glucose measurement, assuming the current measurements to be accurate, in order to predict the likelihood of hypoglycemia/hyperglycemia (see e.g., U.S. patent application Ser. No. 14/659,500 entitled "Glycemic Urgency Assessment and Alerts Interface," and Ser. No. 14/720,668 entitled "Systems And Methods For Dynamically And Intelligently Monitoring A Host's Glycemic Condition After an Alert is Triggered"), these approaches in no way seek to (or actually) improve the accuracy of blood glucose measurements in real-time.

The Assignee hereof has recently developed improved methods and apparatus for implanting and measuring blood glucose level; see, inter alia, U.S. patent application Ser. Nos. 13/559,475, 14/982,346, 15/170,571, 15/197,104, 15/359,406, 15/368,436, and 15/472,091 previously incorporated herein. However, the Assignee has further recognized that areas of potential improvement over the prior art relate to, inter alia, providing an implanted analyte sensor system configured for improved accuracy of blood analyte level detection and reporting such as via e.g., in vivo adaptation to and/or modeling of the aforementioned unmodeled system variables.

For example, although conventional implantable sensor systems provide logic or programming to reduce error due to random noise, such blood analyte detection systems do not allow for correction of error due to unmodeled variables of the type previously described (i.e., user- and/or context-specific variables), which is highly desirable in that disease presentation, physiology, lifestyle, etc. may be different for each user, and may also dynamically change as a function of time or in response to a specific event occurring to or within the user.

Accordingly, there is a salient need for more "intelligent" and user-specific adaptable methods and apparatus for in vivo determination of error due to unmodeled system variables and improved accuracy of blood analyte level calculation, and improvement of sensor and blood analyte measurement accuracy.

SUMMARY

The present disclosure satisfies the foregoing needs by providing, inter alia, improved apparatus (including an implanted sensor and associated logic) and methods, for accurately providing information relating to sensed analyte levels, including for example accounting or correcting for signal error due to one or more unmodeled variables within a living subject, for extended periods of time and without requiring explant of the sensor.

In a first aspect, an apparatus for use with an implantable blood analyte sensor apparatus is disclosed. In one embodiment, the apparatus includes data processing apparatus configured for data communication with an analyte sensor apparatus; and a storage apparatus in data communication with the processing apparatus. In one variant, the storage apparatus comprises a computer program which, when executed, causes the data processing apparatus to: (i) cause operation of the blood analyte sensor apparatus in an initial training mode; (ii) based at least in part on the operation of the sensor apparatus in the initial training mode, cause generation of an error correction operational model; and (iii) subsequent to generation of the error correction operational model, cause operation of the analyte sensor apparatus in a detection mode, the detection mode comprising application of the error correction operational model on blood analyte signal data generated by the sensor apparatus so as to correct or compensate for one or more error sources.

In varying implementations, the apparatus is disposed (i) on the sensor apparatus and integrated therewith; (ii) on a receiver apparatus disposed external to a user within which the sensor apparatus is implanted; or (iii) on the sensor apparatus and the causation of generation of the error correction operational model comprises transmission of data collected via the sensor apparatus during the training mode via a wireless interface of the sensor apparatus to an external receiver, the external receiver configured to perform the generation of the model; and the application of the generated error correction model on the signal data comprises application of model data received via the wireless interface from the external receiver.

In one variant of the apparatus, the implanted analyte sensor includes a glucose sensor (part of a so-called "continuous glucose monitor" or CGM), and the analyte signal data are blood glucose concentration data. In one implementation, the glucose sensor is an oxygen-based glucose sensor. In another implementation, the glucose sensor is a hydrogen peroxide-based glucose sensor. In yet another implementation, the glucose sensor includes both a hydrogen peroxide-based sensor and oxygen-based glucose sensor.

In another variant of the apparatus, the operation of the apparatus in the initial training mode includes: (i) receipt of time-stamped blood analyte reference data; and (ii) collection of time-stamped calculated blood analyte sensor data. The initial training mode optionally further comprises collection of time-stamped data derived from one or more ancillary sensors.

In another implementation, the operation of the apparatus in the initial training mode includes a determination that a training data collection threshold has been met; and in response to the determination, termination of the training mode operation. For example, the training data collection threshold may comprise a pre-determined number of data points, and/or a pre-determined duration of time.

In yet another variant of the apparatus, the generation of the error correction operational model includes: (i) generation of blood analyte error data via calculation of a blood analyte error value at each of a plurality of corresponding time points from the time-stamped blood analyte reference data and the time-stamped calculated blood analyte data; (ii) application of one or more mathematical models on at least the blood analyte error data and data related to one or more other parameters; (iii) identification of at least one of the one or more other parameters which has a high correlation to the blood analyte error data; and (iv) utilization of the identified at least one of the one or more other parameters, at least one of the one or more mathematical models, and the blood analyte error data to generate the error correction operational model.

In one implementation, the data related to one or more other parameters includes data related to: (i) one or more times of day; (ii) data related to one or more blood analyte sensor elements from which blood analyte data originated; and/or (iii) data related to one or more ranges of blood analyte concentration.

In yet another implementation, the data related to one or more other parameters includes data contemporaneously collected from one or more other sensors such as e.g., a pressure sensor and/or a temperature sensor. In another example, the one or more other sensors comprise at least a different blood analyte sensor, such as for detection of another blood analyte.

In yet another variant of the apparatus, the operation of the apparatus in the detection mode further includes: (i) collection of the current blood analyte signal data; (ii) processing of the current blood analyte signal data via the application of the error correction operational model; (iii) generation of a corrected blood analyte level based at least on the processed current blood analyte level; and (iv) output of the corrected blood analyte level.

In yet another variant of the apparatus, the computer program is further configured to, when executed, cause the data processing apparatus to determine that one or more subsequent training mode criteria are met. In one implementation, the determination includes a determination that current error data are greater than a pre-determined error threshold, and/or that a time elapsed after the initial training mode is greater than a pre-determined time threshold.

In another aspect of the disclosure, a method of monitoring a blood analyte level of a living being using a blood analyte sensing apparatus is disclosed. In one embodiment, the method includes: (i) operating the blood analyte sensing apparatus in an initial training mode; (ii) based at least in part on the operating in the initial training mode, generating an error correction operational model; and (iii) subsequent to generating the error correction operational model, operating the blood analyte sensing apparatus in a detection mode, the operating in the detection mode including applying the error correction operational model on at least a portion of current blood analyte signal data.

In one variant of the method, the operational model is applied post hoc to previously collected blood analyte data so as to correct it for one or more errors.

In another variant of the method, the training mode is performed, and operational model are applied, periodically while the sensing apparatus is implanted in vivo.

In a further aspect of the disclosure, a method of re-training an implanted sensor apparatus in vivo is disclosed. In one embodiment, the method includes: (i) operating the blood analyte sensing apparatus in an initial training mode; (ii) based at least in part on the operating in the initial training mode, generating an error correction operational model; (iii) subsequent to generating the error correction operational model, substituting the generated model for a prior model within the sensor apparatus, and (iv) using the generated and substituted model on at least a portion of current blood analyte signal data. In one variant, the method further includes post hoc processing of prior generated data using the generated and substituted model, so as to correct the prior data as compared to the prior model.

In yet another aspect of the disclosure, a method of correcting a monitored blood analyte level of a living being, using a blood analyte sensing system, is disclosed. In one embodiment, the method includes: (i) receiving blood analyte reference data from an external source; (ii) collecting calculated blood analyte sensor data from an at least partly implanted blood analyte sensor apparatus, the blood analyte reference data and the calculated blood analyte sensor data comprising a set of training data; (iii) determining that a training data threshold has been met; (iv) based on the determining, generating blood analyte error data; (v) analyzing, via one or more mathematical models, at least the blood analyte error data and the calculated blood analyte sensor data to determine one or more parameters which are correlated with the blood analyte error data; (vi) based on the analyzing, generating an error correction operational model; (vii) subsequent to generating the operational model, detecting a current blood analyte level and applying the operational model on the current blood analyte level to produce a corrected current blood analyte level; and (viii) outputting the corrected current blood analyte level.

In one variant, the blood analyte reference data and calculated blood analyte sensor data are each time-referenced (e.g., time stamped), and the generating blood analyte error data comprises calculating a blood analyte error value at each of a plurality of corresponding time points from the time-stamped blood analyte reference data and the time-stamped calculated blood analyte data.

In another variant of the method, the method further includes collecting time-stamped other sensor data from one or more other sensor apparatus, the set of training data further comprising the other sensor data. In the foregoing variant, the analyzing includes analyzing, via the one or more mathematical models, the other sensor data to determine the one or more parameters which are correlated with the blood analyte error data.

In another aspect, a computer readable apparatus is disclosed. In one embodiment, the computer readable apparatus comprises a storage medium (e.g., magnetic, solid state, optical, or other storage medium) having at least one computer program disposed thereon and readable by a computerized apparatus. The at least one computer program includes, in one variant, a plurality of instructions which, when executed on the computerized apparatus, cause operation of one or more blood analyte sensor apparatus in a training mode, prior to operating the one or more apparatus in an analyte detection mode. Operation in the training mode enables generation of one or more user-specific operational models (via e.g., "machine learning"), which can be used to at least partially correct for systemic or other errors during analyte detection in the detection mode.

In another aspect, a method of operating an implanted blood analyte sensor is disclosed. In one embodiment, the implanted blood analyte sensor is subject to one or more sources of systematic error, and the method includes: obtaining first blood analyte data using the sensor, the obtained data subject to the one or more sources of error; obtaining reference data not subject to the one or more sources of error; evaluating the obtained blood analyte data and the reference data using one or more machine learning algorithms; generating an operational error correction model based at least on the evaluating; and applying the generated model to second blood analyte data to correct for at least one of the one or more sources of error.

In one variant, the method does not require identification or human understanding of one or more physical or physiologic mechanisms causing the at least one of the one or more sources of error.

In yet another aspect, a method of compensating for or correcting errors caused at least in part by unknown or poorly understood mechanisms or sources is disclosed.

In yet another aspect of the disclosure, a computerized network apparatus is disclosed. In one embodiment, the network apparatus includes a cloud-based server apparatus configured to store, and optionally analyze, blood analyte data for a population of users (e.g., persons with at least partly implanted blood analyte sensors, and/or their caregivers).

In still another aspect of the disclosure, a portable electronic apparatus is disclosed. In one embodiment, the portable electronic apparatus includes a portable receiver device configured to train an implanted blood analyte sensor via, inter alia, wireless data communication therewith.

Other features and advantages of the present disclosure will immediately be recognized by persons of ordinary skill in the art with reference to the attached drawings and detailed description of exemplary embodiments as given below.

Figure 1:
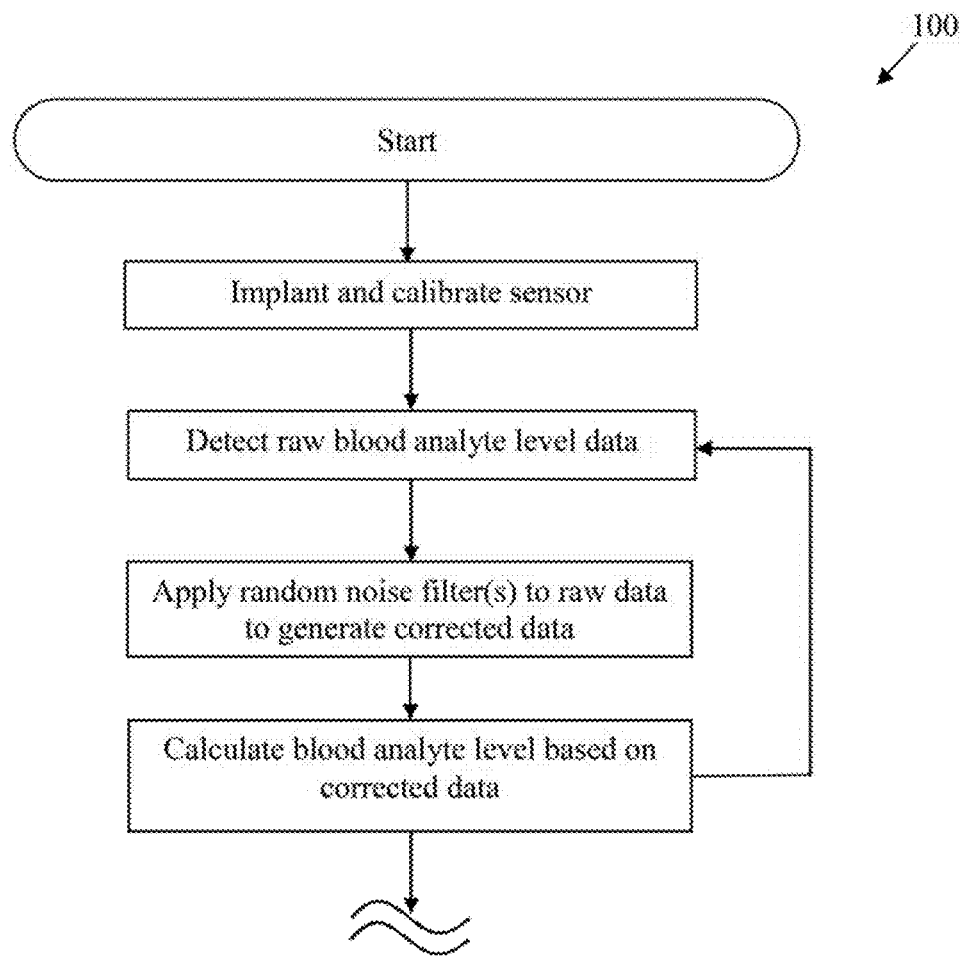
FIG. 1 is a logical flow diagram illustrating a typical prior art method for operating an at least partly implantable blood analyte monitoring system.

All Figures © Copyright 2016-2017 GlySens Incorporated. All rights reserved.

DETAILED DESCRIPTION

Reference is now made to the drawings, wherein like numerals refer to like parts throughout.

Overview One aspect of the present disclosure leverages Assignee's recognition that many of the above-described disabilities of the prior art in providing accurate blood analyte data are due to a lack of an ability to account or correct for "unmodeled" variable errors in calculation and output of blood analyte level. Further, the Assignee hereof recognizes that error in a blood analyte sensor signal due to such unmodeled variables is often user-specific and/or only determinable in vivo (i.e., after implantation of the sensor). Such disabilities of the prior art can be mitigated or even completely eliminated via personalized and dynamic detection of blood analyte level and compensation for associated errors, including when the sensor is implanted within the user.

Accordingly, the apparatus and methods of the present disclosure, in one exemplary embodiment, employ (i) a training mode of operation, whereby the apparatus (or processing logic associated therewith, whether on-board or off-board) conducts "machine learning" to model one or more errors (e.g., unmodeled variable system errors) associated with the blood analyte measurement process, and (ii) generation of an operational model (based at least in part on data collected/received in the training mode), which is applied to correct or compensate for the errors during normal operation and collection of blood analyte data.

The methods and apparatus of the present disclosure also, in one embodiment, leverage the only recently-available capability for long-term implantation of blood analyte sensing devices (such as the oxygen-based blood glucose sensing device manufactured by the Assignee hereof), to yet further enhance device signal stability and accuracy over extended periods of implantation, including through "personalization" of the sensor apparatus via the aforementioned training mode and subsequent operational model generation.

In one embodiment, the aforementioned implantable sensor (e.g., an oxygen-based sensor for detection of blood glucose level) is used in conjunction with either a local receiver apparatus (e.g., a wearable local receiver apparatus) in data communication with a parent platform (e.g., a user's mobile device), or a dedicated receiver and processor apparatus. The sensor and/or the receiver apparatus are configured for operation in a "training mode" after implantation of the sensor. During operation in the "training mode", the sensor system collects in one implementation and calculates time-stamped blood analyte level data ($BA_{cal}$ data), and receives external time-stamped blood analyte level reference data ($BA_{ref}$ data) such as e.g., blood analyte data obtained from "fingersticking", or other laboratory or in situ testing. The system may additionally collect and utilize other non-$BA_{cal}$ data, such as e.g., data collected from each of the other sensors, non-$BA_{cal}$ data collected from the implanted sensor, and/or data input by a user or medical professional.

After collection of a statistically relevant amount of data, the blood analyte reference data and the calculated blood analyte level data are utilized to calculate blood analyte error data ($BA_{error}$ data), and one or more parameters (e.g., time of day, range of the target blood analyte concentration, temperature, sensor element or origin, heart rate, motion, pressure exerted on the implanted sensor, other blood analyte concentrations, other sensor detector signals or features thereof, such as for example first or second derivatives of sensor signals, or measures of sensor signal variability) which have a high correlation to blood analyte error are identified via application of one or more "machine learning algorithms." This information is used in one embodiment to generate a user-specific operational model, which is subsequently used during normal operation of the sensor system in an analyte detection and reporting mode to predict error due to unmodeled system variables (i.e., user and/or context-specific variables). Thus, the output blood analyte level readings advantageously account and/or correct for the predicted unmodeled variable error (and, in some examples, random noise error), thereby providing significantly improved accuracy in terms of, e.g., mean absolute relative difference (MARD) between the sensor output and a comparison or calibrated measurement, or by the frequency of outliers in such comparisons or calibrations, as compared to conventional implantable blood analyte sensor systems.

In another embodiment, the machine learning or training is conducted without reference to external data or ancillary sensor data; i.e., based only on the generated sensor data itself, and analysis thereof.

Moreover, exemplary embodiments of the methods and apparatus disclosed herein need not have any fundamental or even basic knowledge of the mechanism(s) underlying the unmodeled variables/errors; rather, the system can advantageously identify, model and compensate for such errors without having to understand how or why the errors occur (such as in the case of a poorly understood or previously unknown physiologic phenomenon occurring within the target user).

Additionally, the foregoing sensor training mode can be repeated (as necessary, on a prescribed schedule, or according to yet other basis) to maintain sensor accuracy throughout the implantation lifetime, even as disease presentation or other physiological or lifestyle characteristics of the user change over that same time.

Methods of use of the aforementioned blood analyte detection system, as well as other aspects, are also disclosed herein.

Detailed Description of Exemplary Embodiments

Exemplary embodiments of the present disclosure are now described in detail. While these embodiments are primarily discussed in the context of a fully implantable glucose sensor, such as those exemplary embodiments described herein, and/or those set forth in U.S. Patent Application Publication No. 2013/0197332 filed Jul. 26, 2012 entitled "Tissue Implantable Sensor With Hermetically Sealed Housing;" U.S. Pat. No. 7,894,870 to Lucisano et al. issued Feb. 22, 2011 and entitled "Hermetic Implantable Sensor;" U.S. Patent Application Publication No. 2011/0137142 to Lucisano et al. published Jun. 9, 2011 and entitled "Hermetic Implantable Sensor;" U.S. Pat. No. 8,763,245 to Lucisano et al. issued Jul. 1, 2014 and entitled "Hermetic Feedthrough Assembly for Ceramic Body;" U.S. Patent Application Publication No. 2014/0309510 to Lucisano et al. published Oct. 16, 2014 and entitled "Hermetic Feedthrough Assembly for Ceramic Body;" U.S. Pat. No. 7,248,912 to Gough et al. issued Jul. 24, 2007 and entitled "Tissue Implantable Sensors for Measurement of Blood Solutes;" and U.S. Pat. No. 7,871,456 to Gough et al. issued Jan. 18, 2011 and entitled "Membranes with Controlled Permeability to Polar and Apolar Molecules in Solution and Methods of Making Same;" and U.S. Patent Application Publication No. 2013/0197332 to Lucisano et al. published Aug. 1, 2013 and entitled "Tissue Implantable Sensor with Hermetically Sealed Housing;" PCT Patent Application Publication No. 2013/016573 to Lucisano et al. published Jan. 31, 2013 and entitled "Tissue Implantable Sensor with Hermetically Sealed Housing," each of the foregoing incorporated herein by reference in its entirety, as well as those of U.S. patent application Ser. Nos. 13/559,475, 14/982,346, 15/170,571, and 15/197,104, 15/359,406, 15/368,436, and 15/472,091 previously incorporated herein, it will be recognized by those of ordinary skill that the present disclosure is not so limited. In fact, the various aspects of the disclosure are useful with, inter alia, other types of implantable sensors and/or electronic devices.

Further, while the following embodiments describe specific implementations of e.g., biocompatible oxygen-based multi-sensor element devices for measurement of glucose, having specific configurations, protocols, locations, and orientations for implantation (e.g., proximate the waistline on a human abdomen with the sensor array disposed proximate to fascial tissue; see e.g., U.S. patent application Ser. No. 14/982,346 filed Dec. 29, 2015 and entitled "Implantable Sensor Apparatus and Methods" previously incorporated herein), those of ordinary skill in the related arts will readily appreciate that such descriptions are purely illustrative, and in fact the methods and apparatus described herein can be used consistent with, and without limitation: (i) in living beings other than humans; (ii) other types or configurations of sensors (e.g., other types, enzymes, and/or theories of operation of glucose sensors, sensors other than glucose sensors, such as e.g., sensors for other analytes such as urea, lactate); (iii) other implantation locations and/or techniques (including without limitation transcutaneous or non-implanted devices as applicable); and/or (iv) devices intended to deliver substances to the body (e.g. implanted drug pumps); and/or other devices (e.g., non-sensors and non-substance delivery devices).

As used herein, the term "analyte" refers without limitation to a substance or chemical species that is of interest in an analytical procedure. In general, the analyte itself may or may not be directly measurable, in cases where it is not, a measurement of the analyte (e.g., glucose) can be derived through measurement of chemical constituents, components, or reaction byproducts associated with the analyte (e.g., hydrogen peroxide, oxygen, free electrons, etc.).

As used herein, the terms "detector" and "sensor" refer without limitation to a device having one or more elements (e.g., detector element, sensor element, sensing elements, etc.) that generate, or can be made to generate, a signal indicative of a measured parameter, such as the concentration of an analyte (e.g., glucose) or its associated chemical constituents and/or byproducts (e.g., hydrogen peroxide, oxygen, free electrons, etc.). Such a device may be based on electrochemical, electrical, optical, mechanical, thermal, or other principles as generally known in the art. Such a device may consist of one or more components, including for example, one, two, three, or four electrodes, and may further incorporate immobilized enzymes or other biological or physical components, such as membranes, to provide or enhance sensitivity or specificity for the analyte.

As used herein, the terms "orient," "orientation," and "position" refer, without limitation, to any spatial disposition of a device and/or any of its components relative to another object or being, and in no way connote an absolute frame of reference.

As used herein, the terms "top," "bottom," "side," "up," "down," and the like merely connote, without limitation, a relative position or geometry of one component to another, and in no way connote an absolute frame of reference or any required orientation. For example, a "top" portion of a component may actually reside below a "bottom" portion when the component is mounted to another device (e.g., host sensor).

As used herein the term "parent platform" refers without limitation to any device, group of devices, and/or processes with which a client or peer device (including for example the various embodiments of local receiver described here) may logically and/or physically communicate to transfer or exchange data. Examples of parent platforms can include, without limitation, smartphones, tablet computers, laptops, smart watches, personal computers/desktops, servers (local or remote), gateways, dedicated or proprietary analyte receiver devices, medical diagnostic equipment, and even other local receivers acting in a peer-to-peer or dualistic (e.g., master/slave) modality.

As used herein, the term "application" (or "app") refers generally and without limitation to a unit of executable software that implements a certain functionality or theme. The themes of applications vary broadly across any number of disciplines and functions (such as on-demand content management, e-commerce transactions, brokerage transactions, home entertainment, calculator etc.), and one application may have more than one theme. The unit of executable software generally runs in a predetermined environment; for example, the Java® environment.

As used herein, the term "computer program" or "software" is meant to include any sequence or human or machine cognizable steps which perform a function. Such program may be rendered in virtually any programming language or environment including, for example, C/C++, Fortran, COBOL, PASCAL, assembly language, markup languages (e.g., HTML, SGML, XML, VoXML), and the like, as well as object-oriented environments such as the Common Object Request Broker Architecture (CORBA), Java® (including J2ME, Java Beans, etc.) and the like.

As used herein, the terms "Internet" and "internet" are used interchangeably to refer to inter-networks including, without limitation, the Internet. Other common examples include but are not limited to: a network of external servers, "cloud" entities (such as memory or storage not local to a device, storage generally accessible at any time via a network connection, or cloud-based or distributed processing or other services), service nodes, access points, controller devices, client devices, etc.

As used herein, the term "memory" includes any type of integrated circuit or other storage device adapted for storing digital data including, without limitation, ROM, PROM, EEPROM, DRAM, SDRAM, DDR/2 SDRAM, EDO/FPMS, RLDRAM, SRAM, "flash" memory (e.g., NAND/NOR), 3D memory, and PSRAM.

As used herein, the terms "microprocessor" and "processor" or "digital processor" are meant generally to include all types of digital processing devices including, without limitation, digital signal processors (DSPs), reduced instruction set computers (RISC), general-purpose (CISC) processors, microprocessors, gate arrays (e.g., FPGAs), PLDs, state machines, reconfigurable computer fabrics (RCFs), array processors, secure microprocessors, and application-specific integrated circuits (ASICs). Such digital processors may be contained on a single unitary integrated circuit (IC) die, or distributed across multiple components.

As used herein, the term "network" refers generally to any type of telecommunications or data network including, without limitation, hybrid fiber coax (HFC) networks, satellite networks, telco networks, and data networks (including MANs, WANs, LANs, WLANs, internets, and intranets), cellular networks, as well as so-called "mesh" networks and "IoTs" (Internet(s) of Things). Such networks or portions thereof may utilize any one or more different topologies (e.g., ring, bus, star, loop, etc.), transmission media (e.g., wired/RF cable, RF wireless, millimeter wave, optical, etc.) and/or communications or networking protocols.

As used herein, the term "interface" refers to any signal or data interface with a component or network including, without limitation, those of the FireWire (e.g., FW400, FW800, etc.), USB (e.g., USB 2.0, 3.0. OTG), Ethernet (e.g., 10/100, 10/100/1000 (Gigabit Ethernet), 10-Gig-E, etc.), MoCA, LTE/LTE-A, Wi-Fi (802.11), WiMAX (802.16), Z-wave, PAN (e.g., 802.15)/Zigbee, Bluetooth, Bluetooth Low Energy (BLE) or power line carrier (PLC) families.

As used herein, the term "storage" refers to without limitation computer hard drives, memory, RAID devices or arrays, optical media (e.g., CD-ROMs, Laserdiscs, Blu-Ray, etc.), solid state devices (SSDs), flash drives, cloud-hosted storage, or network attached storage (NAS), or any other devices or media capable of storing data or other information.

As used herein, the term "Wi-Fi" refers to, without limitation and as applicable, any of the variants of IEEE-Std. 802.11 or related standards including 802.11 a/b/g/n/s/v/ac or 802.11-2012/2013, as well as Wi-Fi Direct (including inter alia, the "Wi-Fi Peer-to-Peer (P2P) Specification", incorporated herein by reference in its entirety).

As used herein, the term "wireless" means any wireless signal, data, communication, or other interface including without limitation Wi-Fi, Bluetooth (including BLE or "Bluetooth Smart"), 3G (3GPP/3GPP2), HSDPA/HSUPA, TDMA, CDMA (e.g., IS-95A, WCDMA, etc.), FHSS, DSSS, GSM, PAN/802.15, WiMAX (802.16), 802.20, Zigbee®, Z-wave, narrowband/FDMA, OFDM, PCS/DCS, LTE/LTE-A, analog cellular, CDPD, satellite systems, millimeter wave or microwave systems, acoustic, and infrared (i.e., IrDA).

Exemplary Implantable Sensor

Figure 2:
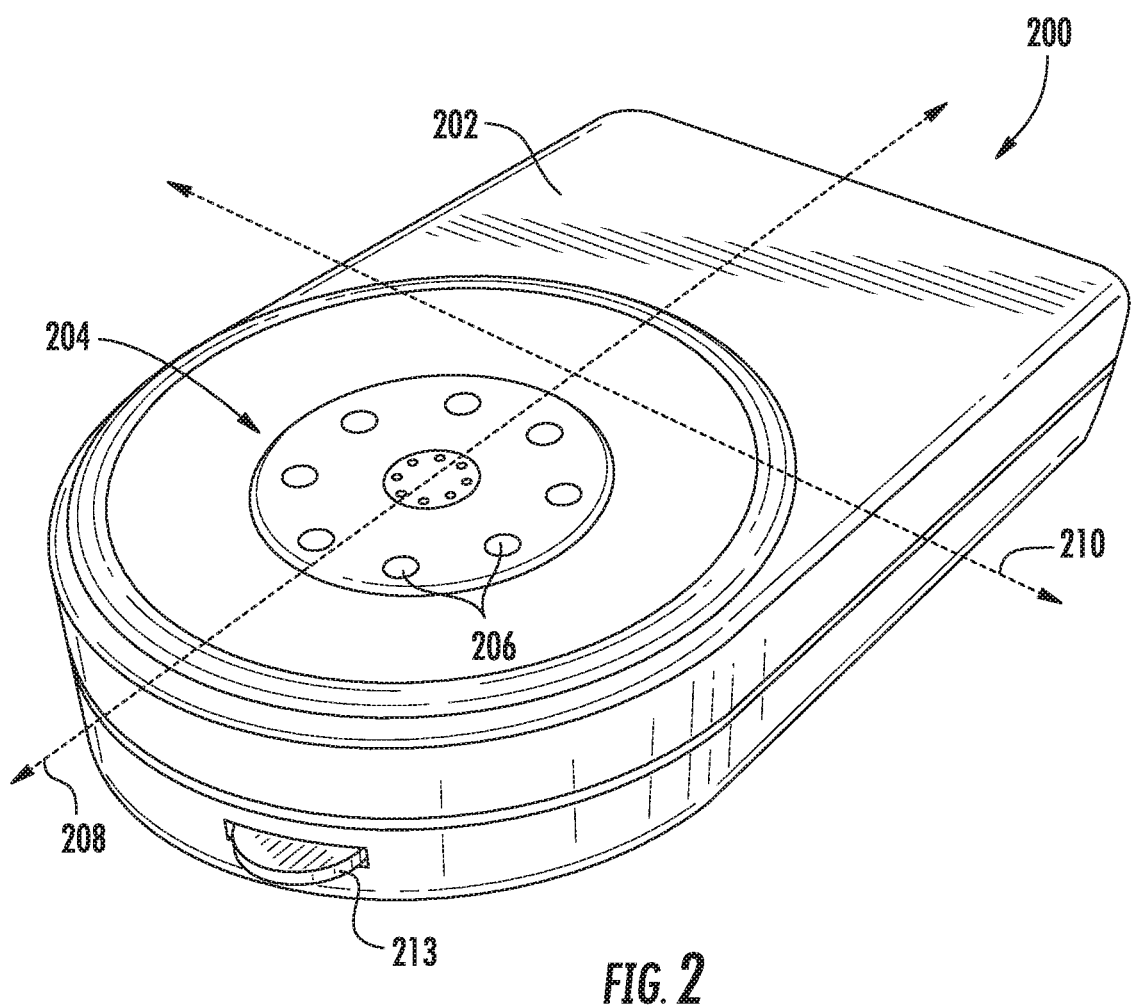
FIG. 2 is a front perspective view of one exemplary embodiment of a fully implantable biocompatible sensor apparatus useful with various aspects of the present disclosure.
Figure 2A:
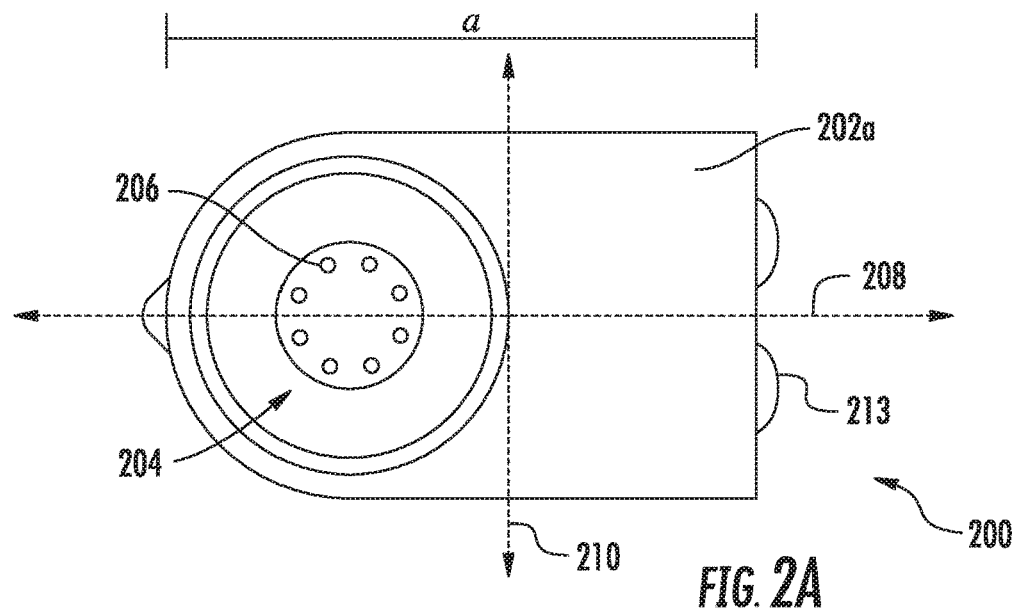
FIGS. 2A-2C are top, bottom, and side elevation views, respectively, of the exemplary sensor apparatus of FIG. 2.
Figure 2B:
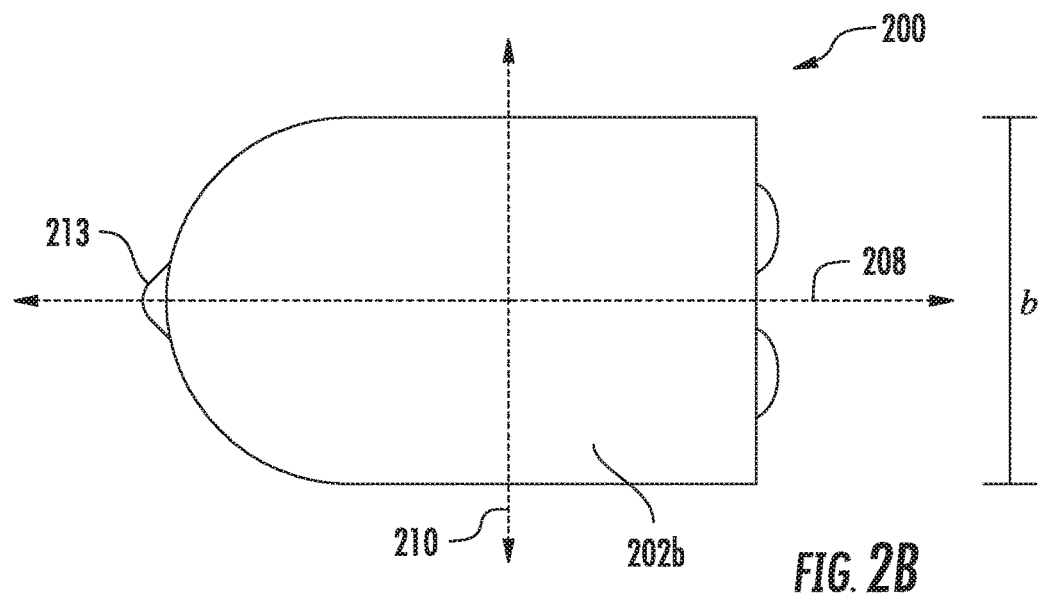
Figure 2C:
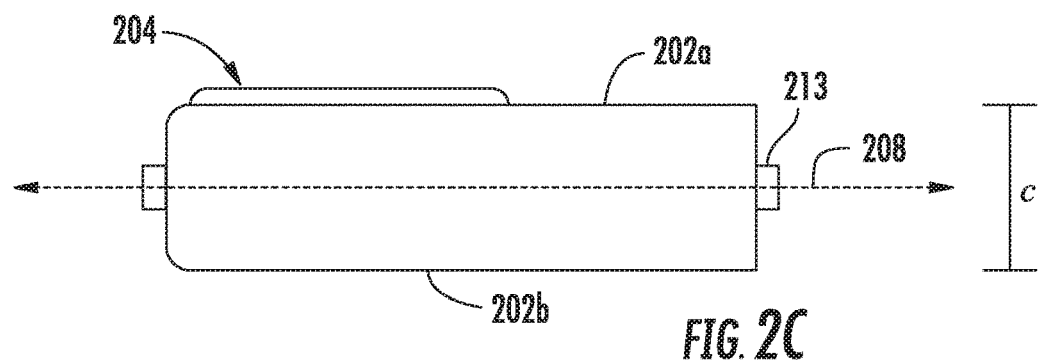

Referring now to FIGS. 2-2C, one exemplary embodiment of a sensor apparatus useful with various aspects of the present disclosure is shown and described.

As shown in FIGS. 2-2C, the exemplary sensor apparatus 200 comprises a somewhat planar housing structure 202 with a sensing region 204 disposed on one side thereof (i.e., a top face 202a). As described in greater detail below with respect to FIGS. 4-5, the exemplary substantially planar shape of the housing 202 provides mechanical stability for the sensor apparatus 200 after implantation, thereby helping to preserve the orientation of the apparatus 200 and mitigate any tissue response induced by movement of the apparatus while implanted. Notwithstanding, the present disclosure contemplates sensor apparatus of shapes and/or sizes other than that of the exemplary apparatus 200.

The sensor apparatus of FIGS. 2-2C further includes a plurality of individual sensor elements 206 with their active surfaces disposed substantially within the sensing region 204 on the top face 202a of the apparatus housing. In the exemplary embodiment (i.e., an oxygen-based glucose sensor), the eight (8) sensing elements 206 are grouped into four pairs, one element of each pair an active or "primary" sensor with enzyme matrix, and the other a reference or "secondary" (oxygen) sensor. Exemplary implementations of the sensing elements and their supporting circuitry and components are described in, inter alia, U.S. Pat. No. 7,248,912, previously incorporated herein. It will be appreciated, however, that the type and operation of the sensor apparatus may vary; i.e., other types of sensor elements/sensor apparatus, configurations, and signal processing techniques thereof may be used consistent with the various aspects of the present disclosure, including, for example, signal processing techniques based on various combinations of signals from individual elements in the otherwise spatially-defined sensing elements pairs.

The illustrated embodiment of FIGS. 2-2C includes a sensing region 204 which facilitates some degree of "interlock" of the surrounding tissue (and any subsequent tissue response generated by the host) so as to ensure direct and sustained contact between the sensing region 204 and the blood vessels of the surrounding tissue during the entire term of implantation (as well as advantageously maintaining contact between the sensing region 204 and the same tissue; i.e., without significant relative motion between the two).

The sensor apparatus 200 also includes in the exemplary embodiment a wireless radio frequency transmitter (or transceiver, depending if signals are intended to be received by the apparatus), not shown. As described in the aforementioned documents incorporated herein, the transmitter/transceiver may be configured to transmit modulated radio frequency signals to an external receiver/transceiver, such as a dedicated receiver device, or alternatively a properly equipped consumer electronic device such as a smartphone or tablet computer. Moreover, the sensor apparatus 200 may be configured to transmit signals to (whether in conjunction with the aforementioned external receiver, or in the alternative) an at least partly implanted or in vivo receiving device, such as an implanted pump or other medication or substance delivery system (e.g., an insulin pump or dispensing apparatus), embedded "logging" device, or other. It is also appreciated that other forms of wireless communication may be used for such applications, including for example inductive (electromagnetic induction) based systems, or even those based on capacitance or electric fields, or even optical (e.g., infrared) systems where a sufficiently clear path of transmission and reception exists, such as two devices in immediately adjacent disposition, or even ultrasonic systems where the two devices are sufficiently close and connected by sound-conductive media such as body tissues or fluids, or a purposely implanted component.

The sensor apparatus of FIGS. 2-2C also includes a plurality (three in this instance) of tabs or anchor apparatus 213 disposed substantially peripheral on the apparatus housing. These anchor apparatus provide the implanting surgeon with the opportunity to anchor the apparatus to the anatomy of the living subject, so as to frustrate translation and/or rotation of the sensor apparatus 200 within the subject immediately after implantation but before any tissue response (e.g., FBR) of the subject has a chance to immobilize (such as via interlock with the sensing region of the apparatus. See e.g., U.S. patent application Ser. No. 14/982, 346 filed Dec. 29, 2015 and entitled "Implantable Sensor Apparatus and Methods" previously incorporated herein, for additional details and considerations regarding the aforementioned anchor apparatus 213 (which may include, for example features to receive sutures (dissolvable or otherwise), tissue ingrowth structures, and/or the like).

Moreover, another exemplary embodiment of the sensor apparatus 200 described herein may include either or both of: (i) multiple detector elements with respective "staggered" ranges/rates of detection operating in parallel, and/or (ii) multiple detector elements with respective "staggered" ranges/rates of detection that are selectively switched on/off in response to, e.g., the analyte concentration reaching a prescribed upper or lower threshold, as described in the foregoing Patent application Ser. No. 15/170,571 previously incorporated herein.

The present disclosure further contemplates that such thresholds or bounds: (i) can be selected independent of one another; and/or (ii) can be set dynamically while the apparatus 300 is implanted. For example, in one scenario, operational detector elements are continuously or periodically monitored to confirm accuracy, and/or detect any degradation of performance (e.g., due to equipment degradation, progressive FBR affecting that detector element, etc.); when such degradation is detected, affecting say a lower limit of analyte concentration that can be detected, that particular detector element can have its lower threshold adjusted upward, such that handoff to another element capable of more accurately monitoring concentrations in that range. Note that these thresholds or bounds are to be distinguished from those associated with the user interface (UI) described subsequently herein, the latter being independent of the data source/capability/configuration associated with the sensor detector elements.

It will be appreciated that the relatively smaller dimensions of the sensor apparatus (as compared to many conventional implant dimensions)—on the order of 40 mm in length (dimension "a" on FIGS. 2A-2C) by 25 mm in width (dimension "b" on FIGS. 2A-2C) by 10 mm in height (dimension "c" on FIGS. 2A-2C)—may reduce the extent of injury (e.g., reduced size of incision, reduced tissue disturbance/removal, etc.) and/or the surface area available for blood/tissue and sensor material interaction, which may in turn reduce intensity and duration of the host wound healing response. It is also envisaged that as circuit integration is increased, and component sizes (e.g., Lithium or other batteries) decrease, and further improvements are made, the sensor may increasingly be appreciably miniaturized, thereby further leveraging this factor.

System Architecture—

As described elsewhere herein, exemplary embodiments of the present disclosure utilize machine learning algorithms to, inter alia, compensate for systemic errors, whether well modeled, or unmodeled, affecting a blood analyte sensor apparatus. Notably, such algorithms may be implemented in computerized logic (software, firmware, or even hardware) that is resident in any number of different locations within the system, including: (i) within the implanted sensor apparatus itself; (ii) "off-board" the sensor apparatus, such as in an external receiver apparatus (examples of which are described below); (iii) off-board, in a connected "cloud" entity; and/or combinations of the foregoing (e.g., in a distributed computing architecture). Accordingly, the following embodiments are merely examples of such types of architectures, and the various aspects of the present disclosure are in no way limited thereto.

Figure 3:
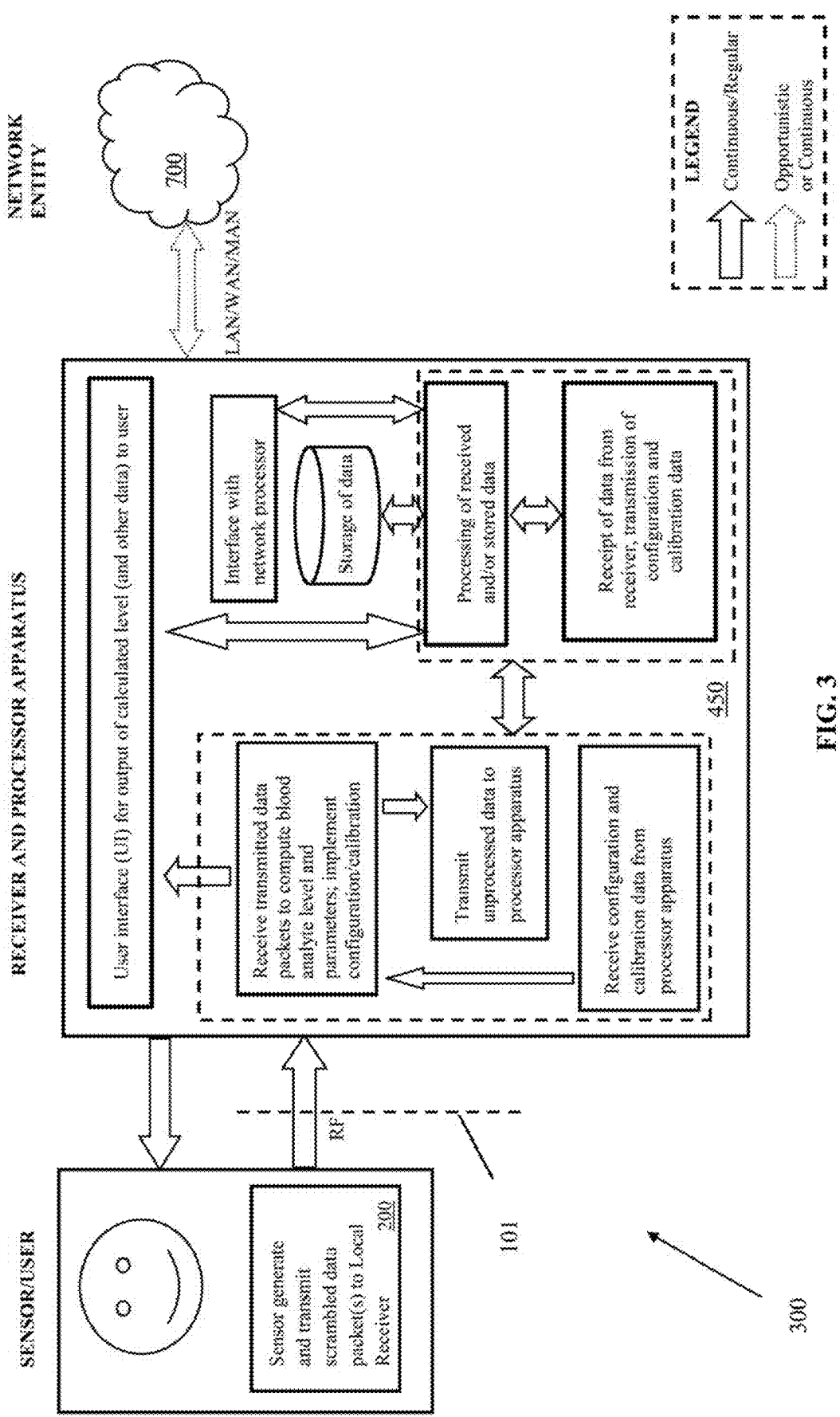
FIG. 3 is a functional block diagram illustrating one embodiment of a system architecture for, inter alia, monitoring blood analyte levels within a user, useful with various aspects of the present disclosure.

Referring now to FIG. 3, one embodiment of a system architecture for, inter alia, monitoring blood analyte levels within a user, useful with the machine learning-based methods and apparatus of present disclosure, is described in detail. As depicted in FIG. 3, the system architecture comprises a sensor apparatus 200 (e.g., that of FIGS. 2-2C discussed above, or yet other types of device) associated with a user, a receiver and processor apparatus 450 and a network entity 700. The sensor apparatus 200 in this embodiment communicates with the receiver and processor apparatus 450 via a wireless interface (described in detail below) through the user's tissue boundary 101. The receiver and processor apparatus 450 may also, if desired, communicate with one or more network entities 800 via a LAN/WLAN, MAN, or other topology, such as for "cloud" data storage, analysis, convenience of access at other locations/synchronization with other user platforms, etc.

Figure 3A:
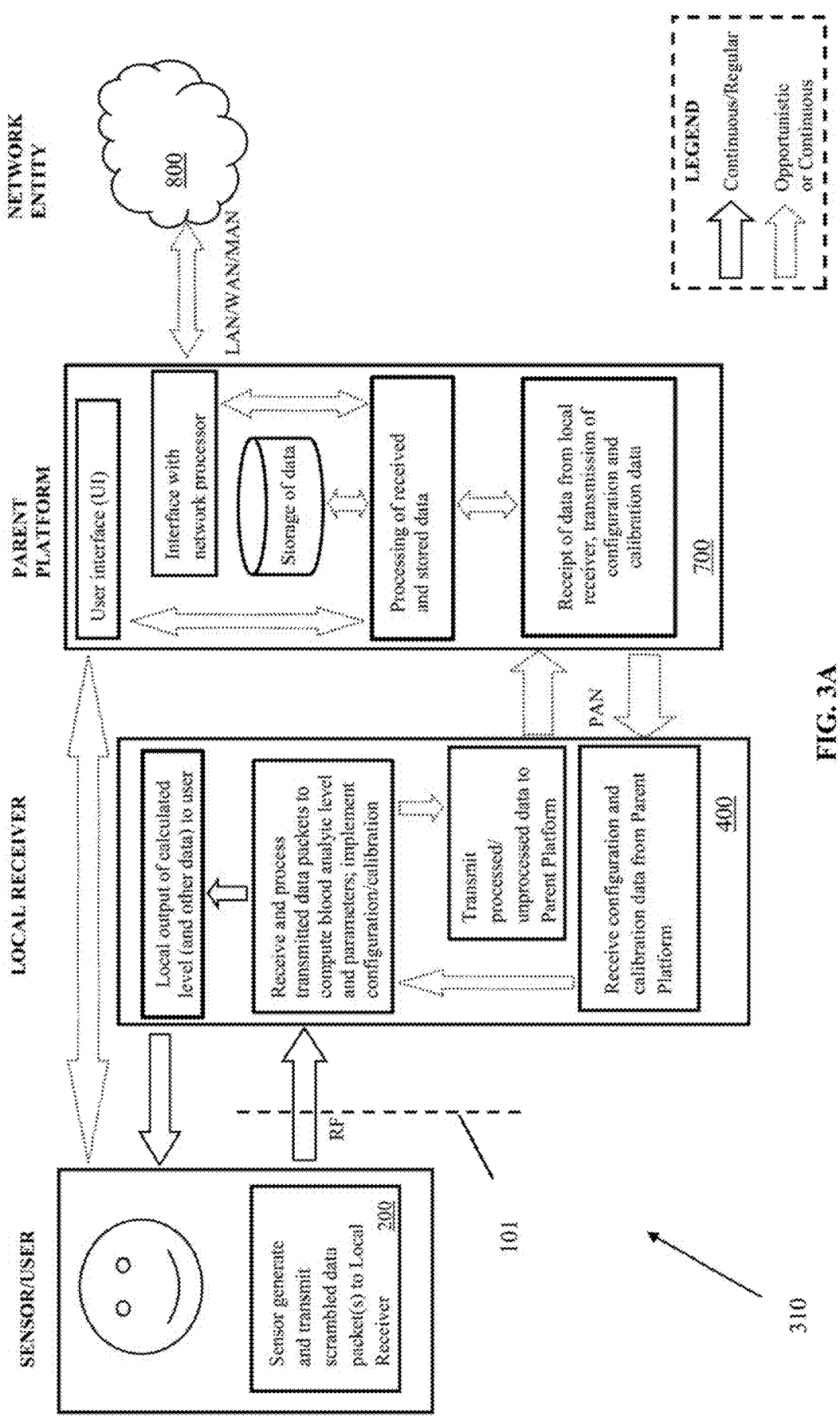
FIG. 3A is a functional block diagram illustrating another embodiment of a system architecture for, inter alia, monitoring blood analyte levels within a user, useful with various aspects of the present disclosure.

As shown in FIG. 3A, another exemplary system architecture 310 comprises a sensor apparatus 200 (e.g., that of FIG. 2 discussed above, or yet other types of device) associated with a user, a local receiver 400, a parent platform 700, and a network entity 800. The sensor apparatus 200 in this embodiment communicates with the local receiver 400 via a wireless interface (described in detail below) through the user's tissue boundary 101. The local receiver 400 communicates (e.g., wirelessly) with the one or more parent platform(s) 600 via a PAN (e.g., Bluetooth or similar) RF interface, as discussed in greater detail below. The parent platform 700 may also, if desired, communicate with one or more network entities 800 via a LAN/WLAN, MAN, or other topology, such as for "cloud" data storage, analysis, convenience of access at other locations/synchronization with other user platforms, etc.

In exemplary system architecture shown in FIG. 3A, the local receiver 400 is a lower profile and/or wearable local receiver apparatus (e.g., small profile wristband, fob, tooth or other implant, skin-adherent patch, ear "bud" or plug, a ring worn in the finger, etc.) as compared to the receiver and processor apparatus 450 shown in FIG. 3. The local receiver apparatus 400 can include a user alert mechanism and/or minimal user interface (UI) such as, e.g., a substantially flat and flexible LED (e.g., graphene-based), AMOLED, or OTFT (organic thin-film transistor) display device, haptic mechanism (e.g., a vibration mechanism), auditory mechanism (e.g., speakers), and/or other user-signaling capabilities and mechanisms (e.g., indicator lights). Various exemplary configurations for the local receiver 400 are shown and described in U.S. patent application Ser. No. 15/368,436 filed Dec. 2, 2016 previously incorporated herein.

As indicated in FIG. 3A, the communications between the sensor 200 and the local receiver 400 are generally continuous and reliable in nature (similar to communication between the sensor 200 and the receiver and processor apparatus 450 of FIG. 3). In contrast, the communication between the local receiver 400 and the parent platform(s) can be either continuous or opportunistic (or any desired combination thereof between the various components of each) in nature. Such opportunistic communication can be a significant advantage of the architecture 300 over the prior art; i.e., the ability for the sensor 200 and a reduced form-factor local receiver 400 to communicate regularly to enable reliable and effectively constant monitoring and user awareness of their blood analyte (e.g., glucose) level, without being "tethered" to larger, bulkier, and perhaps activity-limiting parent devices, including for extended periods of time.

Specifically, in the illustrated architecture 310, the local receiver 400 acts as a reduced- or limited-functionality indicator and monitor for the user that reliably operates for comparatively extended periods of time without external input or calibration, thereby obviating the parent platform during those periods. As described later herein, the reduced form factor advantageously enables the user to further: (i) engage in activities which they could not otherwise engage in if "tethered" to the parent platform, and (ii) effortlessly keep the local receiver with them at all times, and obtain reliable blood analyte data and other useful information (e.g., trend, rate of change (ROC), and other sensor-data derived parameters), in a non-obtrusive (or even covert) manner.

In the example of system architecture 310, when communication between the parent platform 600 and the local receiver does occur, the exemplary architecture 310 enables two-way data transfer, including: (i) transfer of stored data extracted from the sensor wireless transmissions to the local receiver, to the parent platform for archiving, analysis, transfer to a network entity, etc.; (ii) transfer of sensor-specific identification data and/or local receiver-specific data between the local receiver and the parent platform; (iii) transfer of external calibration data (e.g., derived from an independent test method such as a fingerstick or blood glucose monitor and input either automatically or manually to the parent platform) from the parent to the local receiver; and (iv) transfer of local receiver configuration or other data (e.g., software/firmware updates, user-prescribed receiver settings for alarms, warning/buffer values, indication formats or parameters, historical blood analyte levels for the user, results of analysis by the parent 700 or network entity 800 of such data, diagnoses, security or data scrambling/encryption codes or keys, etc.) from the parent 600 to the local receiver 400.

Figure 3B:
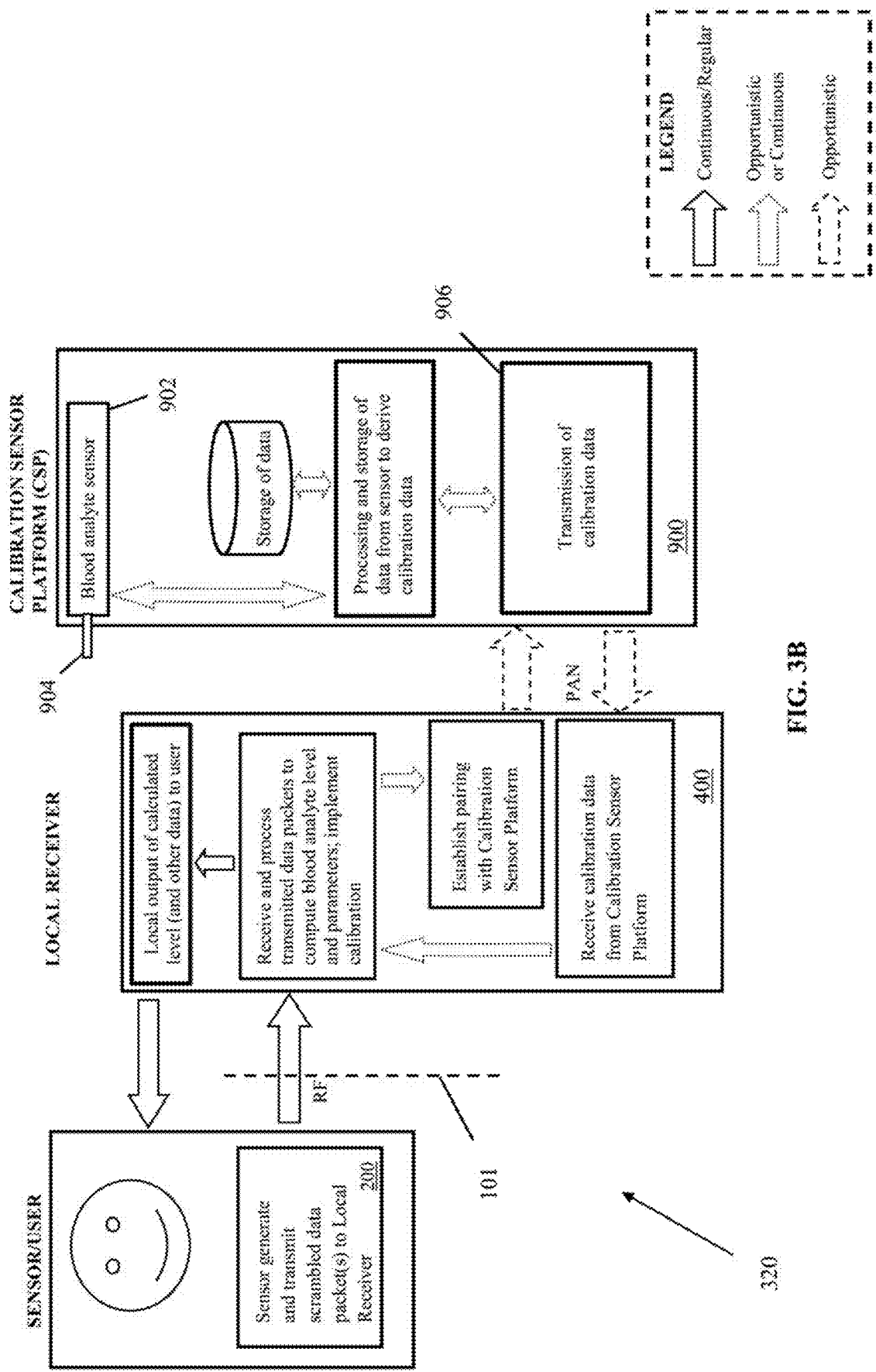
FIG. 3B is a functional block diagram illustrating yet another embodiment of a system architecture for, inter alia, monitoring blood analyte levels within a user, according to the present disclosure.

FIG. 3B shows yet another embodiment of a system architecture 320 for, inter alia, monitoring blood analyte levels within a user, useful with the present disclosure. As shown in FIG. 3B, the architecture 320 comprises a sensor apparatus 200 associated with a user, a local receiver 400, and calibration sensor platform 900. As with the embodiment of FIG. 3A, the sensor apparatus 200 in this embodiment communicates with the local receiver 400 via a wireless interface through the user's tissue boundary 101. The local receiver 400 communicates (e.g., wirelessly) with one or more calibration sensor platform(s) or CSPs 900 via a PAN (e.g., Bluetooth or similar) RF interface, as discussed in greater detail below, or via IR (e.g., IrDA-compliant), optical or other short-range communication modality. As described in greater detail below, the CSP 900 in the illustrated embodiment comprises a calibration data source for the local receiver 400, which may stand in the place of the more fully-functioned parent platform 700 for at least provision of calibration data.

As indicated in FIG. 3B, the communications between the sensor 200 and the local receiver 400 are again generally continuous or regular in nature while the communication between the local receiver 400 and the CSP 900 is purposely opportunistic in nature.

When the opportunistic communication between the CSP 900 and the local receiver does occur, the exemplary architecture 310 enables at least one-way data transfer, including transfer of external calibration data (e.g., derived from an independent test method such as the "fingerstick" or other form of blood analyte sensor 902 of the CSP 900 from the CSP to the local receiver 400. In an exemplary implementation, the CSP 900 comprises a "smart" fingerstick apparatus, including at least (i) sufficient onboard processing capability to generate calibration data useful with the local receiver 400 based on signals or data output from the blood sensor 902, and (ii) a data interface to enable transmission of the data to the local receiver 400. In one configuration, the sensor 902 includes a needle or lancet apparatus 904 which draws a sample of the user's blood for the sensor 902 to analyze. Electronic glucose "fingerstick" apparatus (including those with replaceable single-use lancets) and re-usable electronic components are well known in the relevant arts, and accordingly not described further herein. See e.g., U.S. Pat. No. 8,357,107 to Draudt, et al. issued Jan. 22, 2013 and incorporated herein by reference in its entirety, for one example of such technology. The sensor 902 analyzes the extracted blood obtained via the lancet 904 and (via the onboard processing) produces data indicative of a blood glucose level (or at least generates data from which such level may be derived), such data being provided to the communications interface 906 for transfer to the local receiver 400. The transmitted data are then utilized within the local receiver 400 for calibration of the data generated by the implanted sensor 200.

In one variant, the interface 906 comprises a Bluetooth-compliant interface, such that a corresponding Bluetooth interface of the local receiver can "pair" with the CSP 900 to effect transfer of the calibration data wirelessly. Hence, the user with implanted sensor 200 can simply use a fingerstick-based or other type of external calibration data source to periodically (e.g., once weekly) confirm the accuracy and/or update the calibration of the implanted sensor 200 via opportunistic communication between the local receiver 400 (e.g., small profile wristband, fob, etc.) and CSP 900 when convenient for the user. Advantageously, many persons with diabetes possess such electronic fingerstick-based devices, and wireless communication capability is readily added thereto by the manufacturer at little additional cost.

In another variant, the communications interface comprises an IR or optical "LOS" interface such as one compliant with IrDA technology, such that the user need merely establish a line-of-sight path between the emitter of the CSP 900 and the receptor of the local receiver 400, akin to a television remote control. As yet another alternative, a near-field communication (NFC) antenna may be utilized to transfer data wirelessly between the apparatus 400, 900 when placed in close range (i.e., "swiped"). Yet other communication modalities will be recognized by those of ordinary skill given the present disclosure. Additional functionalities of the local receiver 400 and parent platform 700 are described in U.S. patent application Ser. No. 15/368,436 filed Dec. 2, 2016 and previously incorporated herein.

It will be appreciated that the architectures shown in FIGS. 3-3B are in no way exclusive of one another, and in fact may be used together (such as at different times and/or via different use cases). For example, CSP 900 can be used in combination with receiver and processor apparatus 450 for opportunistic communication of calibration data. Myriad other permutations of use cases involving one or more of the various components 200, 400, 450, 700, 800, 900 are envisaged by the present disclosure. Various system architecture and communication pathways of system components are shown and described in U.S. patent application Ser. No. 15/368,436 filed Dec. 2, 2016 and previously incorporated herein.

Figure 4:
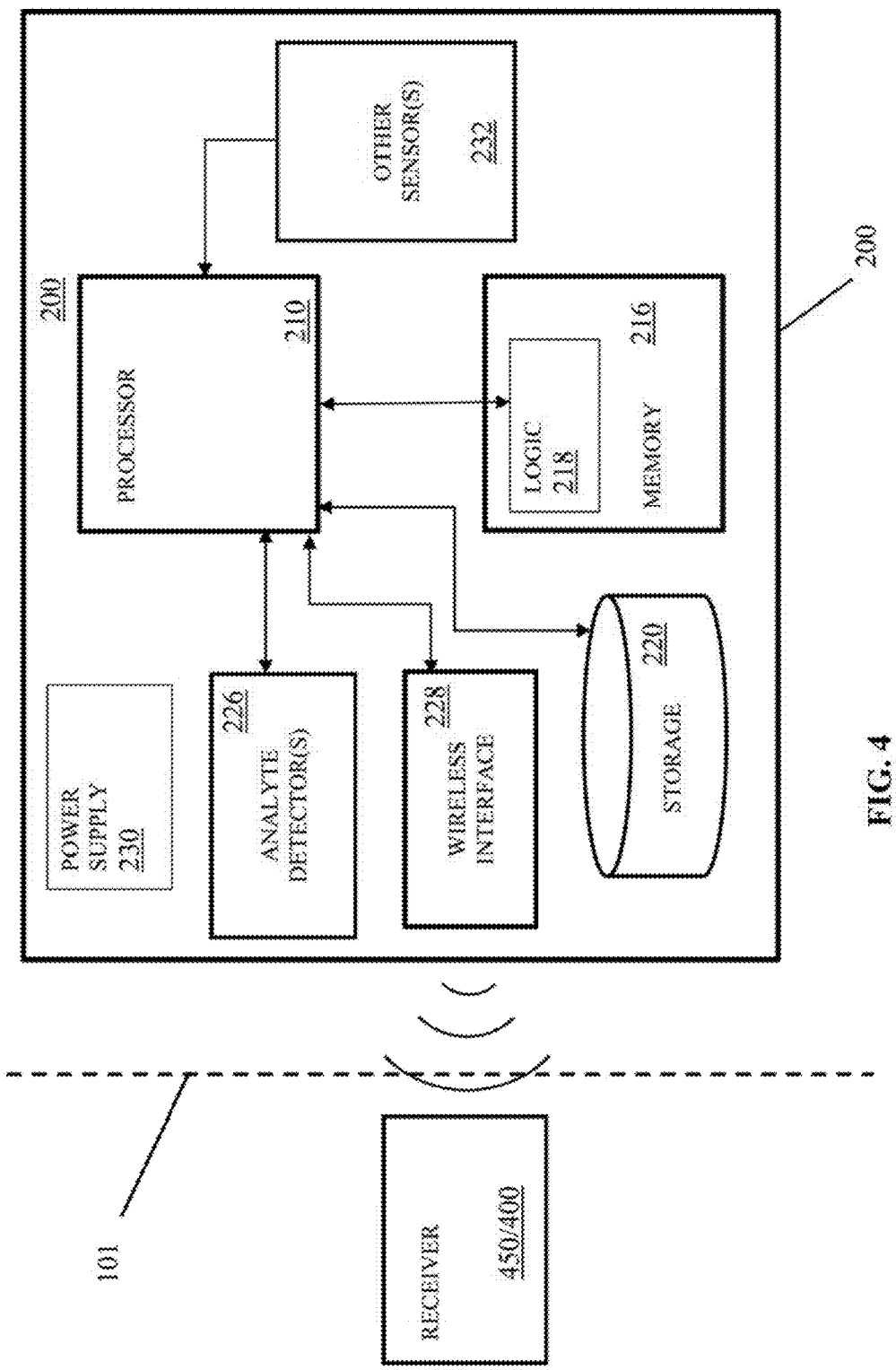
FIG. 4 is a logical block diagram illustrating an exemplary implantable sensor apparatus and local receiver apparatus of FIGS. 3-3B.

FIG. 4 is a functional block diagram illustrating an exemplary implantable sensor apparatus 200 and local receiver and processor apparatus 450 or local receiver apparatus 400 according to one embodiment of the present disclosure. As shown, the sensor apparatus 200 includes a processor 210 (e.g., digital RISC, CISC, and/or DSP device), and/or a microcontroller (not shown), memory 216, software/firmware 218 operative to execute on the processor 210 and stored in e.g., a program memory portion of the processor 210 (not shown), or the memory 216, a mass storage device 220 (e.g., NAND or NOR flash, SSD, etc. to store collected raw or preprocessed data or other data of interest), one or more analyte detectors 226, a wireless interface 228 (e.g., narrowband, PAN such as Bluetooth, or other, described below), a power supply 230 (e.g., a primary Lithium or rechargeable NiMH or Lithium ion battery).

Also depicted in FIG. 4, the sensor apparatus 200 can optionally include one or more additional internal sensors 232. The internal sensor(s) 232 may be any of a temperature sensor, an accelerometer, a pressure sensor, a pulse meter, a conductivity meter, pH (i.e., hydronium ion concentration), electric field sensor, and/or other (non-target) analyte-detection sensors (e.g., other blood analytes). In an alternate embodiment, the one or more internal sensors can be located in a separate implantable apparatus positioned proximate to the sensor 200 during implantation.

As can be appreciated by those of ordinary skill given the present disclosure, any number of different hardware/software/firmware architectures and component arrangements can be utilized for the sensor apparatus 200 of FIG. 4, the foregoing being merely illustrative. For instance, a less-capable (processing, sensing, and/or data storage-wise) or "thinner" configuration may be used (e.g., excluding the one or more additional internal sensors), or additional functionality not shown added (e.g., including additional types of other sensors and/or components).

Receiver Apparatus—

Figure 4A:
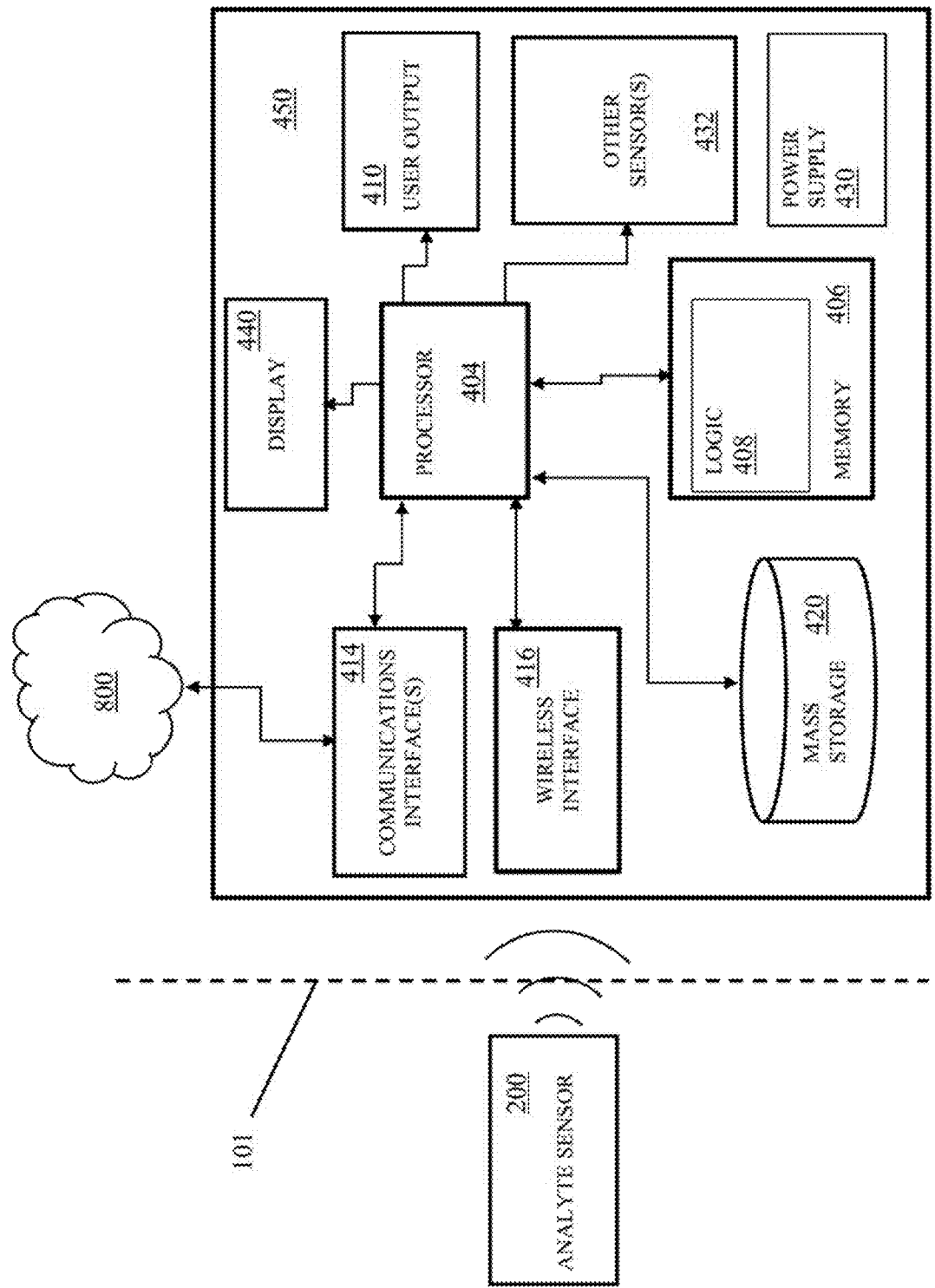
FIG. 4A is a logical block diagram block diagram illustrating an exemplary embodiment of the dedicated receiver and processor apparatus of FIG. 3.
Figure 4B:
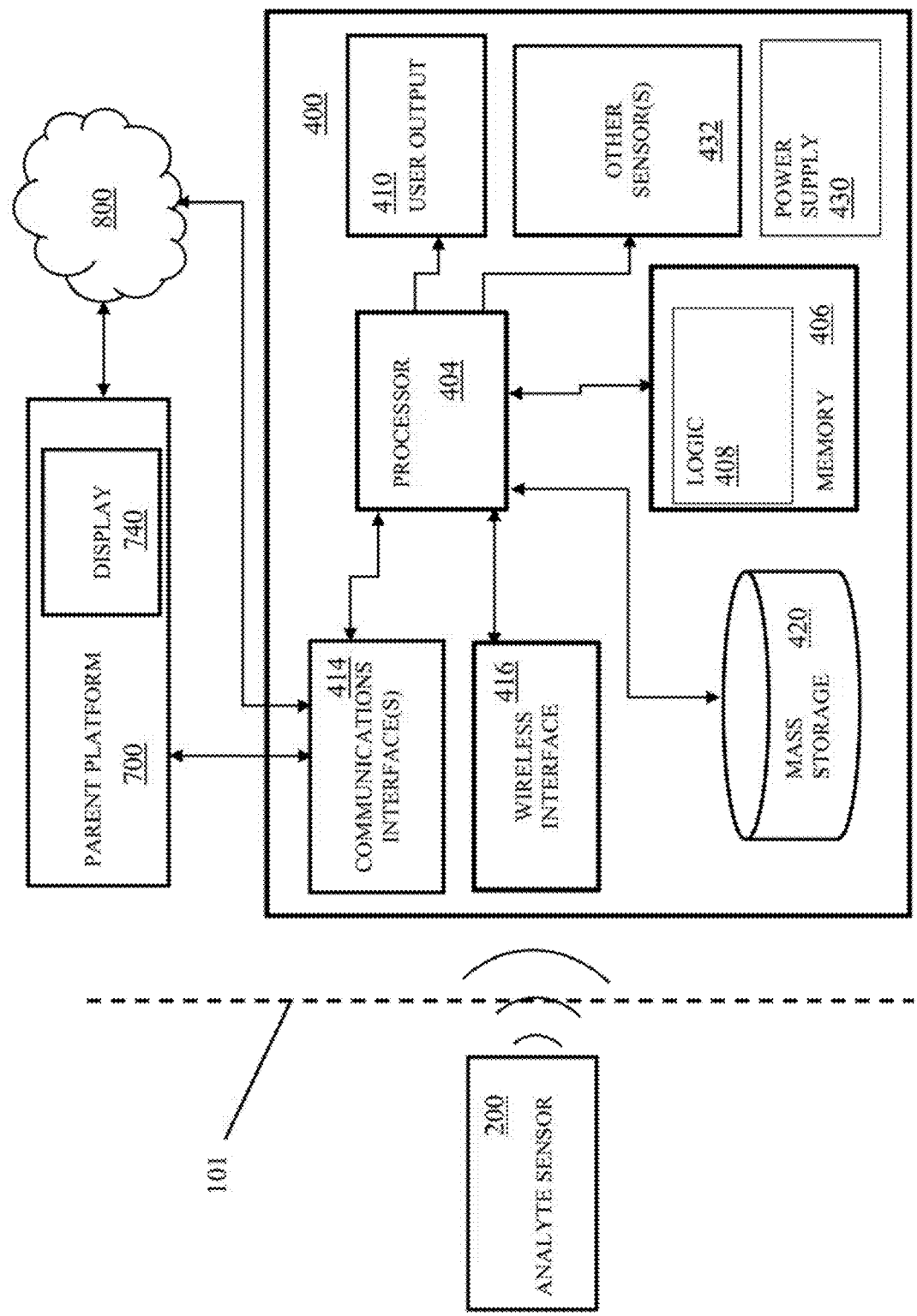
FIG. 4B is a functional block diagram illustrating an exemplary embodiment of local receiver apparatus of FIGS. 3A and 3B.

Referring now to FIGS. 4A-4B, various embodiments of the receiver apparatus 400 and 450 shown in FIGS. 3-3C herein are described in detail.

FIG. 4A depicts a functional block diagram of one embodiment of the receiver and processor apparatus 450 (i.e., a dedicated receiver apparatus), in wireless communication with the analyte sensor 200 of FIG. 3C via the interposed tissue (boundary) 101. As noted previously, the present disclosure contemplates use of partially-implanted (e.g., transcutaneous or percutaneous) or even non-implanted analyte sensor devices, as well as the fully-implanted device (e.g., sensor apparatus 200 of FIGS. 2-2C).

As shown in FIG. 4A, the dedicated receiver apparatus 450 includes a processor 404 (e.g., digital RISC, CISC, and/or DSP device), and/or a microcontroller (not shown), memory 406, software/firmware 408 operative to execute on the processor 404 and stored in e.g., a program memory portion of the processor 404 (not shown), or the memory 406, a mass storage device 420 (e.g., NAND or NOR flash, SSD, etc. to store received raw or preprocessed data, post-processed data, or other data of interest), a wireless interface 416 (e.g., narrowband or other, described below) for communication with the sensor apparatus 200, a communications (e.g., wireless) interface 414 for communication with the network entity 800 (if desired), a power supply 430 (e.g., NiMH or Lithium ion battery, or other as described below), and a graphical display device 440. The dedicated receiver apparatus 450 can optionally include one or more output device(s) 410 (i.e., other types of user outputs in addition to the graphical display device 440) for communication of the desired data (e.g., glucose level, rate, trend, battery "low" alerts, etc.) in addition to the display 440. As described in greater detail subsequently herein the output device(s) may include for example visual, audible, and/or tactile (e.g., haptic) modalities or mechanisms, which can be used alone or in concert depending on user context, desired functionality, and receiver and processor apparatus configuration.

Additionally, the apparatus 450 can optionally include one or more additional external sensors 432. The one or more external sensors 432 may be any of a temperature sensor, an accelerometer, a pulse meter, a blood pressure sensor, and/or other types of sensors. In one example, the external sensors 432 of the receiver 450 can be used in place of the one or more internal sensors 232 of the sensor apparatus 200. In another example, the external sensors 432 can be used cooperatively with the internal sensors 232 to, inter alia, generate a duplicate set of data and/or a complimentary set of data collected from the internal sensors of the implanted sensor device.

In one specific implementation, the external sensors 432 can be calibrated to the internal sensors 232 (such as e.g., during "training mode" operation of the sensor system), In such an implementation, subsequent "other sensor" data (i.e., data collected from sensors other than the target blood analyte sensor) can be collected from the external sensors 432 during operation of the sensor system in the "detection mode". Further, the internal sensors can be substantially turned "off", thereby e.g., decreasing power usage and/or processing requirements of the implanted sensor.

FIG. 4B is a functional block diagram showing one embodiment of the local receiver apparatus 400, in wireless communication with the parent platform 700 and the analyte sensor 200 (discussed supra) of FIG. 4 via the interposed tissue (boundary) 101.

Similar to the receiver and processor apparatus 450, the local receiver apparatus 400 includes a processor 404 (e.g., digital RISC, CISC, and/or DSP device), and/or a microcontroller (not shown), memory 406, software/firmware 408 operative to execute on the processor 404 and stored in e.g., a program memory portion of the processor 404 (not shown), or the memory 406, a mass storage device 420 (e.g., NAND or NOR flash, SSD, etc. to store received raw or preprocessed data, post-processed data, or other data of interest), a wireless interface 416 (e.g., narrowband or other, described below) for communication with the sensor apparatus 200, a communications (e.g., wireless) interface 414 for communication with the parent platform 700 and/or the network entity 800 (if desired), and a power supply 430 (e.g., NiMH or Lithium ion battery, or other as described below). The apparatus 400 also includes one or more output device(s) 410 (such as e.g., visual, audible, and/or haptic modalities or alert mechanisms) for communication of the desired data (e.g., glucose level, rate, trend, battery "low" alerts, etc.). Additionally, the apparatus 400 can optionally include one or more external sensors 432, such as those described above with reference to FIG. 4. In an alternate embodiment, the one or more other sensors can be located in a separate implantable apparatus positioned proximate to the sensor 200 during implantation.

Notably, in the embodiment shown in FIG. 4B, the local receiver 400 lacks a full graphical display device (such as the graphical display device 440 shown in FIG. 4A). Exclusion of the foregoing graphical display allows for overall reduced dimensions of the local receiver apparatus 400 making it suitably sized for wear or implantation (such as the exemplary wearable and implantable local receivers discussed supra and described in U.S. patent application Ser. No. 15/368,436 filed Dec. 2, 2016 and previously incorporated herein). Rather, the data from the local receiver apparatus 400 is displayed at a full graphical display device 640 associated with the parent platform 700. In some embodiments, the local receiver 400 includes a reduced or limited graphical display (i.e., small graphical display) as one of the output device(s) 410. For example, a wrist wearable local receiver can include a small LCD, or even a capacitive touch screen for sending alerts and/or other information to the user as well as receiving input from the user.

Additional configurations and functionality of the various receiver apparatus are described in U.S. patent application Ser. No. 15/368,436 filed Dec. 2, 2016 and previously incorporated herein.

Operational Methods—

Figure 5:
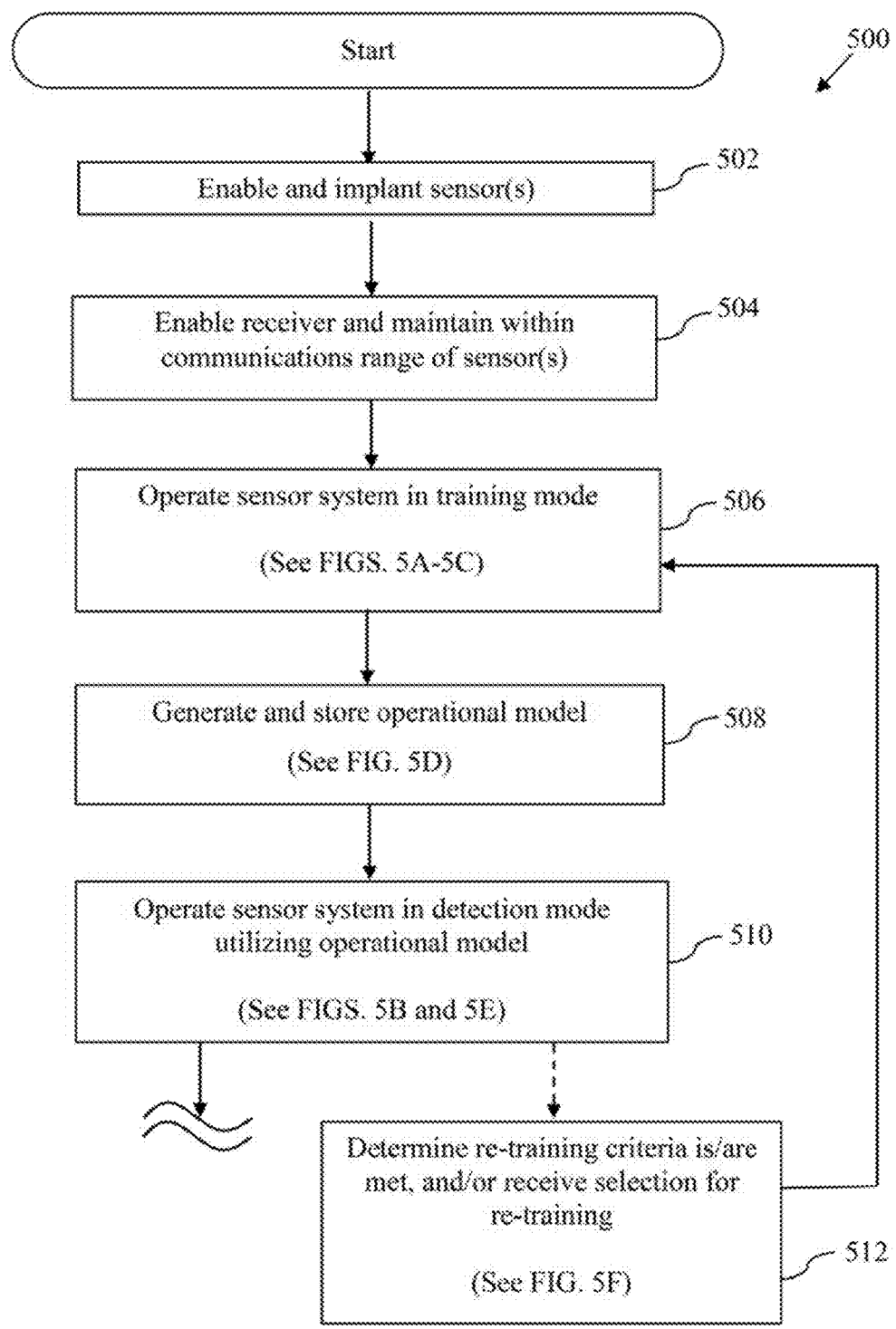
FIG. 5 is a logical flow diagram illustrating one exemplary embodiment of a generalized method of operating the implantable sensor system for blood analyte measurement according to the present disclosure.
Figure 6:
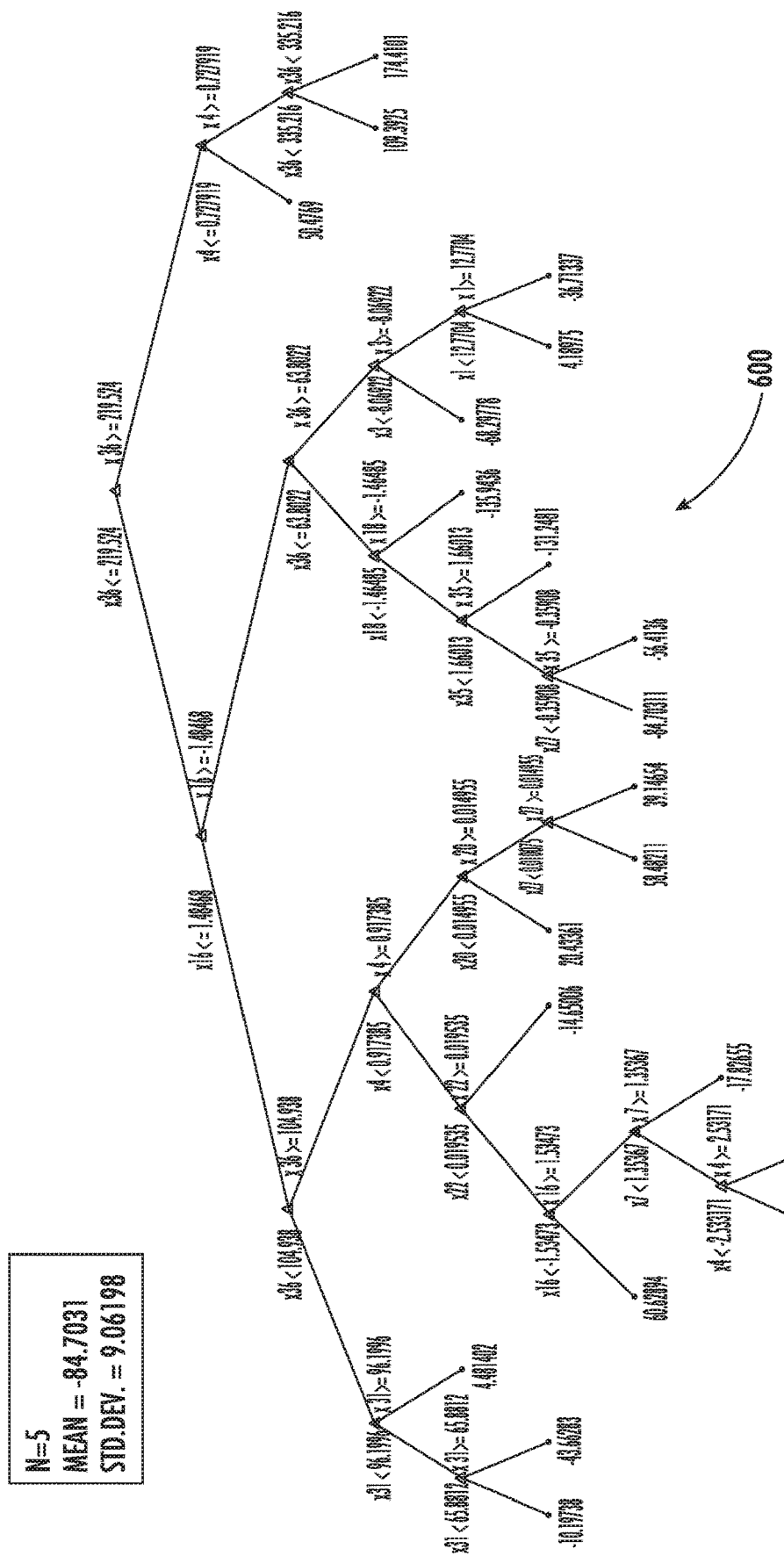
FIG. 6 is a graphical representation of an exemplary decision tree used in model generation according to one embodiment of the present disclosure, wherein each end-node predicts a specific error (or source).

Referring now to FIGS. 5-6, exemplary embodiments of the methods of operating the analyte sensing system (e.g., a system including either or both of the local receiver apparatus 400 and the receiver and processor apparatus 450) are described in detail.

FIG. 5 is a logical flow diagram depicting an exemplary embodiment of a generalized method 500 for operation of the sensor system according to the present disclosure. As shown in FIG. 5, the method 500 includes first enabling and implanting the sensor 200 (or others) per step 502. In the case of the implantable sensor of FIG. 2, the sensor is enabled, implanted in the host (such as via the procedures described in U.S. patent application Ser. No. 14/982,346 filed Dec. 29, 2015 previously incorporated herein), and tested as part of step 502.

Next, the receiver apparatus 400, 450 (e.g., any of those of FIGS. 4-4A herein) is enabled, and maintained within communications range of the sensor apparatus, per step 504. In one variant, the exemplary embodiment of the sensor apparatus 200 uses a 433 MHz narrowband RF transmitter (such frequency having good signal transmission characteristics through human tissue), and hence has a communications range, dependent on transmission power, of at least several feet. Hence, in one implementation of the method step 504, the host/user merely needs to keep the receiver 400, 450 within arm's reach, or somewhere on their body personally. As discussed infra, however, certain embodiments of the disclosure may implement the "machine learning" aspects indigenously on the implanted sensor apparatus 200 itself, thereby effectively obviating the need for communication with the external receiver 400, 450, at least for functions relating to systemic or other error modeling and correction.

Subsequent to enablement and implantation of the sensor (and enablement of the receiver), the sensor system is operated in an initial "training mode" (step 506, and described below in greater detail with respect to FIGS. 5A-5C), wherein the detector elements of the sensor 200 are operational and producing signals, yet the data are not output to the user or other entity, but rather used for "off line" analysis and error model generation.

Data collected and/or received during the training mode operation are then used to generate and store an operational model (such as e.g., a user-specific operational model) (step 508, and described below in greater detail with respect to FIGS. 5D-5E).

Next, at step 510, after the model is generated, the sensor system is operated in a detection mode (i.e., a mode whereby data collected from the user is corrected as needed, and output for use by the user or other entity such as a caregiver), based on the operational model.

In some embodiments, operation of the sensor system utilizing the initial operational model is continued until explant of the sensor. Optionally, per step 512, the system can determine that one or more criteria for operation of the system in a subsequent training mode (i.e., "re-training") are met (described in greater detail below), and/or the system can receive a selection from a user or a medical professional/caregiver for re-training. If such a determination or selection is made, the sensor system returns to step 506 for a repeated operation in the training mode.

It is also appreciated that while the generalized methodology set forth above with respect to FIG. 5 utilizes implant of the sensor 200 as a precondition for training of the machine learning algorithms (so as to ostensibly provide the best training environment for that particular sensor/user combination), this may not always be a requirement. For example, the present disclosure contemplates conditions where the sensor 200 may be "pre-trained" prior to implantation, such as based on data previously acquired for that same individual (e.g., as part of a prior training session and/or prior sensor implantation), or even data derived from one or more similarly situated individuals (e.g., family member, similar physiologic characteristics, similar disease expression, etc.). In such cases, the sensor 200 to be implanted in the individual may for instance be pre-programmed with data representative of a prior operational model using wireless or other data communication with the sensor 200 (such as via its 433 MHz or Bluetooth wireless interface described supra) prior to implantation, such that the model (data) is stored and accessible immediately upon activation of the sensor 200 in vivo.

It is further appreciated that the training of the sensor, and/or application of the derived model (per step 508 of FIG. 5) may be delayed or "phased in" over time. For instance, in one contemplated scenario, the machine learning logic may be programmed to collect data and generate several operational models, including further analysis of the models with respect to one another (and/or other criteria or models, such as those based on purely theoretical or certain a priori assumptions). In one such implementation, two or more successive models are generated via sensor data collected after implantation, and evaluated against one another for factors such as inter-model consistency, and/or rates of change of various attributes of the model (i.e., loosely correlated to an operational "shelf life" of the model(s)).

Similarly, different paradigms for generation of the models can be tested against one another, such as where for example a first model accounting for N factors or systemic error sources is compared against a second model accounting for N-x factors or sources, the latter ostensibly requiring less processing overhead and/or other resources. In effect, there may be diminishing returns to increasingly sophisticated modeling approaches, at the cost of additional required sensor inputs, processing, power consumption within the sensor 200, etc., especially when the incremental improvement afforded by the model is within a prescribed allowable error band or tolerance of the system (e.g., when the more complex model generates an improvement in measured blood glucose level accuracy of 0.1 mg/dl, but the system display, data storage, or other requisite accuracy is only 1 mg/dl).

Yet further, the present disclosure contemplates use of two or more models collectively, whether in parallel or in sequence (or based on context or events, such as may be detected by one or more ancillary sensors of the type described supra; e.g., pressure, temperature, acceleration, conductivity, pH, oxygen level, blood flow, electrical impedance, and others). For example, in one such scenario, the corrections or other output generated through application of a given model to operational data may be averaged or otherwise mathematically or statistically combined, or weighted, with similar outputs or corrections generated from other heterogeneous models, so as to avoid any particular model skewing the correction unduly. Likewise, certain models may be best suited or perform best when in a prescribed context or operational setting, and hence the weighting of that model (or even use or non-use of the model in its entirety) may be algorithmically adjusted based on e.g., sensor data input(s). As a simple illustration, consider a user with implanted sensor 200 who is ambulatory (as determined by e.g., accelerometer data resident on the sensor 200 or external receiver 400, 450, and/or yet other sensors such as body temperature). Certain systemic error sources may be more applicable or present themselves to a greater degree in an ambulatory vs. non-ambulatory state, and hence models adapted to such error sources would ostensibly perform better in the ambulatory state as compared to others not so adapted. Hence, upon detection of ambulation, the computerized logic may select (or at least more heavily weight) such ambulation-specific models for application to the generated operational sensor data.

Training Mode Operation

Figure 5A:
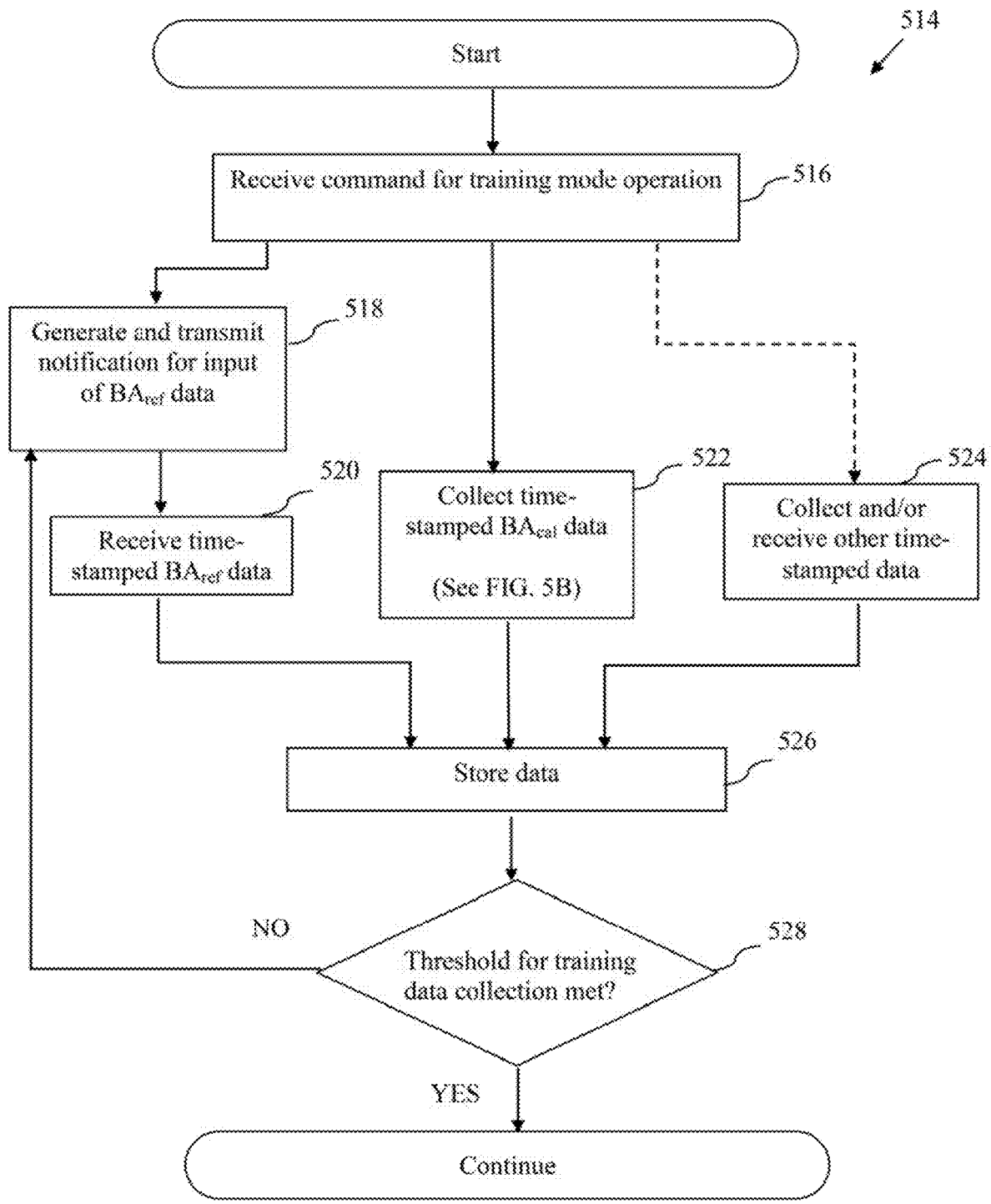
FIG. 5A is a logical flow diagram illustrating one exemplary implementation of the "training mode" operation of the implantable sensor system according to the method of FIG. 5.

Turning now to FIG. 5A, a logical flow diagram of an exemplary embodiment of a method 514 for operation of the sensor system in the training mode (step 506 of FIG. 5) is shown and described.

First, at step 516, a command is received to operate the sensor system in the training mode. In one example, after enablement and implantation of the sensor, the user, a medical professional or caregiver enters a selection for operating the sensor system in the training mode via a graphical user interface (GUI) displayed on a display device associated with one or both of the receiver 400, 450 and/or the parent platform 600, such as touch-screen icon selection corresponding to a "calibration" or "learning" function or the like, which causes generation and transmission of a wireless data command to the sensor 200. In an alternate example, the sensor system can be automatically configured to operate in the training mode after implantation e.g., by performing an automatic "boot-up" procedure, such as based on pre-stored firmware in e.g., ROM. In other words, once the sensor is enabled and implanted, and paired (wirelessly) with the receiver 400, 450, the sensor system can automatically enter training mode operation.

In yet another alternate example, the sensor system can be pre-programmed to automatically operate in the training mode after implantation each time that it receives (either based on a user input into the receiver 400, 450 or via direct transmission from a reference meter associated with the user and the sensor system) a new reference analyte value.

In any of the above examples, the command to initiate training mode operation (via e.g., a received wireless command or automatic initiation) can be optionally delayed. In some cases, initiation of the training mode can be set to occur after expiration of a delay period (e.g., a day, a week, a month, etc.). Such a delay period can, depending on the desired functionality, be selected by the user or medical professional, or alternatively the delay period can be pre-programmed. Provision of the delay period can allow the tissue surrounding the implanted to heal and/or adjust to the presence of the sensor prior to collecting "training" data from the implanted sensor (thereby making the physiologic and chemical environment surrounding the implanted sensor 200 ostensibly more stable, including blood vessel perfusion in the immediate locality). Note that this delay is to be contrasted with that described previously; i.e., the latter referencing application of the model(s) to operational data.

After the training mode is initialized, a notification is generated and transmitted to the GUI requesting input of external blood analyte reference data ($BA_{ref}$) per step 518. For example, during training mode operation, the sensor system can periodically transmit notifications to a user to enter a manual blood analyte reading such as e.g., a blood glucose level determined via the aforementioned "finger-sticking" method and/or laboratory-type analyzers (e.g., YSI analyzers). For example, notifications may be sent to the user hourly, every two hours, every three hours, daily, weekly, or according to other desired notification schedules.

In response to receipt of the notification, the user obtains and inputs $BA_{ref}$ data (such as e.g., entering data via the GUI) which is received by the sensor system per step 520. The $BA_{ref}$ data either include a time-stamp generated by an external digital blood analyte measurement device or are time-stamped when received by the sensor system. It is noted in passing that in some cases the internal time domains maintained by physically separate devices are not perfectly aligned, and hence a time stamp applied to data transmitted from a device before transmission (e.g., based on collection of the data at actual time t) is different than or misaligned with a time stamp applied by another device to data collected at that same (actual) time t. Hence, the two time stamps indicate different values, even though both actually collected at time t. Accordingly, the present disclosure contemplates using a single, unified time domain (e.g., that of the sensor apparatus 200, or the receiver 400, or even the parent platform 600), for consistency, such as where all data is time-stamped with values associated with the unified domain. It will be appreciated that the time-stamping in such implementations, while conducted based on the unified domain, need not be performed by the device maintaining the unified domain (clock). For example, in one variant, the parent platform 600 periodically transmits clock signals indicative of time in its unified domain (referenced to a known standard or event) to the receiver apparatus 400 and/or sensor apparatus 200, the receiving devices using this data to periodically align their own clock domains as needed. Other schemes for maintaining unified time-stamp data between the various data sets and devices will be appreciated by those of ordinary skill given the present disclosure.

In an alternative example, a user can manually enter a time at which the $BA_{ref}$ data were collected. In another alternative example, the $BA_{ref}$ data can be digitally uploaded to the sensor system without requiring a user to manually input the $BA_{ref}$ reading.

It is also appreciated that user notification and/or input may be obviated in favor of direct communication between the sensor system and the source of $BA_{ref}$, such as where the sensor system generates and transmits a datagram to an API (application programming interface) of the reference data source, requesting the reference data. Upon receiving the datagram, the reference data source generates and transmits a responsive datagram containing the requested reference data and any other appropriate data such as temporal reference, source ID, CRC or other error correction data, etc. The user may also be given confirmatory capability via the GUI if desired (e.g., notification to the user via GUI display that the source has sent a $BA_{ref}$ value to the sensor 200, and requesting assent by the user via the GUI or other input device of the receiver 400, 450 to enter and utilize the value). Alternatively, the reference data source may initiate the data transmission activity, when e.g., new reference data have been generated and are available for transmission to the sensor system.

Contemporaneous with the receipt of $BA_{ref}$ data, the sensor system collects and calculates a measured blood analyte level reading ($BA_{cal}$) per step 520.

Methods for collection and calculation of blood analyte level during training mode operation of the sensor system are discussed with reference to FIGS. 5B and 5C. Specifically, an exemplary embodiment of a method 522 of operating the implanted sensor 200 with the local receiver apparatus 400 and the parent platform 600 and/or the receiver and processor apparatus 450 for collection and calculation of training mode $BA_{cal}$ data, as well as an exemplary method 529 of data processing and output during training mode operation are described in detail infra.

Figure 5B:
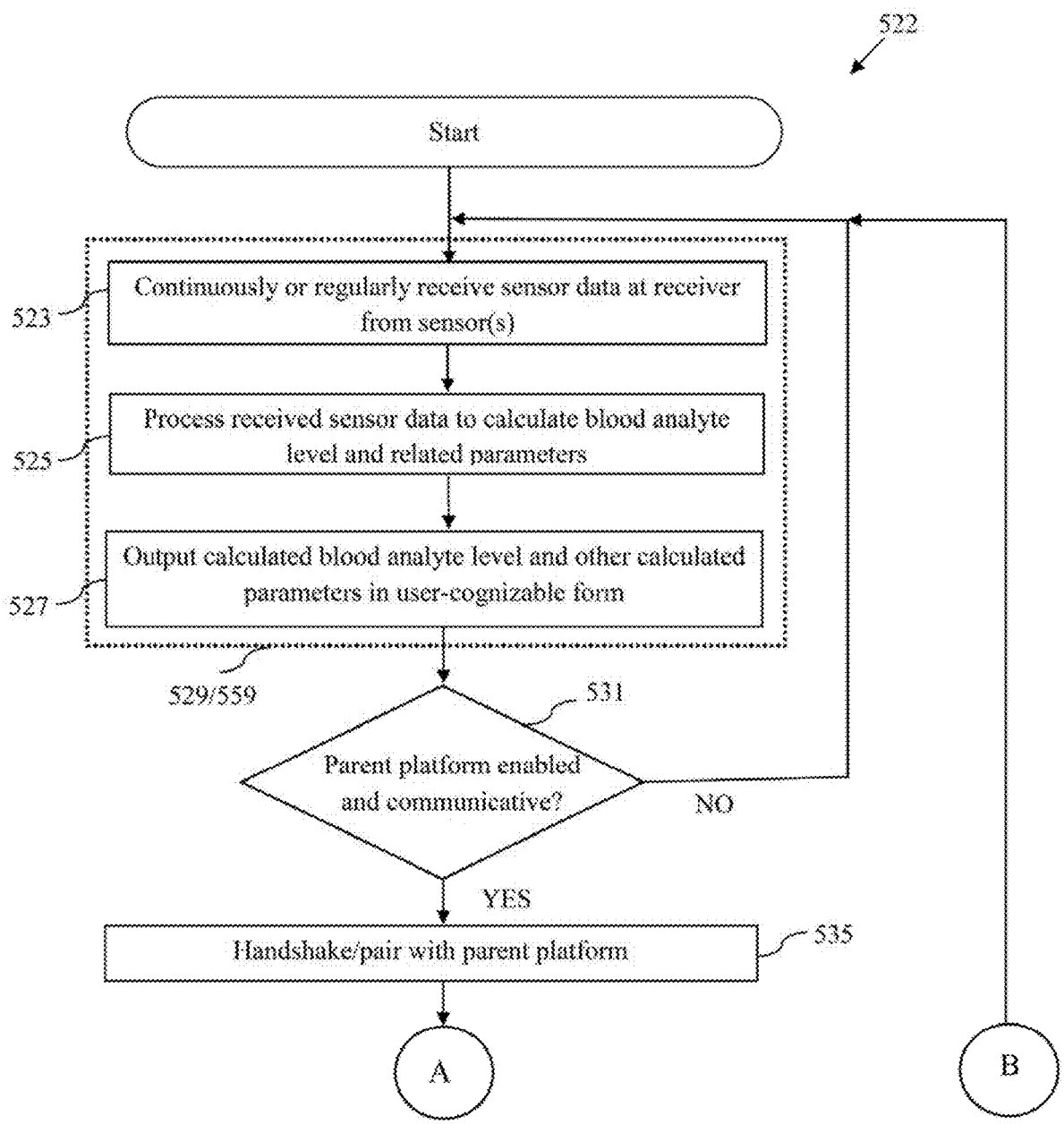
FIG. 5B is a logical flow diagram illustrating one exemplary implementation of the sensor analyte detection and output according to the method of FIG. 5.
Figure 5B:
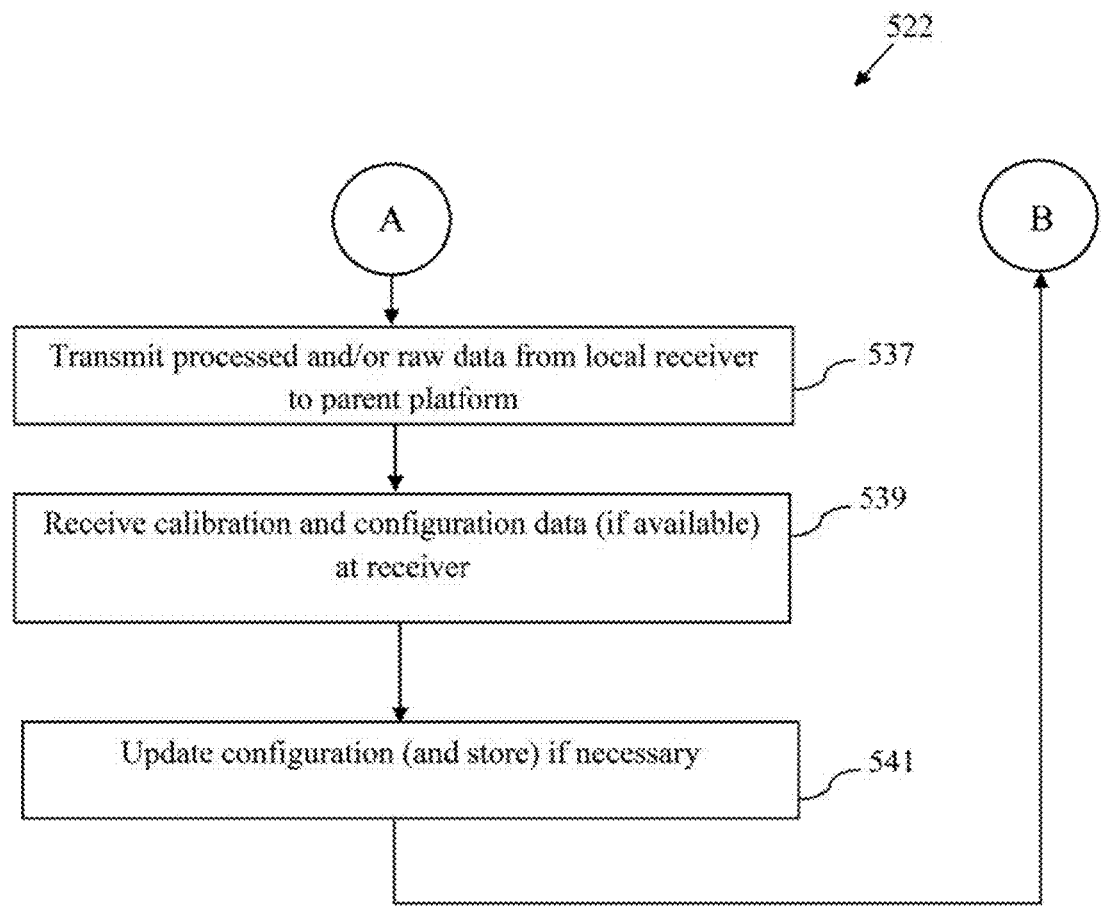

Specifically, as shown in FIG. 5B, the enabled sensor 200 communicates data wirelessly to the receiver apparatus 400, 450, such as on a periodic, event-driven, continuous, or other basis per step 523 of the method 522. Note that the transmission and reception frequencies or schedule need not necessarily coincide completely. For instance, the transmitter of the sensor apparatus 200 may transmit according to a prescribed periodicity or frequency, while the receiver 400, 450 may utilize a less frequent sampling of the transmissions, or the transmissions may be buffered or queued for opportunistic transmission (and/or processing by the receiver 400, 450). Similarly, a polling or similar approach may be used, such as where the receiver 400, 450 polls the sensor 200 when it is ready to receive the data, which may be periodic or aperiodic in nature.

Per step 525, the received sensor data are processed to calculate blood analyte level, and any related parameters or data derived therefrom. Such processing may occur when the data are received, or collectively in one or more aggregations or batches of data (e.g., sensor data collected or received over a prescribed time period, number of iterations, representative of a prescribed duration of in vivo operation, or other).

Optionally, per step 527, the calculated blood analyte level (e.g., glucose concentration in e.g., mg/dL or mmol/L) is output to the user in a cognizable form, such as visually, via haptic apparatus, audibly, and/or yet other means, as described elsewhere herein. Similarly, other information (such as, e.g., trend of the blood glucose level, ROC, and/or alert notifications discussed in detail infra) may be output from the receiver 400, 450 via the same or different cognizable medium. It will be appreciated that output of blood analyte level may also be withheld or suspended during training mode operation of the sensor system, so as to avoid potentially erroneous values being perceived by the user before model generation and application are completed.

With use of the local receiver 400, the method 522 further may include determining whether the parent platform 600 (e.g., the user's more fully-functioned tablet, smartphone, etc.) is "communicative" with the local receiver 400 (per step 531), so as to enable the parent platform to utilize its functionality in supply and/or processing of the obtained data. When communications between the local receiver 400 and the parent platform 600 are enabled (per step 535), the local receiver and parent platform handshake (e.g., pair according to a Bluetooth pairing protocol and/or an Internet of Things (IoT) protocol, with the local receiver as the slave, and the parent as the master).

It will be appreciated that while the foregoing scenario contemplates use of a local receiver 400 to communicate with the parent platform 600, the present disclosure also contemplates, inter alia, use of direct communication between the sensor apparatus 200 and the parent platform 600, such as via wireless (RF) communications. In one such implementation, the sensor apparatus 200 includes a Bluetooth wireless interface (e.g., BLE variant) which operates at 2.4 GHz and which has been demonstrated by the Assignee hereof to penetrate human tissue with sufficient efficacy so as to maintain a wireless communication channel between e.g., the implanted sensor apparatus 200 and the comparably Bluetooth-equipped parent platform 600, the latter further including an application program or firmware configured to extract data (whether raw or pre-processed on-board the sensor apparatus 200) from one or more messages wirelessly transmitted from the sensor 200. Additional details on one exemplary implementation of the sensor-to-parent platform interface are described in co-pending U.S. application Ser. No. 15/368,436 filed Dec. 2, 2016 and entitled "Analyte Sensor Receiver Apparatus and Methods", previously incorporated herein.

At step 537, processed and/or raw data from the local receiver 400 are transmitted to the parent platform 600. Per step 539, the receiver(s) receive the configuration and/or calibration data (as applicable from the parent platform 600 in an example where a local receiver 400 is utilized), e.g., such as "fingerstick" or blood glucose monitor (BGM) values entered by the user via the GUI. Alternatively, in an example where a receiver and processor apparatus 450 is utilized, a user or a medical professional can enter configuration and/or calibration information via a GUI displayed at the apparatus 450.

Per step 541, the configuration of the receiver (e.g., the alarm setting values, alert logic or hierarchy such as "haptic then visual then audible", etc.) is also optionally updated as needed. Similar to the optional withholding or suspension of output of blood analyte level during training mode operation of the sensor system, receipt of configuration updates may be optionally suspended or withheld during the training mode and later updated when the receiver initiates detection mode operation.

Alternatively, if the parent platform is not "communicative" (e.g., outside range, busy, preempted, etc.) per step 531 of the method, operation of the local receiver 400 is continued (i.e., periodic or continuous receipt and processing of sensor data).

Figure 5C:
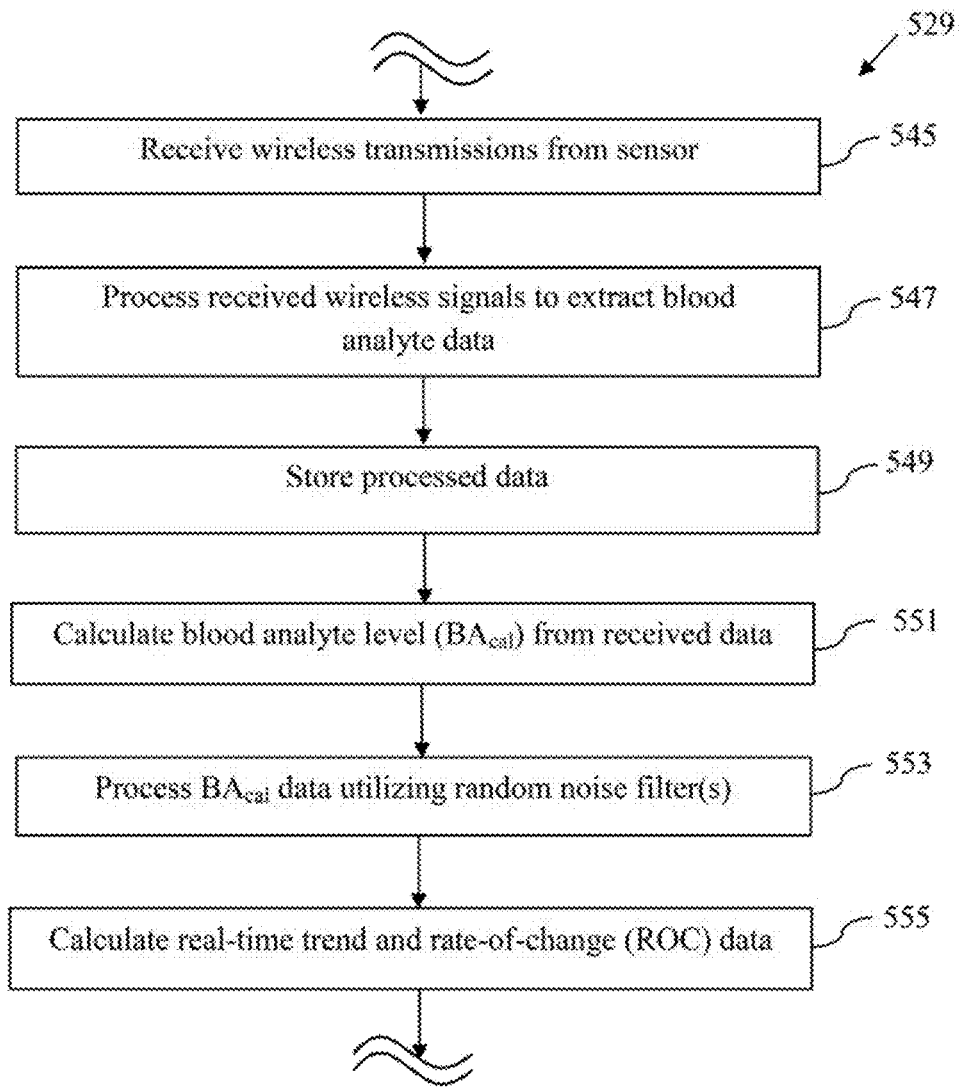
FIG. 5C is a logical flow diagram illustrating one exemplary implementation of the sensor data processing and output during "training mode" operation according to the method of FIG. 5B.

FIG. 5C is a logical flow diagram illustrating one exemplary implementation of the sensor data processing and output methodology 529 for the local receiver 400 and the parent platform 600 (or the receiver and processor apparatus 450) during training mode operation according to the method 522 of FIG. 5B. As shown, the method 529 in one embodiment includes first receiving the wireless data transmissions from the (implanted) sensor 200 per step 545. Next, per step 547, the received wireless signals are processed, and the processed data stored (step 549). Exemplary implementations of sensor data receipt and demodulation/unscrambling methodology for the receivers 400, 450 are described in U.S. patent application Ser. No. 15/368,436 previously incorporated herein.

Next, the calculated blood analyte level ($BA_{cal}$) is determined per step 551. Optionally, one or more random noise signal filters (such as e.g., finite impulse response (FIR), infinite impulse response (IIF), Kalman, Bayesian, and/or other signal processing filters) can be applied to the $BA_{cal}$ reading to correct for error due to random noise (i.e., "e" defined supra) per step 553. As a brief aside, as will be appreciated by artisans of ordinary skill in the signal processing arts, typical "white" noise or "random" noise is characterized by a constant power spectral density. Colored noise spectra may have non-constant power spectral density; e.g., red tinted noise has less attenuation at longer wavelengths (lower frequencies), whereas blue tinted noise has less attenuation at shorter wavelengths (higher frequencies). Common techniques for removing the effects of random noise include without limitation e.g., time based averaging, statistical sampling, spectrally weighted averaging, and/or any number of other weighted filtering techniques.

Further, other parameters of interest if any (such as real-time trend and/or rate of change) are calculated per step 555.

Returning to FIG. 5A, per step 524, in addition to receiving the $BA_{ref}$ data and collecting/calculating the $BA_{cal}$ data, the sensor system can optionally collect and/or receive other data. In one exemplary implementation, the system can collect data (hereinafter "$OS_{cal}$" data) received from one or more other sensors (such as e.g., internal sensors 232 on the implanted sensor 200, external sensors 432 such as on the receiver or parent platform, or other additional sensors associated with the blood analyte detection system). For example, the one or more internal sensors 232 associated with the implanted sensor 200 (or similar sensors implanted proximate to the sensor 200) can collect/calculate internal $OS_{cal}$ data such as e.g., internal body temperature in the region of the implanted sensor, pulse rate of the user, motion and/or orientation data, pressure, pH, local blood flow/tissue perfusion, electrical impedance of the sensor/tissue interface, blood analyte concentration of other non-target analytes (e.g., oxygen), and/or other internal data. In another example, the one or more external sensors 432 associated with the receiver 400, 450 can collect external $OS_{cal}$ data such as e.g., external body temperature, pulse rate of the user, blood pressure, motion and/or orientation data, and/or other external data, or even pre-processed "state" or other context data; e.g., as to what activity or state the user is currently engaged in (such as ambulatory, sleeping, exercising, eating, etc., so in effect the computerized modeling logic does not have to deduce or derive this information from raw sensor data alone). In another example, the $OS_{cal}$ data can include information that the system calculates using stored data, and may comprise, e.g., the length of time that the sensor has been in operation, the rate of change of sensor signals, etc.

Additionally or alternatively, a user or medical practitioner/caregiver can manually enter other external data such as e.g., body temperature, pulse rate, blood pressure, indicator of exercise, an indicator of intake of medication, an indicator of resting state (e.g., sleep), an indicator of active state (e.g., exercise), an indicator of ingestion of food (e.g., slow-acting carbohydrates, fast-acting carbohydrates, etc.), and/or other manually entered data, such as via a user interface and an application layer program operative to run on the receiver 400, 450, or parent platform 600 (depending on how each is configured). It will be appreciated that manually entered data can be used alone or in combination with data collected via the internal sensors 232 and/or the external sensors 432.

In another implementation, the other data can comprise both internal $OS_{ca}$ data and external $OS_{cal}$ data (and/or manually entered external data). In one such variant, the internal sensor data are generated only periodically, such as during several discrete periods during training phase operation to ensure signal stability, yet minimize electrical power consumption with the sensor 200 so as to, inter alia, enhance battery life. In another variant, the external $OS_{cal}$ data can be calibrated to the internal $OS_{cal}$ data during the training mode operation, such as where internal temperature is registered (by the internal temperature sensor of the analyte sensor 200, or a separately implanted internal sensor) as a first value that is higher than say an externally-sensed temperature produced by a skin temperature sensor on the local receiver 400, thereby requiring application of an offset or calibration factor for data generated by the external sensor to reflect internal body temperature. Thus, in subsequent detection mode operation of the sensor system, the external sensors (e.g., sensors 432 on the receiver) can be utilized, and the internal sensors can be substantially "turned off," thereby decreasing power and processing demands on the implanted sensor 200 (or the other sensors implanted proximate to the sensor 200 if used).

In yet another variant, both the external $OS_{cal}$ data and the internal $OS_{cal}$ data are collected and utilized during the training mode operation and the detection mode operation to improve accuracy via e.g., collating data from multiple sources. In still other variants, external and internal $OS_{cal}$ data can be dynamically selected for use during detection mode operation based on data analyses carried out during the operational model generation (discussed supra).

In each of the above implementations, the other data (i.e., the $OS_{cal}$ data and/or manually entered data) are optionally time stamped such that they can later be temporally correlated with the $BA_{ref}$ data and the $BA_{cal}$ data during data processing.

Per step 526 of FIG. 5A, the data collected and received at steps 520-524 are stored on a storage device associated with the sensor 200, the receiver 400, 450, the parent platform 600, and/or another storage device in data communication with the sensor system. For example, the data can be stored at one or more of the mass storage 420 associated with the receiver 400, 450, the storage 220 associated with the sensor 200, a storage device associated with the parent platform 600 (not shown), or a network ("cloud") storage device accessible via data communication with the network 700. Storage is effected via the software/firmware operative to run on the calculating or receiving platform. For example, in one configuration, the collected data are calculated on-board the sensor 200 using its internal computerized logic alone, and the resulting data stored locally onboard the sensor 200. In another configuration, data calculation is offloaded to the external receiver 400, 450 or even parent platform via the wireless interface of the sensor, and the processed data returned to the sensor 200 for local storage. In another configuration, the data calculation is offloaded to the external receiver 400, 450 or parent platform via the wireless interface of the sensor, and the processed data stored external to the user (i.e., in the receiver 400, 450 or parent or cloud), and a wireless datagram sent to the sensor apparatus 200 indicating to the latter that the values have been calculated, and are accessible at prescribed data storage locations, or via API calls.

Receipt, collection, and storage of data are continued until a threshold of stored data or other criterion is met. Specifically, in the embodiment of method 514, it is determined whether a statistically relevant amount of data has been stored at decision block 528. In one exemplary implementation, the "training mode" is employed for a pre-determined amount of time (e.g., one day, one week, two weeks, etc.). In the foregoing implementation, the threshold for data collection is the pre-determined amount of time for the duration of the training mode operation; therefore, the determination of whether the threshold for data collection has been met includes determining if a time elapsed since the initiation of the training mode is greater than the pre-determined amount of time, such as via a clock function resident on the local receiver logic. This threshold can be made irrespective of actual data collected, or coupled with a prescribed threshold of data collection volume (described infra).

In another implementation, the "training mode" is implemented until a pre-determined number of data points (i.e., a pre-determined amount of data having corresponding time points) are collected. In this implementation, the threshold for data collection is the pre-determined number of data points; and therefore, the determination of whether the threshold for data collection has been met includes determining if a number of collected data points is greater than the pre-determined number of data points (which may be e.g., on a numerical basis such as an integer number, on an aggregated data size/storage value such as N kb or Mb, on a storage address basis such as a number of row/column addresses in a memory array, or yet other). It will be appreciated that other threshold criteria and/or a combination of threshold criteria may be utilized to determine whether the sensor system has collected sufficient "training mode" data. For instance, the data collection may be controlled based on a subsequent processing of collected data, such as where a prescribed first amount of data are obtained, and subsequent steps of the methodology herein (i.e., model processing/generation) are performed to determine if satisfactory results can be obtained, such as based on statistical criteria. In effect, a trial run on analysis and model generation may be performed using a given amount of collected data, so as to determine statistical or other sufficiency of the data with respect to generation of a useful model. Depending on the model chosen for application during the operational phase or mode (which may in fact be multiple models applied in series or tandem), certain data sets may or may not be sufficient for model generation and application in terms of their size, diversity, etc. Hence, by performing "look ahead" processing (including in an iterative fashion; i.e., wherein a first data set is collected, evaluated, and second heterogeneous or more expansive data set is subsequently collected and evaluated), the data collection threshold may be dynamically specified, as opposed to a predetermined value which, while conservative, may cause undue delay and utilization of sensor processing resources (and hence power consumption).

Per method 514, if the data collection threshold or criterion has not yet been met at decision block 528, data collection is continued. Alternatively, if the threshold or criterion is met, the training mode operation of the sensor system is completed, and the collected and received data are subsequently analyzed and processed for operational model generation as described elsewhere herein.

Although not specifically depicted in FIG. 5A, it will be appreciated that the training mode operation can additionally include a "manual override" or similar function selectable by a user and/or a medical professional. In one example, the manual override function allows the method 514 to stop prior to meeting the data collection threshold/criterion, and proceed to the operational model generation. In another example, the manual override function allows the method 514 to continue (i.e., allows collection of "training data" to continue) after the data collection threshold/criterion is met, prior to operational model generation, so as to permit enrichment of the collected data set, or for other reasons (e.g., to ensure that readings are taken in different ambulatory or other user contexts such that the data are representative in such regards).

Operational Model Generation

Figure 5D:
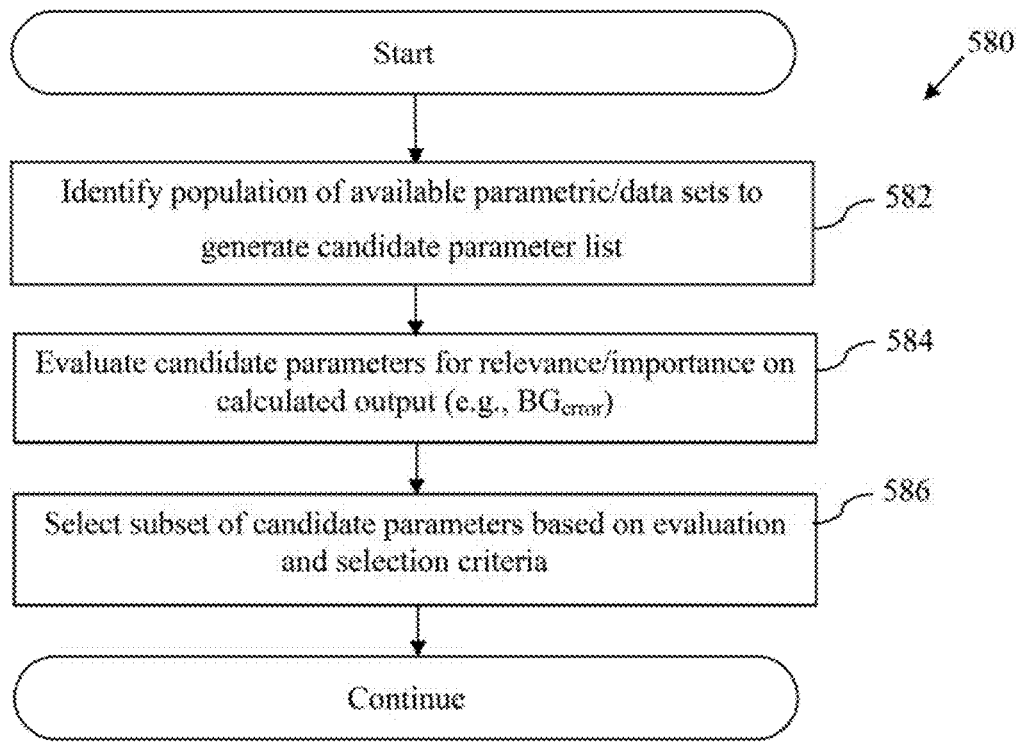
FIG. 5D is a logical flow diagram illustrating one exemplary implementation of operational model parameter selection methodology according to the method of FIG. 5.
Figure 5E:
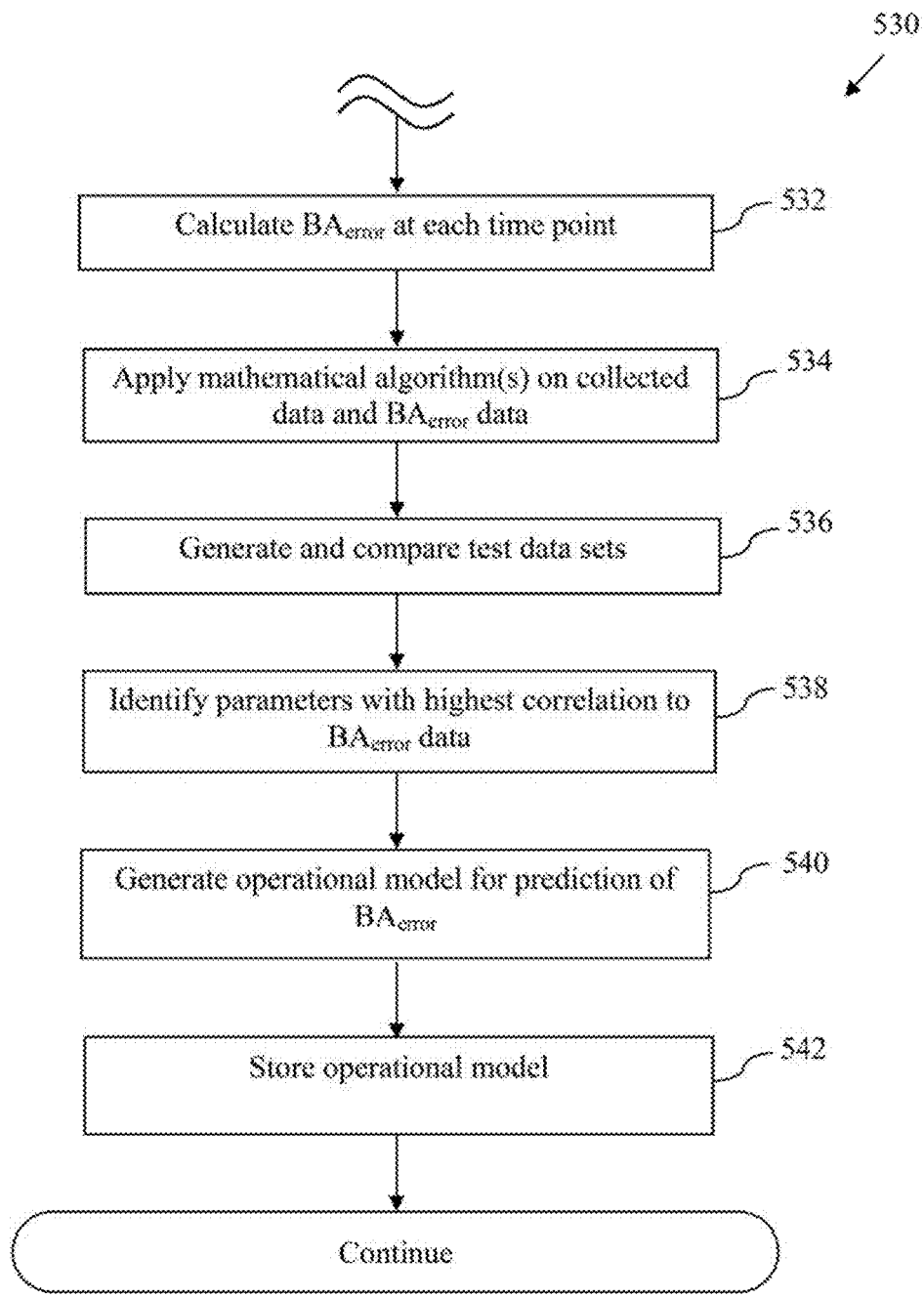
FIG. 5E is a logical flow diagram illustrating one exemplary implementation of operational model generation for the implantable sensor system according to the method of FIG. 5.

Referring now to FIGS. 5D-5E, exemplary methodologies for model parameter identification and operational model generation are described in detail.

As shown in FIG. 5D, the method of model parameter identification 580 includes first identifying a set of available model parameters per step 582. This set may be identified for example based on the available sensors and/or data accessible in a given hardware/software environment in which the sensor apparatus 200 will be used. For example, the accessible sensor/data set may be as little as (i) the blood analyte sensor(s) on the sensor apparatus 200, and (ii) external blood analyte (e.g., BG) reference data, such as from a fingerstick calibration device. More fully featured/instrumented applications may include more sensors and data sources. In the exemplary context of blood glucose measurement, some of the likely candidate parameters include: (i) reference background pO2 ($O_2$ partial pressure) measured by the CGM sensor; (ii) electrode(s) current measured by the CGM sensor; (ii) rate-of-change of electrode(s) current measured by the CGM sensor; (iv) temperature measured by a temperature sensor (e.g. a thermistor) embedded in the CGM sensor or separate therefrom; (v) accelerations measured by an accelerometer embedded in or external to the CGM; (v) pressure (e.g., via indigenous piezoelectric or other sensor on the implant 200), (vi) pH, and (vii) "state" variable inputs such as user-input data regarding their activities, ambulatory state, items eaten and times, and the like.

Next, per step 584, the candidate model parameters identified in step 582 are evaluated for selection. In one embodiment, the candidate parameters are evaluated using analytical techniques structured to identify relative parameter importance. For example, once candidate parameters and a particular machine learning algorithm (including e.g., Decision Tree, Random Forest, etc.) are defined, those parameters demonstrating utility in reducing a specified error measure (e.g. MARD, MAD, outlier prevalence, etc.) in a training data set are selected by means of a "feature selection" technique. For example, when a Random Forest algorithm is trained using the model parameters and reference-derived $BG_{error}$, an "out-of-bag" or other predictor (parameter) importance can be evaluated, such as by permuting the input parameter values. See e.g., Out-of-Bag Estimation, L. Brieman, et al, University of California at Berkley (https://www.stat.berkeley.edu/~breiman/OOBestimation.pdf), incorporated herein by reference in its entirety, as one exemplary approach. In such an analysis, the parameters with higher importance metrics tend to better predict the output variable, $BG_{error}$.

Lastly, per step 586, a final list of parameters can then be selected, such as for example based on a pre-defined threshold of predictor importance. Alternatively, a simple criterion to select a prescribed number (e.g., top 'n') of predictors can be employed.

It will be appreciated that the parameter identification process may be conducted algorithmically (e.g., by an application computer program or other software based on provided data sets, heuristically by a human, or combinations thereof. Moreover, if the relevant model parameters are known a priori, such model identification methodology 580 may be completely obviated.

Turning now to FIG. 5E, an exemplary embodiment of a method 530 for data analysis and generation of an operational model (e.g., a user-specific operational model) is shown and described.

Per step 532, blood analyte detection error data ($BA_{error}$ data) is first calculated for the $BA_{cal}$ data, based on the received $BA_{ref}$ data, at each corresponding time point. For example, the $BA_{error}$ data can be calculated as the mean absolute relative difference (MARD) between the calibrated analyte sensor output ($BA_{cal}$ data) and the external analyte reference data ($BA_{ref}$ data), as set forth in Eqn. (2) below:

$$MARD = \frac{\sum_{1}^{N} |BA_{cal} - BA_{ref}|}{N} \quad (2)$$

where N is the number of matched pairs of sensor readings and reference samples.

Alternatively (or in tandem), the $BA_{error}$ data can be calculated as or by the frequency of outliers in the comparison of the $BA_{cal}$ data and the $BA_{ref}$ data, such as using the frequency of occurrences where $$|BA_{cal} - BA_{ref}| > A * BA_{ref} \quad (3)$$

where A is a threshold level that may have a value of, e.g., 0.2 or 0.3, so that outliers are determined to be instances where the sensor output differs from the reference value by more than, respectively, 20% or 30% of the reference value.

Additionally or alternatively, the $BA_{error}$ data can be calculated utilizing one or more other methods (such as e.g., standard deviation, mean absolute difference, etc.).

After calculation of $BA_{error}$ data, per step 534, one or more "machine learning" algorithms are selected/identified for modeling the $BA_{error}$ data. In one implementation, a single algorithm is pre-selected (e.g., an experimentally pre-determined algorithm) for utilization in model generation prior to implantation of the sensor. Differently stated, the sensor system can be pre-programmed to utilize a single desired algorithm, such as e.g., an algorithm selected for its particular attributes such as robustness, accuracy, etc. In another implementation, a medical practitioner may select (e.g., prescribe) one of multiple algorithms for use in a specific patient (i.e., user) prior to or after implantation of the sensor, ostensibly based on the desirability of that algorithm for use within the particular user based on their particular physiologic attributes, lifestyle, sensor location, etc. For example, in each of the foregoing implementations, the desired algorithm or the prescribed algorithm may be selected based on known algorithm characteristics (e.g., speed, accuracy, required processing power, robustness to errors, etc.), and/or characteristics of the user (e.g., known medications or treatments, known lifestyle characteristics, known disease characteristics, etc.), including based on prior analysis of the algorithms prior to implantation such as via computer analysis on various test or patient-derived data sets.

An exemplary decision tree 600 (i.e., Decision Tree-based algorithm) is shown in FIG. 6, wherein each end-node predicts a specific error (or source). The Decision Tree is generated using an algorithm which recursively splits a node (parent), containing training data, into two child nodes (Left and Right) based on a predictor variable, its threshold value, and an objective error criterion. The Left node comprises all of the training samples from the parent node that have predictor values less than the threshold whereas the Right node comprises all of the training samples from the parent node that have predictor values greater than or equal to the threshold. The (child) nodes are continued to be split until a termination criterion is met. For example, further splitting of a node can be terminated if the number of training samples in the node is equal to or smaller than a predefined threshold. The nodes that cannot be split further are called leaves (end-nodes). Once a Decision Tree is generated, an error estimation through this decision tree requires traversing the tree nodes utilizing binary decisions based on the respective model parameters and their thresholds. Once an end-node (also called 'leaf') of a tree is reached, the error estimate (e.g., mean value of the error in all of its training samples) associated with the leaf is used for the correction.

In yet another implementation, more than one machine learning algorithm (including e.g., Decision Tree, Random Forest, Naïve Bayes classification, support vector machines (SVM), Gradient Boosting, and AdaBoost) can be utilized to model the training data during operational model generation, and the algorithm that yields the "best" result can be used in the operational model. For example, the sensor system (or external platform such as the receiver 400, 450, or parent 600) can be pre-programmed to analyze the data via e.g., three (3) different machine learning algorithms, thereby generating at least three sets of data (i.e., at least one set of data output from each algorithm). Each of the sets of data can then be compared or otherwise evaluated against performance criteria to identify the "best" algorithm for generation of the operational model. In the foregoing example, the "best" algorithm may be selected based on a desired characteristic such as e.g., speed, accuracy, required processing power, robustness, and/or other desired features. The initial set of three algorithms in this example may be selected by the aforementioned experimental or other analytical evaluation, based on the particular attributes of the user in which the sensor 200 is intended to be implanted. For instance, the data vectors for a given individual (e.g., height/weight, BMI, race/ethnicity, age, stage of disease progression, etc.) can be evaluated to identify a previously determined subset of algorithms which are better suited to those falling within such classes, and their implanted sensor 200 preprogrammed with that subset of algorithms, in effect pre-filtering the algorithms for that individual so that the best algorithm(s) can be more rapidly converged on during model generation.

Further, in each of the foregoing implementations, the one or more machine learning algorithms may be differentially applied to selected portions of the collected data in order to analyze various parameters which may or may not be correlated with error occurring at the implanted sensor (i.e., correlated with the $BA_{error}$ data). In a variant where only the $BA_{cal}$ data are collected from the implanted sensor during training mode operation (i.e., no external data or $OS_{cal}$ data are received/collected), variables or parameters can include the sensor element(s) of origin (e.g., an identification of one of four sensor element pairs 206 shown in FIGS. 2-2A), electrode current at one or more of the sensor elements, rate-of-change (ROC) of electrode current at one or more of the sensor elements, reference (i.e., background) of oxygen concentration measured by one or more of the sensor elements, time of day (e.g., 6 AM, 7 AM, 8 AM, etc.), range of time of day (e.g., early morning, midday, night, etc.), range of blood analyte concentration (e.g., high range, median range, low range, etc.), age of sensor (i.e. length of time the sensor has been operating), impedance among sensor elements (both within the sensor itself and as measured through tissue adjacent to the sensor), and/or other determinable parameters that can be extracted from the sensor data.

In another variant where other data (e.g., internal $OS_{cal}$ data, external $OS_{cal}$ data, or other user input data) are received and/or collected in addition to the $BA_{cal}$ data during training mode operation, variables or parameters can additionally include temperature, acceleration, orientation, pressure, pulse rate, one or more other non-target blood analyte concentrations, intake of medication, intake of food, designated resting period of the user, designated active period the user, and/or other determinable parameters that can be extracted from the other sensor data and/or the user input data such as user state or context data. Per step 580 (FIG. 5D), a final list of one or more parameters is selected based on a predictor importance/relevance criterion.

As a brief aside, machine learning algorithms construct models of behavior from a set of sample inputs (here, e.g., blood glucose calibration data). Such models enable performance of a set of tasks as a function of previous experience, based on optimizing a performance metric as a function of the experience. Machine learning is typically further categorized into supervised, unsupervised and reinforcement based learning based on the types of input/output generated by the system.

So-called "supervised learning" algorithms determine a set of tasks to optimize outputs from a set of inputs; where a supervising entity (e.g., a human trainer) has defined the appropriate inputs and outputs. So-called "unsupervised learning" takes a non-curated data set and attempts to interpolate a series of relationships to identify e.g., inputs and outputs. So-called "reinforcement learning" algorithms are adapted to receive feedback over a plurality of training trials using dynamically generated input.

Various functions of the apparatus or systems described herein may be implemented within various ones of the foregoing categories of machine learning. For example, supervised learning solutions may be useful to quickly adapt the known input $BA_{cal}$ to the expected output $BA_{ref}$. Unsupervised learning may be used to find hidden correlations between the various sensor inputs; for example, unsupervised learning may be able to infer complex interrelationships between e.g., heart rate, oxygenation, and blood glucose which would be otherwise too complex to generically model, or the bases for which are unknown. Reinforcement techniques may be used by doctors, or other trained personnel to fine tune and or further tailor measurements. Still other applications of the foregoing will be readily appreciated by those of ordinary skill in the related arts.

The aforementioned machine learning algorithms are purely illustrative examples of artificial intelligence algorithms that are configured to adapt to changes in data sets. More generally, artisans of ordinary skill in the related arts will appreciate that any logic that is configured to learn or be trained from a set of initial training data, and subsequently predict or provide decisions for physiological parameters (e.g., glucose) may be substituted with equivalent success, given the contents of the present disclosure. For example, another machine learning algorithm referred to as Support Vector Machine (SVM) with a linear or non-linear kernel can be utilized to model the $BA_{error}$ as a function of input model parameters. In the case of a linear kernel SVM, $BA_{error}$ is modeled as a linear function of model parameters by utilizing a training data set and minimizing a pre-defined cost function (J) subject to criteria on residuals and cost function variables. As an example, if background pO2 (pO2) and rate-of-change of background pO2 (roc_pO2) are used as model parameters for estimating $BA_{error}$, a linear SVM model can be generated as:

$$F(x) = A*pO2 + B*roc\_pO2 + C \quad (4)$$

Where F(x) provides an estimate of $BA_{error}$, given the measurement of pO2 and roc_pO2 from the sensor, and A, B, C are model parameters generated using a training data set comprising n training samples, a cost function, and model constraints. Example forms of cost function (J) and model constraints (K) are provided below as eqns (5) and (6):

$$J = 0.5*(A*A + B*B) + x\sum_{n=1}^{N}(\mathcal{E}_n + \mathcal{E}_n^*) \quad (5)$$

$$K = \ast n \begin{cases} BA_{error} - (A*pO2 + B*roc\_pO2 + C) \leq \alpha + \mathcal{E}_n \\ (A*pO2 + B*roc\_pO2 + C) - BA_{error} \leq \alpha + \mathcal{E}_n^* \\ \mathcal{E}_n \geq 0 \\ \mathcal{E}_n^* \geq 0 \end{cases} \quad (6)$$

Where α is a predefined residual margin, and ε is a slack variable (soft margin) allowing the model generation to converge.

Per step 540, an operational model is then generated for prediction of $BA_{error}$ during normal operation of the implanted sensor (i.e., detection mode operation) based on the one or more selected/identified parameters and the determined relationship with $BA_{error}$. The model is stored at one or more of the storage devices discussed supra (step 542) for subsequent use during operation of the sensor system in the detection mode (step 510 of FIG. 5).

It will also be appreciated that instead of modeling the blood analyte error (e.g., $BG_{error}$ in the foregoing examples) directly, the apparatus and methods described herein may be adapted to use model parameters including for instance the "calibrated" CGM-generated blood glucose values ($CG_{cal}$), computed by applying a known calibration transform to the raw CGM data, to directly estimate a blood glucose value ($BG_{model}$). Therefore, $BG_{error}$ will indirectly be calculated as $BG_{model} - CG_{cal}$.

Also, in addition to estimating error in CGM-reported blood glucose, the modeling may be performed to estimate the error in the CGM-reported rate-of-change (ROC) of the blood glucose (e.g., the first derivative of the raw data over time), assuming sufficient numbers of reference blood glucose values collected closely in time are available to enable calculation of a reference rate-of-change. Hence, the "ROC" error can be estimated as $[ROC_{ref} - ROC_{CGM}]$.

Detection Mode Operation

Methods for collection and calculation of blood analyte level during detection mode operation of the sensor system are discussed with reference to FIGS. 5B and 5F.

Specifically, an exemplary embodiment of a method 522 of operating the implanted sensor 200 with the local receiver apparatus 400 and the parent platform 600 and/or the receiver and processor apparatus 450 for collection and calculation of detection mode $BA_{cal}$ data, as well as an exemplary method 529 of data processing and output during detection mode operation, are now described in detail.

It will be appreciated the method 522 is substantially similar during detection mode operation as during training mode operation, and thus much of the method described supra for determination of $BA_{cal}$ data during the training mode operation is applicable to determination of $BA_{cal}$ data during detection mode operation. Notably, whereas output of $BA_{cal}$ data (i.e., output of the blood analyte level) is optional in the training mode operation, such output is generally a primary function (non-optional) of the sensor system during the detection mode operation, so as to maintain the user and/or caregiver informed as to blood analyte level, and implement any relevant indication or alert regimes. In some instances (such as e.g., when the receiver is out of range of the implanted sensor), blood analyte data (and/or other internal data) can be continuously collected at the sensor during detection mode operation without (immediate) output of $BA_{cal}$ data.

Additionally, one or more of the data processing steps during the detection mode deviate from or supplement those in the training mode operation (e.g., method 529 of FIG. 5C). Specifically, the data processing step of the detection mode operation further includes (at least) application of the stored operational model on the implanted sensor analyte data ($BA_{cal}$ data).

Figure 5F:
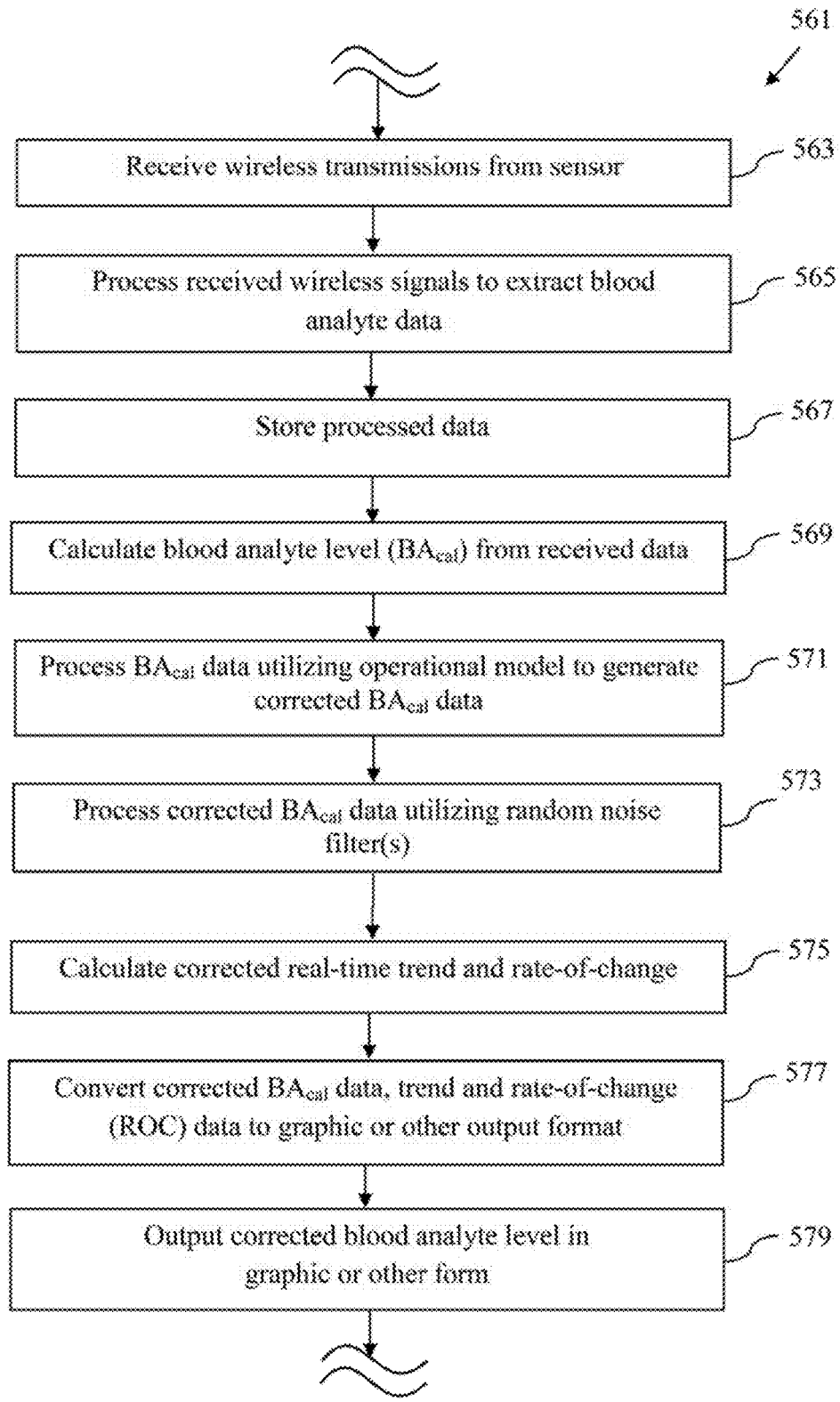
FIG. 5F is a logical flow diagram illustrating one exemplary implementation of the sensor data processing and output during "detection mode" operation according to the method of FIG. 5B.

As discussed supra, FIG. 5F is a logical flow diagram illustrating one exemplary implementation of the sensor data processing and output methodology 561 for the local receiver 400 and the parent platform 600 (or the receiver and processor apparatus 450) during detection mode operation according to the method 522 of FIG. 5B. As depicted in FIG. 5F, the method 561 in one embodiment includes first receiving the wireless data transmissions from the (implanted) sensor 200 per step 563. Next, per step 565, the received wireless signals are processed, and the processed data stored (step 567). Exemplary implementations of sensor data receipt and processing, including demodulation/unscrambling, for the receivers 400, 450 are described in U.S. patent application Ser. No. 15/368,436 previously incorporated herein.

Next, calculated blood analyte level ($BA_{cal}$) is determined per step 569. The $BA_{cal}$ data are then processed via application of the stored operational model on (i) the $BA_{cal}$ data, and (ii) data from the one or more identified parameters correlated with $BA_{error}$ (such as e.g., temperature data, motion data, orientation data, pulse rate data, other blood analyte concentration data, manually entered user data, etc.), thereby generating $BA_{cal}$ data corrected for $BA_{error}$ (i.e., systemic error from unmodeled user-specific variables) per step 571. In one implementation (implanted blood glucose sensor), once a new blood glucose sample is recorded by the system, it will compute all the model parameters selected and defined in the model parameters identification process using the new BG sample data (and any number of past samples needed). Once the model parameters are computed, the machine-learning model generated via the user-specific model generation process is applied to predict the $BG_{error}$. Similarly, $CG_{cal}$ (the "calibrated" CGM BG data) is computed by applying the known calibration transform to the raw CGM data, and the predicted $BG_{error}$ is subtracted from $CG_{cal}$ to provide a closer approximation of $BG_{ref}$ (albeit still containing effects due to random noise).

Optionally, one or more random noise signal filters can be applied to the corrected $BA_{cal}$ reading to additionally correct for error due to random noise (i.e., "e") per step 553 (see discussion of random noise supra).

Other parameters of interest if any (such as real-time trend and/or rate of change) are calculated based on the corrected $BA_{cal}$ data per step 573. Optionally, the calculated values from steps 571, 573, 575 are then converted per step 577 to a prescribed output format (e.g., a graphic rendering of a numeric value, a graphic display of a trend arrow, a sequence of haptic vibrations, etc.) consistent with the selected/configured output modality. The converted values or indications can then be output to the user in the appropriate modality/modalities per step 579, such as via the GUI.

It will be appreciated that the analyte sensor system may operate in detection mode simultaneously with its operation in training or re-training modes. That is, if a suitable model has already been made available to the sensor system (e.g. by previous training or by factory programming), then model-based error correction can be applied and error-corrected $BA_{cal}$ reported by the system even while the steps are being carried out to develop a new model (training or re-training). After the new model has achieved a sufficient state of readiness, then the system may abandon (or modify) the previous model in favor of a new model.

Re-Training Determination

As depicted in step 512 of FIG. 5, in one exemplary embodiment, the method of operating the sensor system 500 includes optional "re-training" of the sensor system. The aforementioned "re-training" substantially comprises a subsequent operation of the sensor system in the training mode after an initial training mode operation. As such, re-training may occur for example: (i) after implantation, and after an initial in vivo training operation; (ii) after implantation, and after an initial explanted training operation conducted before the sensor 200 is implanted; (iii) after explant, and subsequent re-implantation of the same or similar sensor 200 in the same individual.

Notably, such re-training can be used, inter alia, to compensate for short-term or long-term changes or variations in sensor response or subject physiology; i.e., how the sensor responds to prevailing in vivo and sensor operational conditions it finds itself in at any given point during its implanted lifetime. For example, one or more of the detector pairs of the sensor 200 may become less sensitive or more sensitive or fail over time, and/or the host's physiological responses (including FBR or other such factors) may vary as a function of time. Ancillary sensors on the sensor 200 (e.g., pressure, temperature, etc.) may also fail or their response characteristics may change, thereby necessitating their re-evaluation or removal from the algorithmic modeling process.

Moreover, the coupling or interface of the sensor 200 and the host's tissue may change, including due to mechanical events such as a physical impact, strenuous exercise or activity, etc., such that the sensor detector pairs must be "re-acclimated" to the new physical coupling after movement of the sensor 200 within its implantation pocket within the host's tissue. Yet further, new and previously un-modeled (within that individual) physiological or non-physiological error sources may arise over time, or other previously modeled sources (i.e., accounted for in the model developed after initial training) may wane over time. New algorithms may also be developed, and it may be desired to retro-fit them into an already implanted device.

As can be appreciated, any number of the above factors or others, may dictate a re-training of the sensor while in vivo. Generally speaking, many if not all of the above sources of possible variation in signal will manifest themselves in varying degree in the $BA_{error}$ value ultimately identified using the applied operational model, and hence the magnitude and/or rate of change (ROC), and/or number of data outliers (e.g., stability), can be used as a determinant or passive/post hoc indicator of change of one or more sensor operational or physiological processes. However, the present disclosure also contemplates proactive or advance determination of the change of one or more sensor operational or physiological processes.

Figure 5G:
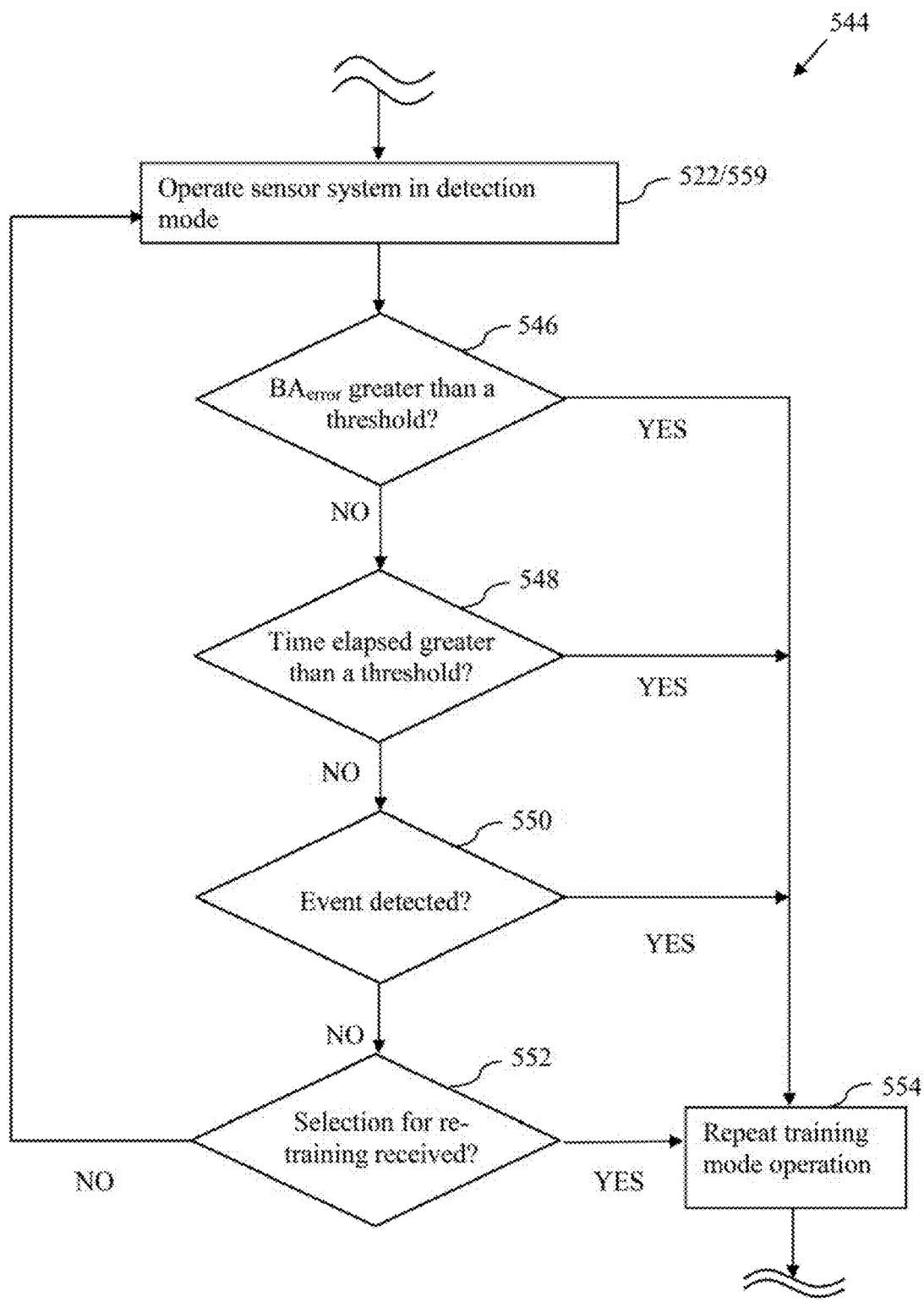
FIG. 5G is a logical flow diagram illustrating one exemplary implementation for determination of whether re-training criteria are met for the implantable sensor system according to the method of FIG. 5.

FIG. 5G is a logical flow diagram illustrating one exemplary implementation of a method 544 of determining the need for re-training of the sensor 200. This methodology can be implemented by the implanted sensor apparatus 200 (i.e., by logic operative thereon), by the local receiver 400 and the parent platform 600, the receiver and processor apparatus 450, or combinations of the foregoing (depending on how the logic is distributed within these devices), during detection mode operation according to the method 500 of FIG. 5.

As depicted in FIG. 5G, while the sensor system is operated in the detection mode (per methods 522 of FIG. 5A and 559 of FIG. 5F), it can be determined whether one or more criteria for re-training have been met, with any single criterion triggering re-training in the illustrated embodiment.

In the exemplary method 544, it is first determined whether $BA_{error}$ is greater than a pre-determined threshold at decision block 546; i.e., the magnitude of $BA_{error}$ averaged over a period of time is greater than a pre-determined threshold value for $BA_{error}$. In another variant, it can additionally or alternatively be determined whether the $BA_{error}$ outlier data include a number of outliers that are greater than an outlier threshold (or threshold percentage of the data; e.g., >20 percent are outliers). For example, a pre-determined threshold for a daily average $BA_{error}$ is +15% of respective $BA_{cal}$ values and/or a pre-determined $BA_{error}$ outlier data threshold is 30% of respective $BA_{cal}$ values. In both variants, if the determined $BA_{error}$ and/or $BA_{error}$ outlier data are greater than the respective pre-determined threshold(s), a repeated operation of the sensor system in the training mode can be initiated (step 554). In some examples, a notification is sent to the user to confirm or request initiation of a subsequent training mode.

Alternatively, per method 544, if $BA_{error}$ and/or $BA_{error}$ outlier data are less than the respective pre-determined threshold(s), other re-training criteria can be determined.

Per decision block 548, it is next determined if a time elapsed since initiation of the detection mode is greater than a pre-determined threshold (e.g., a duration of time for operating the sensor system in the detection mode and hence without training). In one specific example, a pre-determined threshold for a time period for detection mode operation is one week. Thus, if the sensor system has been operating in the detection mode for a duration of time greater than the per-determined threshold, a repeated operation of the sensor system in the training mode is initiated (step 554), so as to keep the error correction capability of the system "fresh" in light of any potential physical or physiological changes in the operation of the sensor 200.

Alternatively, if a time elapsed since the initiation of the detection mode operation is less than the pre-determined threshold, other re-training criteria can be evaluated.

In the method 544, it is further determined whether a "re-training event" has been detected per decision block 550. If such an event is detected, a repeated operation of the sensor system in the training mode is initiated (step 554). Alternatively, if no re-training event is detected, other re-training criteria can be evaluated.

Exemplary re-training events can include one or more of: (i) notification (e.g., via wireless message to/from the sensor apparatus from/to the external receiver) or internal determination that the sensor system has been recalibrated, (ii) detection of an occurrence of an unusually high temperature (e.g., detection of a temperature greater or less than a pre-determined high/low temperature threshold, respectively, and/or detection of the high/low temperature for a duration of time greater than a pre-determined threshold); (iii) detection of a physical impact to the user (e.g., detection of a pressure and/or acceleration value greater than a pre-determined threshold; (iv) detection of an occurrence of an unusually high or low pulse rate (e.g., detection of a pulse rate greater/less than a pre-determined high/low pulse rate threshold respectively, and/or detection the high/low pulse rate for a duration of time greater than a pre-determined threshold); (v) detection of a change in electrical impedance among sensor electrodes; (vi) detection of an increase in variance in the outputs among redundant or duplicative detectors, either located in the same sensor housing or in separate sensors; (vii) detection of change/drift in moving average of the direct sensor measurements or derived sensor measurements, e.g. average daily pO2, average weekly pO2, average daily concentration of glucose, change in daily correlation among different Cg channels when multiple detectors/pairs are available, daily correlation among different O2 channels, daily correlation between Cg and O2 channel, etc.

In some implementations, the re-training events can be selected by the sensor system based on the identified parameters which are correlated to $BA_{error}$ for the specific user. For example, if temperature is correlated to $BA_{error}$ while pulse rate is uncorrelated, re-training events can include the occurrence of the foregoing temperature events, while the aforementioned pulse rate events are excluded from the set of events that initiate retraining.

Per decision block 552, it is next determined whether a command or selection for re-training has been received. Specifically, a user, a medical professional, and/or a caretaker can input a request for re-training of the sensor system, such as based on known user information, or merely as a "soft re-boot" (e.g., to attempt to clear prospectively anomalous behavior by the sensor 200). For example, if a user undergoes a significant lifestyle change (e.g., change in diet or exercise regimen), a change in disease presentation, a physiological change (e.g., onset of a transient illness or diagnosis of a secondary disease, significant weight gain or weight loss, etc.), a change in medication, goes on a vacation or other deviation from normal routine, such changes may warrant retraining to ensure that the generated model is still applicable and optimized. In another example, a user may sense a feeling of being "off" or a sensation of malaise, and may selectively initiate retraining as desired. If a selection for re-training is received, a repeated operation of the sensor system in the training mode is initiated (step 554). Alternatively, if no selection for re-training is received (in addition to a "NO" for each of the other criteria of decision blocks 546-550) operation of the sensor system in the detection mode is continued according to the methods 552 and 559.

It will be appreciated by those skilled in the art given this disclosure that the exemplary method 544 is just one possible method for determining if re-training criteria are met. In alternate implementations, the method can include more or fewer decision blocks, and/or the decision blocks can be executed in a different sequence. Other logical constructs may also be used, such as e.g., a "coincidence" requirement where two or three criteria must simultaneously be met in order to trigger re-training. Moreover, a hierarchy of evaluation may be determined and leveraged; i.e., the order and frequency with which the various criteria are evaluated may be adjusted, such as where a most likely re-training factor/threshold to be exceeded is evaluated first at a first frequency, and other less-likely factors/thresholds evaluated at a reduced frequency.

Figure 7:
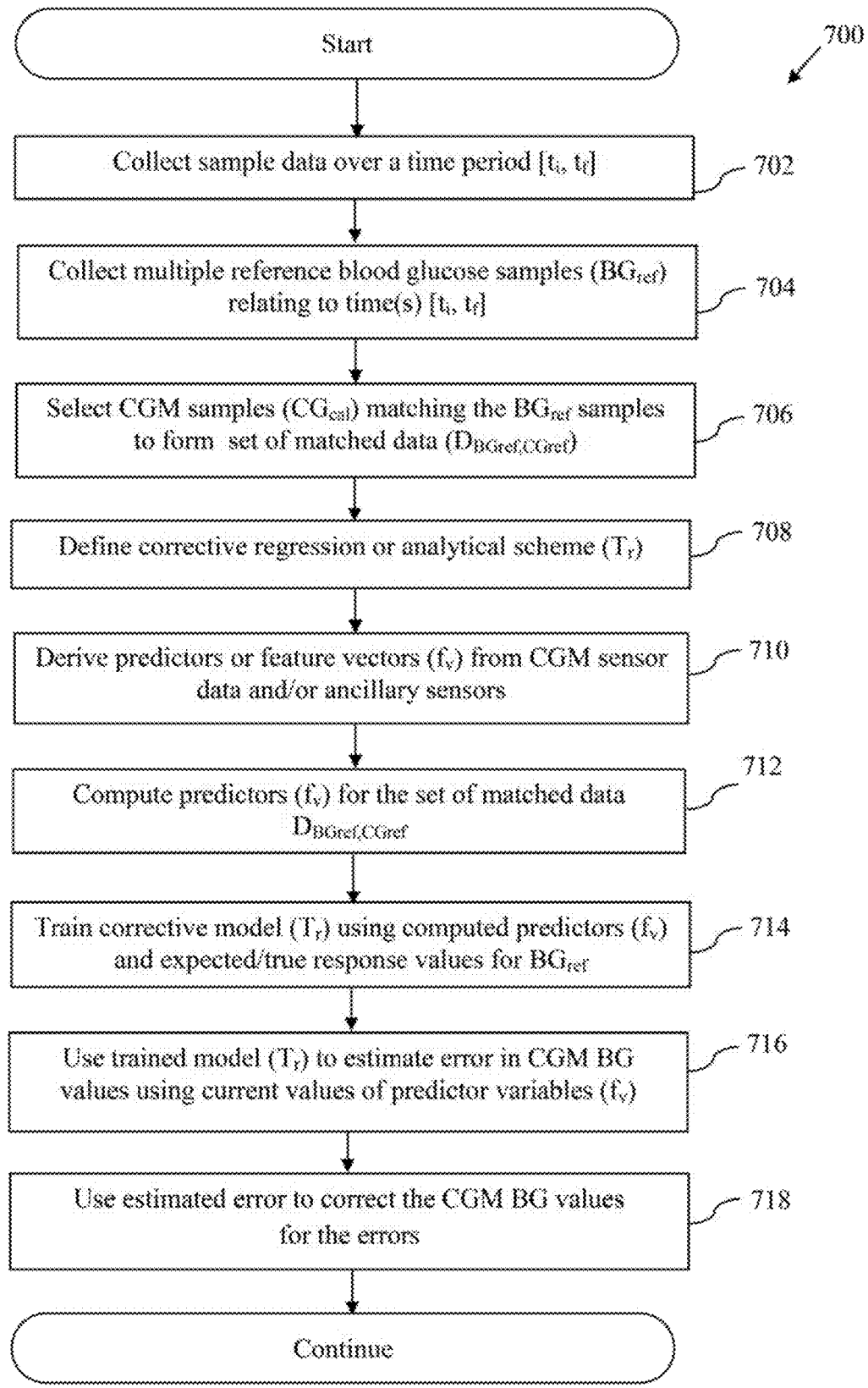
FIG. 7 is a logical flow diagram illustrating one exemplary implementation of the generalized method of operating the implantable sensor system for blood analyte measurement according to FIG. 5, in the context of an implantable oxygen-based blood glucose sensor having a plurality of detector pairs.

FIG. 7 illustrates one particular implementation of the foregoing methodology of correcting for systematic error ($BA_{error}$=Blood Glucose error or $BG_{error}$) in the reported blood analyte level value(s) of FIGS. 5-5F, in the context of an implantable oxygen-based blood continuous glucose monitor (CGM) having multiple detectors/pairs, for purposes of illustration. As shown in FIG. 7, the method 700 includes first collecting sample data from the CGM over a time period $[t_i, t_j]$ per step 702. Multiple reference blood glucose samples ($BG_{ref}$) relating to the same time(s) $[t_i, t_j]$ are also collected per step 704.

Next, CGM-generated samples ($CG_{cal}$) matching the $BG_{ref}$ samples based on a specified criterion (e.g., time and/or CGM measurements rate-of-change) are selected to form a set of matched data ($D_{BGref,CGref}$) per step 706.

A corrective regression or analytical scheme ($T_r$) (e.g. Decision Tree, Random Forest, linear regression, etc.) is next defined per step 708, and one or more predictors or feature vectors ($f_v$) are derived from CGM sensor data and/or ancillary sensors (e.g., fingerstick meters, thermistors, accelerometers, etc.) per step 710.

Predictor variables ($f_v$) for the set of matched data $D_{BGre}f$, $C_{Gref}$ are then computed per step 712. These vectors are used within the regression or other analytical model framework to predict respective systematic errors. The corrective regression model ($T_r$) is then "trained" using the computed predictors ($f_v$) and the expected/true response values for blood glucose ($BG_{ref}$) per step 714.

The trained regression model ($T_r$) is then used in step 716 to estimate (in real-time) the error in CGM-reported blood glucose values by processing (then) current new values of the predictor variables ($f_v$), and the estimated error is used in real-time to correct the CGM-reported blood glucose for the effect of such errors (step 718).

Exhibit I hereto contains exemplary computer code implementing one or more aspects of the foregoing methodologies.

Population-Based Models

In some embodiments, the foregoing training mode operation of the sensor system can be carried out in an experimental or analytical setting on a population (such as e.g., a statistically significant group of test subjects) to build multiple "user-type" operational models, which can inter alia, be later applied to other users with similar characteristics to determine $BA_{error}$. In one such embodiment, user characteristics of the test subject(s) are identified, and each of the test subjects is implanted with a sensor (e.g., pursuant to their normal implantation schedule or needs), and the sensor operated in the training mode (discussed supra). An operational model is then generated for each test subject (whether via onboard processing logic of the implanted sensor, off-board processing via the receiver 400, 450, the parent platform 600, or cloud-based entity such as a server maintained by a health care administrator or even the manufacturer of the sensor, or combinations of the foregoing), and the operational model correlated to the user characteristics, in order to generate one or more population-based operational models or "user-type" operational models.

After such model development, characteristics of other users (i.e., non-test subject users, such as new patients) can be identified, and a specific population-based operational model can be implemented based on the identified characteristics within the implanted sensor system, without the need for operation of the implanted sensor in the training mode (or rather a confirmatory training process). For example, it may be found that persons of a certain gender, age, race or ethnicity, physiologic profile—which may include the presence or absence of certain genetic markers, blood constituents (e.g., proteins, antibodies, antigens, etc.), BMI, or other parameter, exhibit certain types of systematic or other error sources relative to the BG measurement, with a high degree of statistical confidence. This correlation can be used in picking an operational model for a user falling within such class prior to or in place of user-specific operational models.

Moreover, the efficacy or accuracy of such population-based correlations can be assessed based on in vivo data obtained from that user. For example, the implanted sensor can be used to gather data from that particular individual (e.g., according to the methods of FIGS. 5-7 above) and development of a user-specific model, which can then be compared to the population-based model to identify variations therebetween. If the user-specific models developed for numerous individual users show significant statistical divergence or variation from the relevant population-based model(s) selected for that user, then the strength of the statistical correlation or confidence in the population-based models is necessarily low, and their structure (e.g., in terms of errors modeled) and/or selection criteria may need further refinement. In a simple example, assessments of the divergence of the error corrections or corrected BG values produced by the user-specific model could be utilized to de-select a population-based model for a specific user.

Hence, in one approach ("evaluation mode"), the user-specific (training mode derived) model can be run in parallel with the pre-designated population-based model on the same in vivo user data to generate corrected BG level outputs for each; these can then be compared to e.g., an external calibration data source or other "gold standard" for the actual BG level in that user at that time, to assess model performance.

Likewise, the sensor system may be programmed to utilize the population-based model (thereby ostensibly obviating training) until one or more indicia of divergence are seen; e.g., where the population model begins to diverge significantly in magnitude, or at a rate greater than a prescribed value, based on periodic external calibration. At such point, the system (e.g., sensor 200) may automatically invoke implementation of "training" via the methodologies described above, and replacement or augmentation of the population-based model with the indigenously developed user-specific model, for subsequent operation within that particular user.

In some examples, the group of test subjects are a selected group of volunteers. In other examples, the group of test subjects can be existing users from which data are collected for generation of population-based models.

Figure 8:
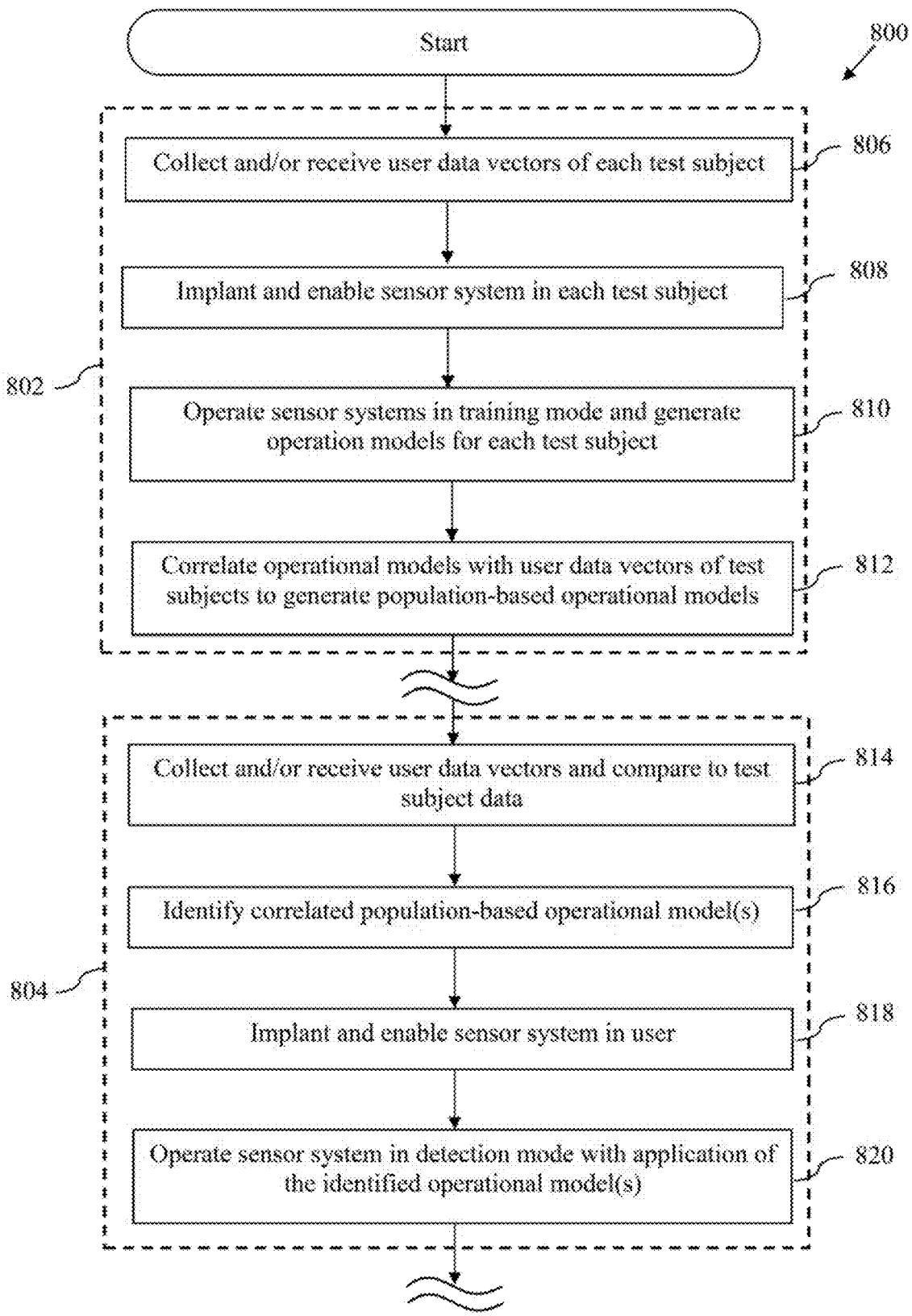
FIG. 8 is a logical flow diagram illustrating another exemplary embodiment of a population-based method of operating the implantable sensor system for blood analyte measurement according to the present disclosure.

One exemplary implementation of a method 800 for generation and application of population-based operational models is shown and described in a logical flow diagram depicted in FIG. 8. The method 800 generally (ii) includes an analytical or experimental phase 802 for generation of the population-based operational model(s), and (ii) a utilization phase 804 for application one of the population-based operational models during normal (or trial) use of the sensor system.

As illustrated in FIG. 8, the analytical or experimental phase 802 begins with collecting (e.g., derived from measurable information) or receiving (e.g., manually input test subject information) a series of user data vectors such as e.g., gender, height, weight, diet, exercise regimen, disease presentation, medications, blood pressure, active pulse rate, resting pulse rate, average body temperature, geographic region of residence, etc. from each member in a group of test subjects (step 806). In some examples, the selected user data vectors are combined into an input vector and/or organized into a matrix of user data vectors.

Per step 808, each of the test subjects is implanted with a sensor 200. After the sensor is implanted and enabled, the sensor system is operated in a training mode (such as e.g., the training mode operation shown in FIGS. 5-5C, discussed supra) in order to generate an operational model for each test subject (step 810). After download of the model data from the sensor system (e.g., via wireless transmission from the implanted sensor 200, or the receiver 400, 450), the various operational models are then correlated with the respective previously collected and/or received user data vectors to identify user characteristics that are associated with each operational model, thereby generating a set of population-based operational models (step 812). Such correlation may be statistical in nature (e.g., according to mean error, standard deviation/variance, and/or other statistical criteria as determined by algorithmic analysis by a computerized system), or even heuristic (e.g., by a human utilizing inductive reasoning or other cognitive tools to identify patterns in both the models and the data sets).

Subsequently, the experimentally determined population-based operational models can be utilized for operation of an implanted sensor system with non-test subject users (phase 804, discussed supra). Specifically, in the exemplary method 800, user data vectors are collected and/or received from a user (i.e., a non-test subject user, such as a new patient), and then compared to the test subject data vectors per step 814 that are correlated with the particular population-based model(s). It will be appreciated that the series of user data vectors for the non-test subject user are substantially similar to those collected and/or received from the test subjects during the experimental phase 802 such that a "best" match comparison can be performed. Further, in some examples, the selected user data vectors may be combined into an input vector and/or organized into a matrix of user data vectors in a substantially similar manner as is carried out for the test subject user data vectors in order to carry out the comparison.

Per step 816, a correlated population-based operational model is identified based at least on the input vectors for the user. The user is implanted with the sensor and the sensor system is enabled per step 818. The sensor system is then operated in the detection mode (such as e.g., the training mode operation shown in FIGS. 5A-5C, discussed supra) utilizing the population-based operational model to correct for $BA_{error}$ (step 820). Thus, in this embodiment, the sensor system is operated in the detection mode (with application of the experimentally determined population-based operational model) directly after implantation without prior or initial operation in a training mode.

Although not specifically shown in method 800 of FIG. 8, in alternate embodiments, the method can further include determining if one or more re-training criteria are met (substantially similar to method 544 shown in FIG. 5G). In this embodiment, the population-based operational model can be updated or replaced as necessary or as desired by the user. Re-training criteria can include those determined from population characteristics (e.g. retraining at time intervals found to provide optimum performance in the population) or other thresholds and variables specific to the individual user, as described supra.

It will be recognized that while certain embodiments of the present disclosure are described in terms of a specific sequence of steps of a method, these descriptions are only illustrative of the broader methods described herein, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the disclosure and claimed herein.

While the above detailed description has shown, described, and pointed out novel features as applied to various embodiments, it will be understood that various omissions, substitutions, and changes in the form and details of the device or process illustrated may be made by those skilled in the art without departing from principles described herein. The foregoing description is of the best mode presently contemplated. This description is in no way meant to be limiting, but rather should be taken as illustrative of the general principles described herein. The scope of the disclosure should be determined with reference to the claims.

Exhibit I

Exemplary Computer Code

© 2017 GlySens, Inc. All Rights Reserved

```
%% Function performing feature (modeling parameters) selection
% Apply calibration to sensor measurements and return
% calculated Cg subject to systematic errors and modeling parameters
[Cg_preprocessed_cal, featureSet1, featureSet2, featureSet3]=computeCgUsingCalCoeffs(sensorRawIworks_cal, O2_Calibration_coeffs, Cg_cal_coeffs);
feature_composite=[featureSet1, featureSet2, featureSet3];
Cg_error=BloodGlucoseReference.samples−Cg_preprocessed_cal;
numOfFeatures=size(feature_composite,2); % number of modeling parameters
% linear correlation between parameters and the BG error
correlationIndex=zeros(numOfFeatures,1);
for i=1: numOfFeatures
    correlationBwFeatureAndError=corrcoef(Cg_error, feature_composite(:,i));
    correlationIndex(i,1)=abs(correlationBwFeatureAndError(1,2));
end
importantFeatureIndices=find(correlationIndex >0.4); % Selected features
if(length(importantFeatureIndices)<5)
    [~, idxs]=sort(correlationIndex, 'descend');
    importantFeatureIndices=idxs(1:5);
end
```

What is claimed is:

1. A computerized apparatus for use with an implantable blood analyte sensor apparatus, the implantable blood analyte sensor configured to monitor a blood analyte concentration of a subject, the computerized apparatus comprising:
    data processing apparatus, the data processing apparatus configured for data communication with a blood analyte sensor apparatus; and
    a data storage apparatus in data communication with the data processing apparatus, the data storage apparatus comprising at least one computer program, the at least one computer program comprising a plurality of instructions which are configured to, when executed by the data processing apparatus, cause the computerized apparatus to:
        (i) receive calibration data;
        (ii) cause operation of the blood analyte sensor apparatus in an initial training mode after implantation thereof within the subject and calibration of the blood analyte sensor apparatus, the operation in the initial training mode comprising at least: (a) receipt of a time-stamped series of blood analyte reference data, and (b) calculation of a time-stamped series of calibrated blood analyte sensor data via utilization of at least the calibration data and blood analyte signal data collected from one or more detectors of the blood analyte sensor apparatus;
        (iii) based at least in part on the operation of the blood analyte sensor apparatus in the initial training mode, cause generation of an error correction operational model, the generation of the error correction operational model comprising at least:
            association of the time-stamped series of blood analyte reference data with the time-stamped series of calibrated blood analyte sensor data to generate a plurality of temporally-correlated blood analyte data sets each corresponding to one of a plurality of time points;
            calculation of data related to a plurality of blood analyte error values from the plurality of temporally-correlated blood analyte data sets; and
            utilization of one or more machine learning algorithms on at least a portion of the data related to the plurality of error values and data related to one or more candidate parameters to model one or more previously unmodeled error sources related to the implantation of the blood analyte sensor within the subject; and
        (iv) subsequent to generation of the error correction operational model, cause operation of the implantable blood analyte sensor apparatus in a detection mode, the operation in the detection mode comprising at least input of (a) subsequent blood analyte signal data collected from the one or more detectors of the implantable blood analyte sensor apparatus, and (b) subsequent data related to at least one of the one or more candidate parameters into the correction operational model to calculate data related to blood analyte level of the subject that is corrected for the one or more previously unmodeled error sources.

2. The computerized apparatus of claim 1, wherein the implantable blood analyte sensor apparatus comprises an oxygen-based blood glucose sensor, and the analyte signal data comprises blood glucose signal data.

3. The computerized apparatus of claim 2, wherein the receipt of time-stamped blood analyte reference data comprises receipt, via at least a wireless interface of the implantable blood analyte sensor apparatus, of a series of time-stamped blood glucose reference data generated by an external source.

4. The computerized apparatus of claim 3, wherein the series of time-stamped blood glucose reference data generated by the external source comprises a series of fingerstick-based blood glucose concentration data taken over a period of time, and the receipt via the wireless interface comprises receipt of the series of fingerstick-based blood glucose reference data transmitted from a wireless-enabled fingerstick device in wireless data communication with the data processor apparatus via the at least wireless interface of the implantable blood analyte sensor apparatus.

5. The computerized apparatus of claim 1, wherein the computerized apparatus is disposed on or within the implantable blood analyte sensor apparatus and is integrated therewith.

6. The computerized apparatus of claim 1, wherein the computerized apparatus is disposed on or within a receiver apparatus, the receiver apparatus configured to be disposed external to the subject within whom the implantable blood analyte sensor apparatus is implanted.

7. The computerized apparatus of claim 1, wherein:
the computerized apparatus is disposed on or within the implantable blood analyte sensor apparatus;
the causation of generation of the error correction operational model at least in part comprises transmission of the blood analyte signal data collected during the training mode via a wireless interface of the blood analyte sensor apparatus to an external receiver, the external receiver configured to perform the generation of the error correction operational model; and
the causation of operation in the detection mode at least in part comprises receipt of data indicative of the error correction operational model via the wireless interface from the external receiver.

8. The computerized apparatus of claim 1, wherein:
the operation of the implantable blood analyte sensor apparatus in the initial training mode further comprises collection of one or more series of time stamped non-analyte data, each the one or more series of time stamped non-analyte data based on signals generated by one or more in vivo sensors, the one or more in vivo sensors each comprising a sensor other than a blood analyte sensor, the data related to the one or more candidate parameters comprising at least the one or more series of time-stamped non-analyte data; and
the generation of the error correction operational model further comprises:
(i) association of each of the one or more series of time-stamped non-analyte data with one of the plurality of error values at each of the plurality of corresponding time points;
(ii) identification of one or more correlating parameters from the one or more series of time-stamped non-analyte data which correlate with the plurality of error values; and
(iv) utilization of at least one of the one or more correlating parameters in the generation of the error correction operational model.

9. The computerized apparatus of claim 8, wherein:
the one or more in vivo sensors comprise at least a pressure sensor, a thermometer, and an accelerometer; and
the one or more the one or more non-analyte data sets comprise at least pressure data, temperature data, and motion data.

10. The computerized apparatus of claim 8, wherein the input of the subsequent data related to the at least one of the one or more candidate parameters comprises input of subsequent non-analyte signal data corresponding to the at least one of the one or more correlating parameters into the error correction operational model to calculate data related to blood analyte level of the subject that is corrected for the one or more previously unmodeled error sources, the subsequent non-analyte signal data collected from at least one of the one or more in vivo sensors.

11. The computerized apparatus of claim 1, wherein the utilization of one or more machine learning algorithms on the at least portion of the data related to the plurality of error values and the data related to one or more candidate parameters to model one or more previously unmodeled error sources related to the implantation of the blood analyte sensor within the subject comprises:
(i) association of the data related to the one or more candidate parameters with the plurality of blood analyte error values at each of the plurality of time points;
(ii) identification of individual ones of the one or more candidate parameters which each have a correlation to the plurality of error values; and
(iii) utilization of data related to at least one correlating parameter from the one or more candidate parameters to generate the error correction operational model, the input of subsequent data related to at least one of the one or more candidate parameters comprising input of subsequent data related to the at least one correlating parameter into the at least one error correction operational model to calculate data related to blood analyte level of the subject that is corrected for the one or more previously unmodeled error sources.

12. The computerized apparatus of claim 11, wherein the data related to one or more candidate parameters comprises at least data related to a plurality of blood analyte concentration ranges, data related to a plurality of specified time periods, and data related to rate of change (ROC) of the blood analyte signal data.

13. The computerized apparatus of claim 1, wherein the utilization of one or more machine learning algorithms on the at least portion of the plurality of error values and the data related to one or more candidate parameters comprises at least:
utilization of a first machine learning algorithm on the at least portion of the plurality of error values and the data related to one or more candidate parameters to generate a first error model data set;
utilization of a second machine learning algorithm on the at least portion of the plurality error values and the data related to one or more candidate parameters to generate a second error model data set;

evaluation of the first error model data set and the second error model data set with regard to one or more predetermined model selection criteria; and
based at least in part on the evaluation, selection of one of the first machine learning algorithm or the second machine learning algorithm for use in the generation of the error correction operational model.

14. A method of operating an implanted blood analyte sensor for adapting blood analyte detection thereof to a subject after implantation of the blood analyte sensor within the subject, the implanted blood analyte sensor subject to one or more a priori unmodeled systematic errors after the implantation thereof within the subject, the method comprising:
calibrating the implanted blood analyte sensor;
obtaining first calibrated blood analyte data using the calibrated blood analyte sensor, the first calibrated blood analyte data subject to the one or more a priori unmodeled systematic errors;
obtaining corresponding reference data not subject to the one or more a priori unmodeled systematic errors;
associating the first calibrated blood analyte data and the corresponding reference data at each of a plurality of corresponding time points;
calculating a plurality of blood analyte error values, each of the plurality of blood analyte error values associated with one of the plurality of corresponding time points from the first calibrated blood analyte data and the corresponding reference data;
evaluating at least data related to one or more parameters abstracted from the first calibrated blood analyte data and the plurality of blood analyte error values using one or more machine learning algorithms;
generating an operational error correction model based at least on the evaluating;
subsequent to the generating of the operation error correction model, obtaining second calibrated blood analyte data using the implanted blood analyte sensor, the second calibrated blood analyte data subject to the one or more a priori unmodeled systematic errors; and
inputting at least the second calibrated blood analyte data into the operational error correction model to generate blood analyte level data corrected for at least one of the one or more a priori unmodeled systematic errors.

15. The method of claim 14, wherein the method does not require identification or human understanding of one or more physical or physiologic mechanisms causing the at least one of the one or more a priori unmodeled systematic errors.

16. The method of claim 14, further comprising accessing one or more non-analyte candidate parameter data sets; and
associating each of the one or more non-analyte candidate parameter data sets with the plurality of blood analyte error values at each of the plurality of corresponding time points;
wherein the evaluating further comprises evaluating the one or more non-analyte candidate parameter data sets and the data related to the one or more parameters abstracted from the first calibrated blood analyte data using the one or more machine learning algorithms to identify at least one correlating parameter which correlates with the plurality of blood analyte error values, the at least one correlating parameter utilized in the generating of the operational error correction model.

17. The method of claim 16, further comprising receiving each the one or more non-analyte candidate parameter data sets from at least one non-analyte sensor in data communication with a processor apparatus of the implantable analyte sensor.

18. The method of claim 16, further comprising:
subsequent to the generating of the operation error correction model, obtaining new data related to the at least one correlating parameter; and
inputting the new data related to the at least one correlating parameter into the operational error correction model to generate blood analyte level data corrected for at least one of the one or more a priori unmodeled systematic errors.

19. A computerized apparatus for use with a continuous glucose monitor (CGM) apparatus and configured to correct for previously unmodeled systematic error in CGM-reported blood glucose data after implantation of the CGM apparatus within a subject, the computerized apparatus comprising:
data processing apparatus, the data processing apparatus configured for data communication with the CGM apparatus; and
data storage apparatus in data communication with the data processing apparatus, the data storage apparatus comprising at least one computer program stored thereon, the at least one computer program comprising a plurality of instructions which are configured to, when executed by the data processing apparatus, cause the computerized apparatus to:
collect CGM sample data from the CGM apparatus at least over a first time period after the implantation of the CGM within the subject;
collect reference blood glucose (BG) sample data at least over the first time period;
select CGM sample data matching the reference BG sample data based on a plurality of corresponding time points within the first period of time to form a set of matched BG data;
calculate BG error data from the set of matched BG data at each of at least a portion of the plurality of corresponding time points;
define at least one machine learning regression model, and select one or more candidate parameters derived from at least sensor data associated with at least one analyte sensor and/or received non-analyte data associated with one or more non-analyte sensors;
compute a plurality of predictor variable values from each of the one or more candidate parameters for the set of matched data, each of the plurality of predictor variable values associated with one of the plurality of corresponding time points;
based at least in part on the computation of the plurality of predictor variables, identify one or more correlating parameters which correlate with the BG error data;
train the at least one machine learning regression model using at least data related to the one or more correlating parameters and the BG error data to generate a trained at least one regression model;
utilize the trained at least one regression model to estimate error in a current new CGM-reported blood glucose value based at least on one or more current new values for at least one of the one or more correlating parameters; and
utilize the estimated error to correct the current new CGM-reported blood glucose data.

20. The computerized apparatus of claim 19, wherein the CGM apparatus comprises a fully implantable subcutaneous CGM apparatus configured for long-term implantation within the subject, and the trained at least one regression model is configured to correct for systemic errors associated with fully subcutaneous long-term implantation of the CGM apparatus within the subject.

* * * * *